United States Patent
Masaki et al.

(10) Patent No.: US 9,096,531 B2
(45) Date of Patent: Aug. 4, 2015

(54) FUSED IMIDAZOLE DERIVATIVE

(75) Inventors: Hidekazu Masaki, Saitama (JP);
Hiroshi Takasugi, Saitama (JP);
Tomoyuki Nagayama, Chuo-ku (JP);
Ryutaro Shimono, Saitama (JP); Yujiro Uchino, Saitama (JP); Koichi Takayanagi, Saitama (JP)

(73) Assignee: TOA EIYO LTD., Tokyo (JP)

( * ) Notice: Subject to any disclaimer, the term of this patent is extended or adjusted under 35 U.S.C. 154(b) by 0 days.

(21) Appl. No.: 13/699,692

(22) PCT Filed: May 24, 2011

(86) PCT No.: PCT/JP2011/061913
§ 371 (c)(1),
(2), (4) Date: Nov. 23, 2012

(87) PCT Pub. No.: WO2011/148956
PCT Pub. Date: Dec. 1, 2011

(65) Prior Publication Data
US 2013/0065896 A1    Mar. 14, 2013

(30) Foreign Application Priority Data

May 24, 2010 (JP) .................................. 2010-117962

(51) Int. Cl.
| | | |
|---|---|---|
| *A61K 31/44* | (2006.01) | |
| *A61K 31/415* | (2006.01) | |
| *C07D 471/02* | (2006.01) | |
| *C07D 491/02* | (2006.01) | |
| *C07D 498/02* | (2006.01) | |
| *C07D 513/02* | (2006.01) | |
| *C07D 515/02* | (2006.01) | |
| *C07D 235/00* | (2006.01) | |
| *C07D 235/24* | (2006.01) | |
| *C07D 235/12* | (2006.01) | |
| *C07D 235/14* | (2006.01) | |
| *C07D 235/16* | (2006.01) | |
| *C07D 401/06* | (2006.01) | |
| *C07D 401/12* | (2006.01) | |
| *C07D 405/06* | (2006.01) | |
| *C07D 471/04* | (2006.01) | |
| *C07D 473/00* | (2006.01) | |

(52) U.S. Cl.
CPC ............ *C07D 235/12* (2013.01); *C07D 235/14* (2013.01); *C07D 235/16* (2013.01); *C07D 401/06* (2013.01); *C07D 401/12* (2013.01); *C07D 405/06* (2013.01); *C07D 471/04* (2013.01); *C07D 473/00* (2013.01)

(58) Field of Classification Search
None
See application file for complete search history.

(56) References Cited

U.S. PATENT DOCUMENTS

| | | | | |
|---|---|---|---|---|
| 3,951,968 | A  * | 4/1976 | Fauran et al. | .................... 544/99 |
| 6,316,474 | B1 * | 11/2001 | McCauley et al. | ............ 514/338 |
| 6,660,744 | B1 | 12/2003 | Hirst et al. | |
| 6,921,763 | B2 | 7/2005 | Hirst et al. | |
| 7,332,497 | B2 * | 2/2008 | Hirst et al. | ................. 514/262.1 |
| 2004/0006083 | A1 | 1/2004 | Hirst et al. | |
| 2005/0197351 | A1 | 9/2005 | Lee et al. | |
| 2007/0167440 | A1 | 7/2007 | Moritani et al. | |
| 2007/0173504 | A1 | 7/2007 | Pacofsky et al. | |
| 2007/0197523 | A1 | 8/2007 | Pacofsky et al. | |
| 2007/0259867 | A1 | 11/2007 | Cho et al. | |
| 2008/0167329 | A1 | 7/2008 | Barrow et al. | |
| 2009/0275550 | A1 | 11/2009 | Barrow et al. | |
| 2009/0286806 | A1 | 11/2009 | Pajouhesh et al. | |
| 2010/0056545 | A1 | 3/2010 | Shin et al. | |

(Continued)

FOREIGN PATENT DOCUMENTS

| | | |
|---|---|---|
| CN | 1942447 A | 4/2007 |
| FR | 2 292 473 | 6/1976 |

(Continued)

OTHER PUBLICATIONS

Carey, FA. Organic Chemistry 6th Ed. McGraw Hill. 2006, chapter 1, p. 9.*

(Continued)

*Primary Examiner* — Rita Desai
*Assistant Examiner* — Ben S Michelson
(74) *Attorney, Agent, or Firm* — Oblon, McClelland, Maier & Neustadt, L.L.P.

(57) ABSTRACT

Provided is a novel compound which shows an antagonistic effect against T-type calcium channels, and is useful as a pharmaceutical product.

A compound represented by general formula (I), and a pharmaceutical agent containing the same, are disclosed:

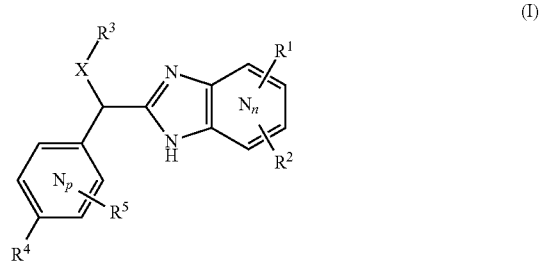

(I)

wherein n represents the number of nitrogen atoms contained in the 6-membered fused aromatic ring, and is 0, 1 or 2; p represents the number of nitrogen atoms contained in the 6-membered aromatic ring, and is 0 or 1; X represents an oxygen atom, $-SO_2-$ or $-N(R^9)-$; and $R^1$ to $R^5$ each represents a hydrogen atom or other substituents.

9 Claims, No Drawings

(56) References Cited

U.S. PATENT DOCUMENTS

| | | | |
|---|---|---|---|
| 2010/0087446 | A1 | 4/2010 | Chakravarty et al. |
| 2010/0216841 | A1 | 8/2010 | Barrow et al. |
| 2010/0222387 | A1 | 9/2010 | Barrow et al. |
| 2010/0261741 | A1 | 10/2010 | Barrow et al. |
| 2011/0112064 | A1 | 5/2011 | Barrow et al. |

FOREIGN PATENT DOCUMENTS

| | | |
|---|---|---|
| JP | 11 54015 | 4/1999 |
| JP | 2004 531513 | 10/2004 |
| JP | 2005 501811 | 1/2005 |
| JP | 2005 239708 | 9/2005 |
| JP | 2006 219472 | 8/2006 |
| JP | 2007 297366 | 11/2007 |
| JP | 2008 533020 | 8/2008 |
| JP | 2008 546800 | 12/2008 |
| JP | 2009 500340 | 1/2009 |
| JP | 2009 521461 | 6/2009 |
| JP | 2009 521471 | 6/2009 |
| JP | 2009 149670 | 7/2009 |
| JP | 2009 534320 | 9/2009 |
| WO | WO 2006/098969 A2 | 9/2006 |
| WO | WO 2007/002361 A2 | 1/2007 |
| WO | 2007 118323 | 10/2007 |
| WO | 2008 050200 | 5/2008 |
| WO | 2008 133867 | 11/2008 |

OTHER PUBLICATIONS

Cornelison, TL. Human papillomavirus genotype 16 vaccines for cervical cancer prophylaxis and treatment. Curr. Opin. Oncol. 2000, vol. 12(5), p. 466.*

Zellner, H. et al. Reaction of pyruvic acid with o-diamines. III. Synthesis of 2-(alpha-oxoalkyl)benzimidazoles. Monatshefte fuer Chemie. 1967, vol. 98, p. 650, table 2.*

Zellner, H. et al. Reaction of pyruvic acid with o-diamines. III. Synthesis of 2-(alpha-oxoalkyl)benzimidazoles. Monatshefte fuer Chemie. 1967, vol. 98, p. 650.*

Freshney, RI. Culture of Animal Cells: A Manual of Basic Technique. John Wiley and Sons. 2005, 5th Ed., p. 8.*

Dermer, GB. Another Anniversary for the War on Cancer. Bio/Technology. 1994, vol. 12, p. 320.*

Gray, LS. et al. T-type calcium channel blockers as new tools in cancer therapies. Eur. J. Physiol. 2014, vol. 466, p. 801.*

International Search Report Issued Aug. 30, 2011 in PCT/JP11/061913 Filed May 24, 2011.

Perez-Reyes, E., "Molecular Physiology of Low-Voltage-Activated T-type Calcium Channels," Physiol. Rev., vol. 83, No. 1, pp. 117 to 161, (2003).

Gray, L., et al., "The pharmacology and regulation of T type calcium channels: New opportunities for unique therapeutics for cancer," Cell Calcium, vol. 40, No. 2, pp. 115-120, (2006).

Vassort, G., et al., "Role of T-type $Ca^2+$ channels in the heart," Cell Calcium, vol. 40, No. 2, pp. 205 to 220, (2006).

Fareh, S., et al., "The T-type $Ca^{2+}$ Channel Blocker Mibefradil Prevents the Development of a Substrate for Atrial Fibrillation by Tachycardia-Induced Atrial Remodeling in Dogs," Journal of the American Heart Association, Vo. 100, No. 21, pp. 2191 to 2197, (1999).

Karam, H., et al., "Contrasting Effects of Selective T- and L-Type Calcium Channel Blockade on Glomerular Damage in DOCA Hypertensive Rats," Journal of the American Heart Association, vol. 34, pp. 673 to 678, (1999).

Extended European Search Report issued Jul. 4, 2014 in Patent Application No. 11786655.8.

Balázs Bognár, et al., "Synthesis of benzimidazoles condensed with, or linked to, nitroxides or heterocyclic N-oxides", Synthesis, No. 15, XP-055123538, 2008, pp. 2439-2445.

"AGN-PC-00L82X", Compound Summary for: CID 13162270, PubChem Compound, XP-002725886, 2007, pp. 1-5.

Office Action issued Oct. 10, 2014 in Chinese Patent Application No. 201180025463.8.

* cited by examiner

FUSED IMIDAZOLE DERIVATIVE

FIELD OF THE INVENTION

The present invention relates to a fused imidazole derivative showing an antagonistic effect against a T-type calcium channels, and a pharmaceutical agent containing the same.

BACKGROUND OF THE INVENTION

Intracellular calcium is an important factor causing a large variety of physiological responses such as neuronal excitement, muscle contraction, hormone secretion, fertilization, immune response, cell motility, and cell death; and the concentration is regulated by means of ion channels or pumps, such as voltage-dependent calcium channels and receptor-operated calcium channels. The voltage-dependent calcium channels are calcium channels which are opened and closed depending on the change of the potential difference between inside and outside of the cell, and exist on the cellular membrane of muscles or nerve cells. The voltage-dependent calcium channels are currently classified into L-type, T-type, N-type, P/Q-type, and R-type calcium channels, based on electrophysiological characteristics and pharmacological characteristics. Unlike L-type, N-type, P/Q-type and R-type calcium channels, which are classified as medium potential and high potential activated calcium channels in view of the voltage activation threshold, T-type calcium channels are activated at a potential that is close to the resting membrane potential. Therefore, the T-type calcium channels is believed to play a role as triggers for influx of calcium into the cell, and to participate in the pacemaker activity, production of low-threshold calcium spikes, and burst firing.

T-type calcium channels include three subtypes such as Cav3.1 (α1G), Cav3.2 (α1H) and Cav3.3 (α1I); and expression of the channel in, for example, the brain, nerve tissues, heart, kidneys, liver, pancreas, smooth muscles, testicles has been reported. It has been suggested that activation of the T-type calcium channels in these organs and tissue cells described above may cause intracellular calcium overload, and may participate in the onset and progress of various pathological conditions such as, for example, hypertension, tachyarrhythmia including atrial fibrillation, cardiac hypertrophy, cardiac failure, renal dysfunction, and cancers. Therefore, T-type calcium channel antagonistic drugs are believed to be effective in the treatment or prevention of these diseases (Non-Patent Documents 1 to 5).

One of known T-type calcium channel antagonistic drugs is mibefradil, however, this drug is not commercially available at present due to problems such as drug interaction. Furthermore, for example, Patent Document 1 discloses a 3,4-dihydroquinazoline derivative; Patent Document 2 discloses a quinazoline derivative; Patent Document 3 discloses a pyridylamide derivative; Patent Documents 4 and 5 disclose 3-fluoropiperidine derivatives; Patent Document 6 discloses an indole derivative; Patent Document 7 discloses an oxadiazole derivative; Patent Documents 8 and 9 disclose thiazole derivatives; Patent Document 10 discloses an isoxazole derivative; and Patent Document 11 discloses a 1,3-dioxoindole derivative, as the T-type calcium channel antagonistic drugs. However, these compounds have not been hitherto put to clinical use.

PRIOR ART DOCUMENTS

Patent Document

Patent Document 1: JP-A-2005-239708
Patent Document 2: JP-A-2008-533020
Patent Document 3: JP-A-2009-534320
Patent Document 4: JP-A-2008-546800
Patent Document 5: JP-A-2009-500340
Patent Document 6: WO2008/133867
Patent Document 7: WO2008/050200
Patent Document 8: JP-A-2009-521461
Patent Document 9: JP-A-2009-521471
Patent Document 10: WO2007/118323
Patent Document 11: JP-A-2007-297366

Non-Patent Document

Non-Patent Document 1: Physiological Reviews, USA, American Physiological Society, 2003, Vol. 83, No. 1, p. 117-161
Non-Patent Document 2: Cell Calcium, Netherlands, Elsevier, 2006, Vol. 40, No. 2, p. 115-120
Non-Patent Document 3: Cell Calcium, Netherlands, Elsevier, 2006, Vol. 40, No. 2, p. 205-220
Non-Patent Document 4: Circulation, USA, American Heart Association, 1999, Vol. 100, No. 21, p. 2191-2197
Non-Patent document 5: Hypertension, USA, American Heart Association, 1999, Vol. 34, p. 673-678

SUMMARY OF THE INVENTION

Problem to be Solved by the Invention

The object of the present invention is to provide a novel compound which shows an antagonistic effect against T-type calcium channels and is useful as a pharmaceutical product.

Means for Solving the Problem

Thus, the inventors of the present invention have synthesized various compounds and screened these compounds by utilizing the T-type calcium channel antagonistic effect as an indicator. Thus, the inventors found that a compound having an α-substituted benzyl group bound to the 2-position of a fused imidazole skeleton shows an excellent T-type calcium channel antagonistic effect and is useful as a prophylactic or therapeutic drug for various diseases such as hypertension and arrhythmia, thus completing the present invention.

That is, the present invention is to provide a compound represented by the following general formula (I), a pharmaceutically acceptable salt thereof, or a solvate thereof:

[Chemical formula I]

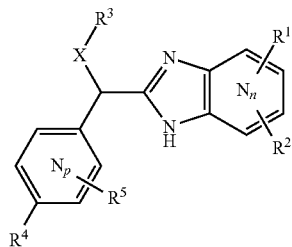

wherein ring $N_n$ represents a 6-membered fused aromatic ring which optionally has a nitrogen atom;
ring $N_p$ represents a 6-membered aromatic ring which optionally has a nitrogen atom;
n represents the number of nitrogen atoms contained in the 6-membered fused aromatic ring, and is 0, 1 or 2;

p represents the number of nitrogen atoms contained in the 6-membered aromatic ring, and is 0 or 1;

$R^1$ and $R^2$, which may be identical or different, each represents:
  (1) a hydrogen atom,
  (2) a halogen atom,
  (3) a hydroxyl group,
  (4) a cyano group,
  (5) a nitro group,
  (6) an optionally substituted $C_{1-6}$ alkyl group,
  (7) an optionally substituted $C_{1-6}$ alkoxy group,
  (8) —$SR^6$,
  (9) —$SO_2R^6$,
  (10) —$SO_2NR^6R^7$,
  (11) —(C=O)—$R^6$, or
  (12) an amino group;

$R^6$ and $R^7$, which may be identical or different, each represent an optionally substituted $C_{1-6}$ alkyl group;

$R^3$ represents:
  (1) a hydrogen atom,
  (2) an optionally substituted $C_{1-6}$ alkyl group,
  (3) —(C=O)—$R^8$, or
  (4) an optionally substituted aryl group or heteroaryl group;

$R^8$ represents an optionally substituted $C_{1-6}$ alkyl group;

X represents an oxygen atom, a sulfur atom, —$SO_2$—, or —N($R^9$)—;

$R^9$ represents an optionally substituted $C_{1-6}$ alkyl group, or may be combined together with $R^3$ and an adjacent nitrogen atom to form an optionally substituted non-aromatic heterocyclic ring;

$R^4$ represents:
  (1) a halo-$C_{1-6}$ alkyl group,
  (2) an optionally substituted $C_{2-6}$ alkenyl group,
  (3) a halo-$C_{1-6}$ alkoxy group,
  (4) an optionally substituted aralkyl group,
  (5) an optionally substituted aralkyloxy group,
  (6) an optionally substituted heteroaralkyloxy group,
  (7) an optionally substituted aryloxy-$C_{1-6}$ alkyl group,
  (8) —$SR^{10}$,
  (9) —$SO_2R^{10}$,
  (10) —$SO_2NR^{11}R^{12}$,
  (11) —$NR^{12}R^{13}$,
  (12) —(C=O)—$R^{13}$,
  (13) —(C=O)—$OR^{13}$,
  (14) —(C=O)—$NR^{12}R^{13}$, or
  (15) an optionally substituted aryl group or heteroaryl group;

$R^{10}$ represents a halo-$C_{1-6}$ alkyl group;

$R^{11}$ represents an optionally substituted aryl group or heteroaryl group;

$R^{12}$ represents a hydrogen atom or an optionally substituted $C_{1-6}$ alkyl group;

$R^{13}$ represents an optionally substituted aralkyl group;

$R^5$ represents:
  (1) a hydrogen atom,
  (2) a halogen atom,
  (3) a hydroxyl group,
  (4) a nitro group,
  (5) a cyano group,
  (6) an optionally substituted $C_{1-6}$ alkyl group, or
  (7) an optionally substituted $C_{1-6}$ alkoxy group; and $R^4$ and $R^5$ may be combined to form an optionally substituted aromatic ring or an optionally substituted non-aromatic ring;

with the proviso that when $R^4$ is an unsubstituted aralkyloxy group, and when n is 0, $XR^3$ is not OH.

Furthermore, the present invention is to provide a pharmaceutical agent containing the compound represented by the above general formula (I), a pharmaceutically acceptable salt thereof, or a solvate thereof.

Furthermore, the present invention is to provide a compound represented by the above general formula (I), which is used for the treatment or prevention of a disease for which a T-type calcium channel antagonistic effect is effective, a pharmaceutically acceptable salt thereof, or a solvate thereof.

Furthermore, the present invention is to provide the use of the compound represented by the above general formula (I), a pharmaceutically acceptable salt thereof, or a solvate thereof, for the manufacture of a therapeutic drug or a prophylactic drug for a disease for which a T-type calcium channel antagonistic effect is effective.

Furthermore, the present invention is to provide a method for treating or preventing a disease for which a T-type calcium channel antagonistic effect is effective, the method including administering an effective amount of a compound represented by the above general formula (I), a pharmaceutically acceptable salt thereof, or a solvate thereof.

Advantageous Effects of Invention

The compound of the present invention has an excellent T-type calcium channel antagonistic effect, is highly safe, and is useful as a prophylactic or therapeutic drug for various diseases on which T-type calcium channels have an action. Examples of the diseases that can be prevented or treated by a T-type calcium channel antagonistic effect include hypertension, atrial fibrillation, arrhythmia, cardiac hypertrophy, cardiac failure, renal dysfunction, and cancers.

MODES FOR CARRYING OUT THE INVENTION

In the general formula (I), the ring $N_n$ represents a 6-membered fused aromatic ring which optionally has a nitrogen atom, and n represents the number of nitrogen atoms contained in the 6-membered fused aromatic ring and is 0, 1 or 2. That is, examples of the following moiety:

[Chemical formula 2]

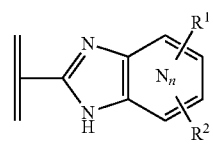

include the following structures:

[Chemical formula 3]

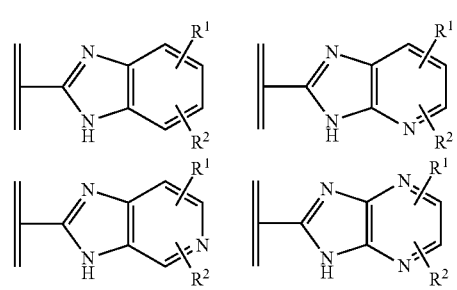

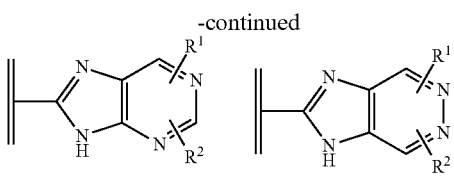

In the general formula (I), the ring $N_p$ represents a 6-membered aromatic ring which optionally has a nitrogen atom, and p represents the number of nitrogen atoms contained in the 6-membered aromatic ring, and is 0 or 1. That is, examples of the following moiety:

[Chemical formula 4]

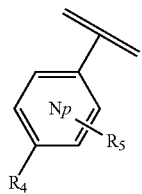

include the following structures:

[Chemical formula 5]

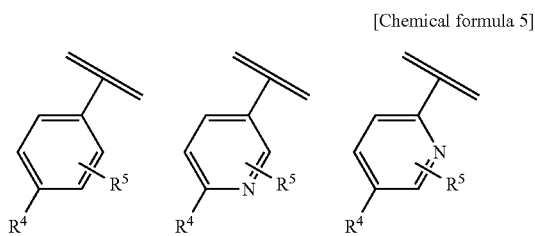

In the general formula (I), when $R^4$ and $R^5$ are combined to form an optionally substituted aromatic ring, or a non-aromatic ring, the aromatic ring or the non-aromatic ring may be, for example, a benzene ring, a pyrrole ring, a dioxole ring, or a hydrofuran ring. Examples of the substituent include a halogen atom, and an optionally substituted $C_{1-6}$ alkyl group.

In the present specification, examples of the "halogen atom" include a fluorine atom, a chlorine atom, a bromine atom and an iodine atom. In the general formula (I), the "halogen atom" represented by $R^1$, $R^2$ or $R^5$ is preferably a fluorine atom, a chlorine atom, or a bromine atom, and more preferably a fluorine atom or a chlorine atom.

The "$C_{1-6}$ alkyl group" as used in the present specification indicates a linear alkyl group having 1 to 6 carbon atoms, or a branched or cyclic alkyl group having 3 to 6 carbon atoms. Examples of the $C_{1-6}$ alkyl group include a methyl group, an ethyl group, an n-propyl group, an n-butyl group, an isopropyl group, an isobutyl group, a sec-butyl group, a tert-butyl group, an n-pentyl group, an n-hexyl group, a cyclopropyl group, a cyclobutyl group, a cyclopentyl group, and a cyclohexyl group. In the general formula (I), the "$C_{1-6}$ alkyl group" of the optionally substituted $C_{1-6}$ alkyl group as represented by $R^1$, $R^2$, $R^5$, $R^6$, $R^7$, $R^8$, $R^9$ or $R^{12}$ is preferably a $C_{1-4}$ alkyl group, and more preferably a methyl group, an ethyl group, an n-propyl group, or an isopropyl group. The "$C_{1-6}$ alkyl group" of the optionally substituted $C_{1-6}$ alkyl group as represented by $R^1$ or $R^2$ is particularly preferably a methyl group. The "$C_{1-6}$ alkyl group" of the optionally substituted $C_{1-6}$ alkyl group as represented by $R^5$ is particularly preferably an n-propyl group or a cyclopropyl group. The "$C_{1-6}$ alkyl group" of the optionally substituted $C_{1-6}$ alkyl group as represented by $R^6$ is particularly preferably a methyl group or an n-propyl group. The "$C_{1-6}$ alkyl group" of the optionally substituted $C_{1-6}$ alkyl group as represented by $R^9$ is particularly preferably a methyl group, an ethyl group, or an isopropyl group. The "$C_{1-6}$ alkyl group" of the optionally substituted $C_{1-6}$ alkyl group as represented by $R^3$ is preferably a methyl group, an ethyl group, an isopropyl group, an isobutyl group or a cyclohexyl group; and particularly preferably a methyl group, an ethyl group, or an isopropyl group.

The "$C_{2-6}$ alkenyl group" as used in the present specification indicates a linear alkenyl group having 2 to 6 carbon atoms, or a branched or cyclic alkenyl group having 3 to 6 carbon atoms. Examples of the $C_{2-6}$ alkenyl group include a vinyl group, a 1-propenyl group, a 2-propenyl group, an isopropenyl group, a 2-methyl-1-propenyl group, a 1-butenyl group, a 2-butenyl group, a 3-butenyl group, a 1-pentenyl group, a 2-pentenyl group, a 1-hexenyl group, a 2-hexenyl group, a 1-cyclohexenyl group, a 2-cyclohexenyl group, and a 3-cyclohexenyl group. In the general formula (I), the "$C_{2-6}$ alkenyl group" of the optionally substituted $C_{2-6}$ alkenyl group as represented by $R^4$ is preferably a $C_{2-4}$ alkenyl group; and more preferably a vinyl group, a 1-propenyl group, or a 2-propenyl group.

The "aryl group" as used in the present specification indicates a monocyclic or polycyclic aromatic group having 6 to 10 carbon atoms. Examples of the aryl group include a phenyl group, a 1-naphthyl group, and a 2-naphthyl group. In the general formula (I), the "aryl group" of the optionally substituted aryl group as represented by $R^3$ or $R^4$ is preferably a phenyl group.

The "heteroaryl group" as used in the present specification indicates a monocyclic or polycyclic aromatic group containing one to three of oxygen atoms, nitrogen atoms or sulfur atoms. Examples of the heteroaryl group include a pyrrolyl group, a furyl group, a thienyl group, a pyrazolyl group, an imidazolyl group, an oxazolyl group, an isoxazolyl group, a thiazolyl group, an isothiazolyl group, an oxadiazolyl group, a thiadiazolyl group, a triazolyl group, a pyridyl group, a pyridazinyl group, a pyrimidinyl group, a pyrazinyl group, a quinolyl group, an isoquinolyl group, a benzimidazolyl group, an indolyl group, a purinyl group, a benzisoxazolyl group, a benzoxazolyl group, a benzisothiazolyl group, and a benzothiazolyl group. In the general formula (I), the "heteroaryl group" of the optionally substituted heteroaryl group as represented by $R^3$ or $R^4$ is preferably a 5-membered or 6-membered monocyclic heteroaryl group, and more preferably a pyridyl group.

The "$C_{1-6}$ alkoxy group" as used in the present specification indicates a group in which one hydrogen atom of the "$C_{1-6}$ alkyl group" described above has been substituted by an oxygen atom. Examples of the $C_{1-6}$ alkoxy group include a methoxy group, an ethoxy group, an n-propoxy group, an isopropoxy group, an n-butoxy group, an isobutoxy group, a tert-butoxy group, an n-pentoxy group, an n-hexoxy group, a cyclopropoxy group, a cyclopropylmethoxy group, a cyclobutoxy group, a cyclopentoxy group, and a cyclohexoxy group. In the general formula (I), the "$C_{1-6}$ alkoxy group" of the optionally substituted $C_{1-6}$ alkoxy group as represented by $R^1$, $R^2$ or $R^5$ is preferably a $C_{1-4}$ alkoxy group, and more preferably a methoxy group, an ethoxy group, an n-propoxy group, or an isopropoxy group.

The "halo-$C_{1-6}$ alkyl group" as used in the present specification indicates a group in which one or more hydrogen atoms of the "$C_{1-6}$ alkyl group" described above have been substituted by halogen atoms. Examples of the halo-$C_{1-6}$ alkyl group include a chloromethyl group, a dichloromethyl group, a trichloromethyl group, a fluoromethyl group, a difluoromethyl group, a trifluoromethyl group, a bromomethyl group, a dibromomethyl group, a tribromomethyl group, a 2-chloroethyl group, a 2,2-dichloroethyl group, a 2,2,2-trichloroethyl group, a 2-fluoroethyl group, a 2,2-difluoroethyl group, a 2,2,2-trifluoroethyl group, a 1,1,2,2-tetrafluoroethyl group, a pentafluoroethyl group, a 2-bromoethyl group, a 2,2,2-tribromoethyl group, a 3,3,3-trichloropropyl group, a 3,3,3-trifluoropropyl group, a 3,3,3-tribromopropyl group, a 4,4,4-trichlorobutyl group, a 4,4,4-trifluorobutyl group, a 5,5,5-trifluoropentyl group, a 5,5,5-trichloropentyl group, a 5-bromo-5,5-difluoropentyl group, a 6,6,6-trifluorohexyl group, a 6,6,6-trichlorohexyl group, a 6-bromo-6,6-difluorohexyl, and a 4,4-difluorocyclohexyl group. In the general formula (I), the "halo-$C_{1-6}$ alkyl group" represented by $R^4$ or $R^{10}$ is preferably a $C_{1-4}$ alkyl group substituted with one or more fluorine atoms, and more preferably a 2-fluoroethyl group, a trifluoromethyl group, a 2,2,2-trifluoroethyl group, or a 3,3,3-trifluoropropyl group.

The "halo-$C_{1-6}$ alkoxy group" as used in the present specification indicates a group in which one or more hydrogen atoms of the "$C_{1-6}$ alkoxy group" described above have been substituted by halogen atoms. Examples of the halo-$C_{1-4}$ alkoxy group include a chloromethoxy group, a dichloromethoxy, a trichloromethoxy group, a fluoromethoxy group, a difluoromethoxy group, a trifluoromethoxy group, a bromomethoxy group, a dibromomethoxy group, a tribromomethoxy group, a 2-chloroethoxy group, a 2,2-dichloroethoxy group, a 2,2,2-trichloroethoxy group, a 2-fluoroethoxy group, a 2,2-difluoroethoxy group, a 2,2,2-trifluoroethoxy group, a 1,1,2,2-tetrafluoroethoxy group, a 1,1,2,2,2-pentafluoroethoxy group, a 3,3,3-trichloropropoxy group, a 3,3,3-trifluoropropoxy group, a 3,3,3-tribromopropoxy group, a 4,4,4-trichlorobutoxy group, a 4,4,4-trifluorobutoxy group, a 5,5,5-trifluoropentoxy group, a 5,5,5-trichloropentoxy group, a 5-bromo-5,5-difluoropentoxy group, a 6,6,6-trifluorohexoxy group, a 6,6,6-trichlorohexoxy group, a 6-bromo-6,6-difluorohexoxy group, and a 4,4-difluorocyclohexoxy group. In the general formula (I), the "halo-$C_{1-6}$ alkoxy group" represented by $R^1$, $R^2$ or $R^4$ is preferably a $C_{1-4}$ alkoxy group substituted with one or more fluorine atoms, and more preferably a difluoromethoxy group, a trifluoromethoxy group, a 2,2,2-trifluoroethoxy group, or a 3,3,3-trifluoropropoxy group.

The "aryloxy group" as used in the present specification indicates a group in which one hydrogen atom of the "aryl group" described above has been substituted by an oxygen atom. Examples of the aryloxy group include a phenoxy group, a 1-naphthoxy group, and a 2-naphthoxy group.

The "heteroaryloxy group" as used in the present specification indicates a group in which one hydrogen atom of a cyclic carbon atom of the "heteroaryl group" described above has been substituted by an oxygen atom. Examples of the heteroaryloxy group include a 2-pyridyloxy group, a 3-pyridyloxy group, a 2-imidazolyloxy group, a 2-pyrimidinyloxy group, and a 1,2,4-triazol-5-yloxy group.

The "aryloxy-$C_{1-6}$ alkyl group" as used in the present specification indicates a group in which one hydrogen atom of the "$C_{1-6}$ alkyl group" described above has been substituted by an aryloxy group. Examples of the aryloxy-$C_{1-6}$ alkyl group include a phenoxymethyl group, a phenoxyethyl group, a phenoxypropyl group, a phenoxybutyl group, a phenoxypentyl group, and a phenoxyhexyl group. In the general formula (I), the "aryloxy-$C_{1-6}$ alkyl group" of the optionally substituted aryloxy-$C_{1-6}$ alkyl group as represented by $R^4$ is preferably a phenyloxy-$C_{1-4}$ alkyl group, and more preferably a phenoxymethyl group or a phenoxyethyl group.

The "aralkyl group" as used in the present specification indicates a group in which one hydrogen atom of the "$C_{1-6}$ alkyl group" described above has been substituted by an aryl group. Examples of the aralkyl group include a benzyl group, a phenethyl group, a diphenylmethyl group, a 1-naphthylmethyl group, a 2-naphthylmethyl group, a 2,2-diphenylethyl group, a naphthylethyl group, a 3-phenylpropyl group, a 4-phenylbutyl group, and a 5-phenylpentyl group. In the general formula (I), the "aralkyl group" of the optionally substituted aralkyl group as represented by $R^{13}$ is preferably a phenyl-$C_{1-6}$ alkyl group or a naphthyl-$C_{1-6}$ alkyl group, and more preferably a benzyl group or a phenethyl group.

The "aralkyloxy group" as used in the present specification indicates a group in which one hydrogen atom of the "$C_{1-6}$ alkoxy group" described above has been substituted by an aryl group. Examples of the aralkyloxy group include a benzyloxy group and a phenethyloxy group. In the general formula (I), the "aralkyloxy group" of the optionally substituted aralkyloxy group as represented by $R^4$ is preferably a phenyl-$C_{1-6}$ alkyloxy group, and more preferably a benzyloxy group.

The "heteroaralkyloxy group" as used in the present specification indicates a group in which one hydrogen atom of the "$C_{1-6}$ alkoxy group" described above has been substituted by a heteroaryl group. Examples of the heteroaralkyloxy group include a pyridyl-$C_{1-6}$ alkyloxy group. In the general formula (I), the "heteroaralkyloxy group" of the optionally substituted heteroaralkyloxy group as represented by $R^4$ is preferably a pyridylmethyloxy group or a pyridylethyloxy group, and more preferably a 3-pyridylmethyloxy group, a 3-pyridylethyloxy group, a 2-pyridylmethyloxy group, or a 2-pyridylethyloxy group.

The "non-aromatic heterocyclic ring" as used in the present specification indicates a non-aromatic heterocyclic ring which is a 3-membered to 10-membered monocyclic, bicyclic or tricyclic ring containing at least one atom selected from, for example, oxygen atom, nitrogen atom, or sulfur atom. Examples of the non-aromatic heterocyclic ring include an azetidine ring, a pyrrolidine ring, a piperidine ring, a piperazine ring, a hexamethyleneimine ring, a heptamethyleneimine ring, a homopiperazine ring, a 2,5-diazabicyclo[2.2.1]heptane ring, a 1,6-diazepane ring, a 2,5-diazabicyclo[2.2.2]octane ring, a 1,6-diazabicyclo[3.2.1]octane ring, a tetrahydrofuran ring, a tetrahydropyrane ring, and a morpholine ring. In the general formula (I), the "non-aromatic heterocyclic ring" in the case where X is $NR^9$ and $R^9$ is combined together with $R^3$ and the adjacent nitrogen atom to form an optionally substituted non-aromatic heterocyclic ring, is preferably a morpholine ring, a pyrrolidine ring or a piperazine ring, and more preferably a morpholine ring or a pyrrolidine ring.

The expression "optionally substituted" as used in the present specification means either "unsubstituted" or having one to five, and preferably one to three, identical or different substituents at substitutable positions. According to the present specification, when, for example, the $C_{1-6}$ alkyl group, $C_{2-6}$ alkenyl group, aryl group, heteroaryl group, aryloxy group, heteroaryloxy group, $C_{1-6}$ alkoxy group, aralkyl group, aralkyloxy group, heteroaralkyloxy group, aryloxy-$C_{1-6}$ alkyl group optionally have substituents, examples of the substituents include a halogen atom, a hydroxyl group, a cyano group, a nitro group, a $C_{1-6}$ alkyl group, a $C_{1-6}$ alkoxy group, an acyl group, a formyl group, a carboxyl group, a $C_{1-6}$ alkylcarbonylamino group, a $C_{1-6}$ alkoxycarbonyl group, a carbamoyl group, a sulfamoyl group, a $C_{1-6}$ alkylsulfanyl group, a $C_{1-6}$ alkylsulfonyl group, an amino group, a $C_{1-6}$ alkylamino group, a $C_{1-6}$ dialkylamino group, an aryl group, a heteroaryl group, and a non-aromatic heterocyclic group. These may be further substituted.

The $C_{1-6}$ alkyl group, $C_{2-6}$ alkenyl group and $C_{1-6}$ alkoxy group which are substituted, preferably have one to five, and more preferably one to three, substituents selected from halogen atoms, cyano groups, hydroxyl groups and $C_{1-6}$ alkoxy groups.

The optionally substituted $C_{1-6}$ alkyl group as represented by $R^1$ or $R^2$ is preferably unsubstituted or is preferably a $C_{1-6}$ alkyl group substituted with one to five halogen atoms, and is particularly preferably an unsubstituted $C_{1-6}$ alkyl group. The optionally substituted $C_{1-6}$ alkyl group as represented by $R^3$ is preferably unsubstituted or is preferably a $C_{1-6}$ alkyl group substituted with one to five halogen atoms, $C_{1-6}$ alkoxy groups, aryl groups or hydroxyl groups, and is particularly preferably an unsubstituted $C_{1-6}$ alkyl group. The optionally substituted $C_{1-6}$ alkoxy group as represented by $R^1$ or $R^2$ is preferably unsubstituted or is preferably a $C_{1-6}$ alkoxy group substituted with one to five halogen atoms, and is particularly preferably an unsubstituted $C_{1-6}$ alkoxy group. As for others, unsubstituted groups are preferred.

The aryl group, heteroaryl group, aryloxy group, heteroaryloxy group, aralkyl group, heteroaralkyl group, aralkyloxy group, heteroaralkyloxy group and aryloxy-$C_{1-6}$ alkyl group which are substituted preferably have one to five, and more preferably one to three, substituents selected from $C_{1-6}$ alkyl groups, halogen atoms, cyano groups, hydroxyl groups and $C_{1-6}$ alkoxy groups, on the aromatic ring.

The optionally substituted aralkyloxy group or heteroaralkyloxy group as represented by $R^4$ is preferably unsubstituted or is preferably substituted with one to three halogen atoms, $C_{1-6}$ alkyl groups, $C_{1-6}$ alkoxy groups, halo-$C_{1-6}$ alkyl groups or halo-$C_{1-6}$ alkoxy groups on the aromatic ring. As for others, unsubstituted groups are preferred.

More preferred examples in relation to the general formula (I) of the present invention include the following items <1> to <9> and any combinations thereof.

<1> n is preferably 0 or 1, and more preferably 0. Accordingly, the $N_n$ ring is preferably a benzene ring or a pyridine ring, and more preferably a benzene ring.

<2> p is preferably 0. Accordingly, the $N_p$ ring is preferably a benzene ring.

<3> $R^1$ and $R^2$ are preferably such that $R^2$ is a hydrogen atom, and $R^1$ is a substituent other than a hydrogen atom.

$R^1$ is preferably (1) a halogen atom, (2) an optionally substituted $C_{1-6}$ alkyl group, or (3) an optionally substituted $C_{1-6}$ alkoxy group; more preferably (1) a fluorine atom, (2) a chlorine atom, (3) a $C_{1-6}$ alkyl group, (4) a $C_{1-6}$ alkoxy group, or (5) a halo-$C_{1-6}$ alkoxy group; and particularly preferably a fluorine atom.

<4> When $R^2$ is a hydrogen atom and $R^1$ is other than a hydrogen atom, a fused heterocyclic ring containing $R^1$ and Nn is preferably represented by the following formula:

[Chemical formuoa 6]

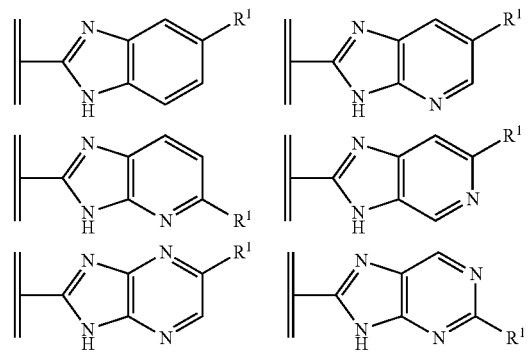

Particularly, it is preferable that n be 0 or 1, and the fused heterocyclic ring containing $R^1$ and Nn be represented by the following formula:

[Chemical formula 7]

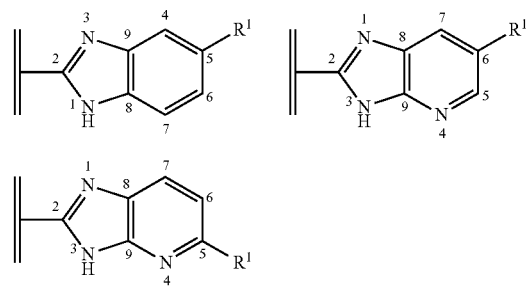

<5> $R^3$ is preferably (1) a hydrogen atom, (2) an optionally substituted $C_{1-6}$ alkyl group, or (3) an optionally substituted aryl group or heteroaryl group;

more preferably (1) a hydrogen atom, (2) a $C_{1-6}$ alkyl group, (3) a halo-$C_{1-6}$ alkyl group, or (4) an aryl group or a heteroaryl group; and particularly preferably, a hydrogen atom, a methyl group, an ethyl group, a 2-fluoroethyl group, or an isopropyl group.

<6> X is preferably an oxygen atom, —$SO_2$— or —N($R^9$)—; and more preferably an oxygen atom.

<7> $R^4$ is preferably (1) a halo-$C_{1-6}$ alkyl group, (2) a halo-$C_{1-6}$ alkoxy group, (3) an optionally substituted aralkyl group, (4) an optionally substituted aralkyloxy group, (5) —$SR^{10}$, or (6) an optionally substituted aryl group or heteroaryl group; more preferably (1) a halo-$C_{1-4}$ alkyl group, (2) a halo-$C_{1-4}$ alkoxy group, (3) an optionally substituted aralkyloxy group, or (4) —$SR^{10}$;

even more preferably (1) a $C_{1-4}$ alkyl group substituted with a fluorine atom, (2) a $C_{1-4}$ alkoxy group substituted with a fluorine atom, or (3) an aralkyloxy group substituted with a halogen atom; and particularly preferably a trifluoromethoxy group.

<8> $R^5$ is preferably (1) a hydrogen atom, or (2) a halogen atom; and more preferably a hydrogen atom.

<9> It is also preferable that $R^4$ and $R^5$ be combined to form an optionally substituted benzene ring or dioxole ring.

Specific examples of particularly preferred compounds of the general formula (I) of the present invention include the following compounds:

(5-fluoro-1H-benzimidazol-2-yl)-(4-trifluoromethoxyphenyl)methanol;
(5-fluoro-1H-benzimidazol-2-yl)-(4-trifluoromethylsulfanylphenyl)methanol;
(5-fluoro-1H-benzimidazol-2-yl)-(4-trifluoromethylphenyl)methanol;
(5-fluoro-1H-benzimidazol-2-yl)-[3-fluoro-4-(trifluoromethyl)phenyl]methanol;
2-[ethoxy(4-trifluoromethylphenyl)methyl]-5-fluoro-1H-benzimidazole;
(5-fluoro-1H-benzimidazol-2-yl)-[4-(1,1,2,2-tetrafluoroethoxy)phenyl]methanol;
(5-fluoro-1H-benzimidazol-2-yl)-(naphthalen-2-yl)methanol;
(2,2-difluorobenzo[1,3]dioxol-5-yl)-(5-fluoro-1H-benzimidazol-2-yl)methanol;
5-fluoro-2-[isopropoxy(4-trifluoromethoxyphenyl)methyl]-1H-benzimidazole;
5-fluoro-2-[(2-methoxyethoxy)-(4-trifluoromethoxyphenyl)methyl]-1H-benzimidazole;
(6-chloro-3H-imidazo[4,5-b]pyridin-2-yl)-(4-trifluoromethoxyphenyl)methanol;
(6-fluoro-3H-imidazo[4,5-b]pyridin-2-yl)-[4-(4-methylbenzyloxy)phenyl]methanol;
6-chloro-2-[ethoxy(4-trifluoromethoxyphenyl)methyl]-3H-imidazo[4,5-b]pyridine;
6-chloro-2-{ethoxy[4-(4-methylbenzyloxy)phenyl]methyl}-3H-imidazo[4,5-b]pyridine;
2-{ethoxy[4-(4-methylbenzyloxy)phenyl]methyl}-6-fluoro-3H-imidazo[4,5-b]pyridine;
6-chloro-2-{ethoxy[4-(4-fluorobenzyloxy)phenyl]methyl}-3H-imidazo[4,5-b]pyridine;
2-{ethoxy[4-(4-fluorobenzyloxy)phenyl]methyl}-6-fluoro-3H-imidazo[4,5-b]pyridine;
2-{[4-(2,5-difluorobenzyloxy)phenyl]ethoxymethyl}-5-ethoxy-1H-benzimidazole;
5-chloro-2-{[4-(2,5-difluorobenzyloxy)phenyl]ethoxymethyl}-1H-benzimidazole;
2-{[4-(2,5-difluorobenzyloxy)phenyl]ethoxymethyl}-5-trifluoromethyl-1H-benzimidazole;
2-{[4-(2,5-difluorobenzyloxy)phenyl]ethoxymethyl}-5-methoxy-1H-benzimidazole;
5-ethoxy-2-[ethoxy(4-trifluoromethoxyphenyl)methyl]-1H-benzimidazole;
2-[ethoxy(4-trifluoromethoxyphenyl)methyl]-5-fluoro-1H-benzimidazole;
5-ethoxy-2-[methoxy(4-trifluoromethoxyphenyl)methyl]-1H-benzimidazole;
2-{[4-(2,5-difluorobenzyloxy)phenyl]ethoxymethyl}-5-methyl-1H-benzimidazole;
2-[ethoxy(4-trifluoromethoxyphenyl)methyl]-5-methoxy-1H-benzimidazole;
5-chloro-2-[methoxy(4-trifluoromethoxyphenyl)methyl]-1H-benzimidazole;
5-fluoro-2-[methoxy(4-trifluoromethoxyphenyl)methyl]-1H-benzimidazole;
5-ethoxy-2-[ethoxy(4-trifluoromethylsulfanylphenyl)methyl]-1H-benzimidazole;
5-ethoxy-2-{ethoxy[4-(4-methylbenzyloxy)phenyl]methyl}-1H-benzimidazole;
2-{[4-(2,4-difluorobenzyloxy)phenyl]ethoxymethyl}-5-ethoxy-1H-benzimidazole;
(5-fluoro-1H-benzimidazol-2-yl)-[3-fluoro-4-(trifluoromethoxy)phenyl]methanol;
[3-bromo-4-(trifluoromethoxy)phenyl]-(5-fluoro-1H-benzimidazol-2-yl)methanol;
2-[ethoxy(3-fluoro-4-trifluoromethoxyphenyl)methyl]-5-fluoro-1H-benzimidazole;
(5-fluoro-1H-benzimidazol-2-yl)-[4-(2,2,2-trifluoroethoxy)phenyl]methanol;
5-fluoro-2-{methoxy[4-(2,2,2-trifluoroethoxy)phenyl]methyl}-1H-benzimidazole;
2-{ethoxy[4-(2,2,2-trifluoroethoxy)phenyl]methyl}-5-fluoro-1H-benzimidazole;
2-[(2,2-difluorobenzo[1,3]dioxol-5-yl)ethoxymethyl]-5-fluoro-1H-benzimidazole;
2-[(2,2-difluorobenzo[1,3]dioxol-5-yl)methoxymethyl]-5-fluoro-1H-benzimidazole;
(5-nitro-1H-benzimidazol-2-yl)-(4-trifluoromethoxyphenyl)methanol;
5-chloro-3H-imidazo[4,5-b]pyridin-2-yl)-(4-trifluoromethoxyphenyl)methanol;
(5-propylsulfanyl-1H-benzimidazol-2-yl)-(4-trifluoromethoxyphenyl)methanol;
(6-chloro-3H-imidazo[4,5-b]pyridin-2-yl)-(2,2-difluorobenzo[1,3]dioxol-5-yl)methanol;
2-{[4-(2,5-difluorobenzyloxy)phenyl]ethoxymethyl}-5-fluoro-1H-benzimidazole;
2-{[4-(2,5-difluorobenzyloxy)phenyl]ethoxymethyl}-5-nitro-1H-benzimidazole;
5-ethoxy-2-{ethoxy[4-(4-fluorobenzyloxy)phenyl]methyl}-1H-benzimidazole;
5-ethoxy-2-{ethoxy[4-(3-fluorobenzyloxy)phenyl]methyl}-1H-benzimidazole;
5-ethoxy-2-{ethoxy[4-(2-fluorobenzyloxy)phenyl]methyl}-1H-benzimidazole;
2-{[4-(3,5-dimethoxybenzyloxy)phenyl]ethoxymethyl}-5-ethoxy-1H-benzimidazole;
5-ethoxy-2-{ethoxy[4-(4-trifluoromethoxybenzyloxy)phenyl]methyl}-1H-benzimidazole;
(5-bromo-1H-benzimidazol-2-yl)-(4-trifluoromethoxyphenyl)methanol;
5-bromo-2-[ethoxy(4-trifluoromethoxyphenyl)methyl]-1H-benzimidazole;
2-[hydroxy(4-trifluoromethoxyphenyl)methyl]-1H-benzimidazole-5-carbonitrile;
2-[ethoxy(4-trifluoromethoxyphenyl)methyl]-1H-benzimidazole-5-carbonitrile;
6-chloro-2-[ethoxy(4-trifluoromethoxyphenyl)methyl]-4-fluoro-1H-benzimidazole;
6-chloro-2-[ethoxy(4-trifluoromethoxyphenyl)methyl]-1H-benzimidazol-4-ylamine;
2-[ethoxy(4-trifluoromethoxyphenyl)methyl]-5,6-difluoro-1H-benzimidazole;
2-[ethoxy(4-trifluoromethoxyphenyl)methyl]-6-fluoro-3H-imidazo[4,5-b]pyridine;
6-bromo-2-[ethoxy(4-trifluoromethoxyphenyl)methyl]-3H-imidazo[4,5-b]pyridine;
2-[ethoxy(4-trifluoromethoxyphenyl)methyl]-5-trifluoromethoxy-1H-benzimidazole;

2-[ethoxy(4-trifluoromethoxyphenyl)methyl]-5-trifluoromethyl-1H-benzimidazole;
2-[ethoxy(4-trifluoromethoxyphenyl)methyl]-4-fluoro-1H-benzimidazole;
5-difluoromethoxy-2-[ethoxy(4-trifluoromethoxyphenyl)methyl]-1H-benzimidazole;
2-[(3-bromo-4-trifluoromethoxyphenyl)methoxymethyl]-5-fluoro-1H-benzimidazole;
2-[(3-bromo-4-trifluoromethoxyphenyl)methoxymethyl]-1H-benzimidazole;
2-[(3-bromo-4-trifluoromethoxyphenyl)methoxymethyl]-5-methoxy-1H-benzimidazole;
2-[(3-bromo-4-trifluoromethoxyphenyl)methoxymethyl]-5-ethoxy-1H-benzimidazole;
5-difluoromethoxy-2-[ethoxy(4-trifluoromethylphenyl)methyl]-1H-benzimidazole;
5-difluoromethoxy-2-[methoxy(4-trifluoromethylphenyl)methyl]-1H-benzimidazole;
(1H-benzimidazol-2-yl)-(4-trifluoromethoxyphenyl)methanol;
(5-difluoromethoxy-1H-benzimidazol-2-yl)-(4-difluoromethoxyphenyl)methanol;
(5-difluoromethoxy-1H-benzimidazol-2-yl)-[4-(2,2,2-trifluoroethoxy)phenyl]methanol;
(5-difluoromethoxy-1H-benzimidazol-2-yl)-(4-trifluoromethylphenyl)methanol;
(3-chloro-4-trifluoromethoxyphenyl)-(5-fluoro-1H-benzimidazol-2-yl)methanol;
(1H-benzimidazol-2-yl)-(3-chloro-4-trifluoromethoxyphenyl)methanol;
(3-chloro-4-trifluoromethoxyphenyl)-(5-methoxy-1H-benzimidazol-2-yl)methanol;
2-[methoxy(4-trifluoromethoxyphenyl)methyl]-1H-benzimidazole;
2-[ethoxy(4-trifluoromethoxyphenyl)methyl]-1H-benzimidazole;
2-[propoxy(4-trifluoromethoxyphenyl)methyl]-1H-benzimidazole;
2-[isopropoxy(4-trifluoromethoxyphenyl)methyl]-1H-benzimidazole;
2-[(3-chloro-4-trifluoromethoxyphenyl)ethoxymethyl]-5-fluoro-1H-benzimidazole;
2-[(3-chloro-4-trifluoromethoxyphenyl)ethoxymethyl]-1H-benzimidazole;
2-[(3-chloro-4-trifluoromethoxyphenyl)ethoxymethyl]-5-methoxy-1H-benzimidazole;
(5-methoxy-1H-benzimidazol-2-yl)-(4-trifluoromethoxyphenyl)methanol;
2-[isopropoxy(4-trifluoromethoxyphenyl)methyl]-3H-imidazo[4,5-b]pyridine;
(5-chloro-1H-benzimidazol-2-yl)-(4-trifluoromethoxyphenyl)methanol;
(5-difluoromethoxy-1H-benzimidazol-2-yl)-(4-trifluoromethoxyphenyl)methanol;
2-[hydroxy(4-trifluoromethoxyphenyl)methyl]-1H-benzimidazol-5-ol;
(6-chloro-4-fluoro-1H-benzimidazol-2-yl)-(4-trifluoromethoxyphenyl)methanol;
(5-trifluoromethoxy-1H-benzimidazol-2-yl)-(4-trifluoromethoxyphenyl)methanol;
(4-trifluoromethoxyphenyl)-(5-trifluoromethyl-1H-benzimidazol-2-yl)methanol;
(4-fluoro-1H-benzimidazol-2-yl)-(4-trifluoromethoxyphenyl)methanol;
(1H-benzimidazol-2-yl)-(3-bromo-4-trifluoromethoxyphenyl)methanol;
(3-bromo-4-trifluoromethoxyphenyl)-(5-methoxy-1H-benzimidazol-2-yl)methanol;
(3-bromo-4-trifluoromethoxyphenyl)-(5-ethoxy-1H-benzimidazol-2-yl)methanol;
(5,6-difluoro-1H-benzimidazol-2-yl)-(4-trifluoromethoxyphenyl)methanol;
(5-fluoro-1H-benzimidazol-2-yl)-(3-isopropyl-4-trifluoromethoxyphenyl)methanol;
(6-fluoro-3H-imidazo[4,5-b]pyridin-2-yl)-(4-trifluoromethoxyphenyl)methanol;
(6-bromo-3H-imidazo[4,5-b]pyridin-2-yl)-(4-trifluoromethoxyphenyl)methanol;
5-fluoro-2-[(2-fluoroethoxy)-(4-trifluoromethoxyphenyl)methyl]-1H-benzimidazole;
2-[(5-fluoro-1H-benzimidazol-2-yl)-(4-trifluoromethoxyphenyl)methoxyl]ethanol;
5-fluoro-2-[propoxy(4-trifluoromethoxyphenyl)methyl]-1H-benzimidazole;
2-[isopropoxy(4-trifluoromethoxyphenyl)methyl]-5-methoxy-1H-benzimidazole;
5-ethoxy-2-[isopropoxy(4-trifluoromethoxyphenyl)methyl]-1H-benzimidazole;
5-chloro-2-[ethoxy(4-trifluoromethoxyphenyl)methyl]-1H-benzimidazole;
5-fluoro-2-[methoxy(4-trifluoromethylphenyl)methyl]-1H-benzimidazole;
5-[(5-fluoro-1H-benzimidazol-2-yl)methoxymethyl]-2-trifluoromethoxybenzonitrile; and
2-[(3-cyclopropyl-4-trifluoromethoxyphenyl)methoxymethyl]-5-fluoro-1H-benzimidazole.

According to the present specification, the structural formula of a compound may represent a certain isomer for convenience; however, the present invention includes all of isomers such as geometric isomers, optical isomers based on asymmetric carbon atoms, sterical isomers, and tautomeric isomers, and isomeric mixtures which occur as a result of the structure of the compound. Thus, the structural formula of a compound is not intended to be limited to the formula described for convenience, and may be any one of the isomers or may be a mixture. In particular, the compound of the present invention has an asymmetric carbon atom in the molecule and may be an optical isomer and racemate; however, the compound is not intended to be limited to any one of them in the present invention, and all are included.

Furthermore, the present invention includes pharmaceutically acceptable salts of the compound (I) of the present invention. Specific examples thereof include acid addition salts with inorganic acids, such as hydrochloride, hydrobromide, hydroiodide, sulfate, nitrate and phosphate, acid addition salts with organic acids, such as formate, acetate, trichloroacetate, trifluoroacetate, propionate, oxalate, malonate, succinate, fumarate, maleate, lactate, malate, tartrate, citrate, methanesulfonate, ethanesulfonate, benzenesulfonate, p-toluenesulfonate (4-methylbenzenesulfonate), aspartate and glutamate; salts with inorganic bases, such as sodium salts, potassium salts, magnesium salts, calcium salts, and aluminum salts; salts with organic bases, such as methylamine, ethylamine, ethanolamine, lysine, and ornithine; and ammonium salts.

Furthermore, the present invention also includes pharmaceutically acceptable prodrugs of the compound (I) of the present invention. A pharmaceutically acceptable prodrug means a compound which is subjected to enzymatic oxidation, reduction or hydrolysis under the physiological conditions in a living organism and is converted to the compound (I) of the present invention. Examples of a group that forms a prodrug include the groups described in Prog. Med., 5, 2157-

2161 (1985), or "Iyakuhin no Kaihatsu (Development of Pharmaceutical Products)" (Hirokawa Shoten Co., 1990) Vol. 7, Molecular Design, 163-198.

Furthermore, the present invention also includes hydrates, various solvates and crystal polymorphisms of the compound (I) of the present invention and pharmaceutically acceptable salts thereof. However, similarly, there are no limitations, and the present invention may include both any one single crystal form and a mixture of crystal forms.

Furthermore, the present invention includes compounds obtained by labeling the compound (I) of the present invention with, for example, an isotope (for example, $^2$H, $^3$H, $^{14}$C, $^{35}$S or $^{125}$I).

The compound of the present invention and a pharmaceutically acceptable salt thereof can be produced by utilizing the features based on the type of the basic skeleton or a substituent thereof, and applying various synthesis methods that are known per se in connection with the introduction of substituents or conversion of functional groups. With regard to the introduction of substituents or conversion of functional groups, when a reactive substituent such as an amino group, a hydroxyl group or a carboxyl group is present, a desired compound may be obtained by introducing a protective group to the relevant substituent as necessary, and removing the protective group after a target reaction is completed. The selection of the protective group, introduction of the protective group, and removal of the protective group can be appropriately selected from, for example, the methods described in Greene and Wuts, "Protective Groups in Organic Synthesis (Third Edition)" and carried out.

Examples of the method for producing a fused imidazole derivative of the present invention include the following methods, but the production method for the compound of the present invention is not intended to be limited to these methods.

Production Method 1

[Chemical formula 8]

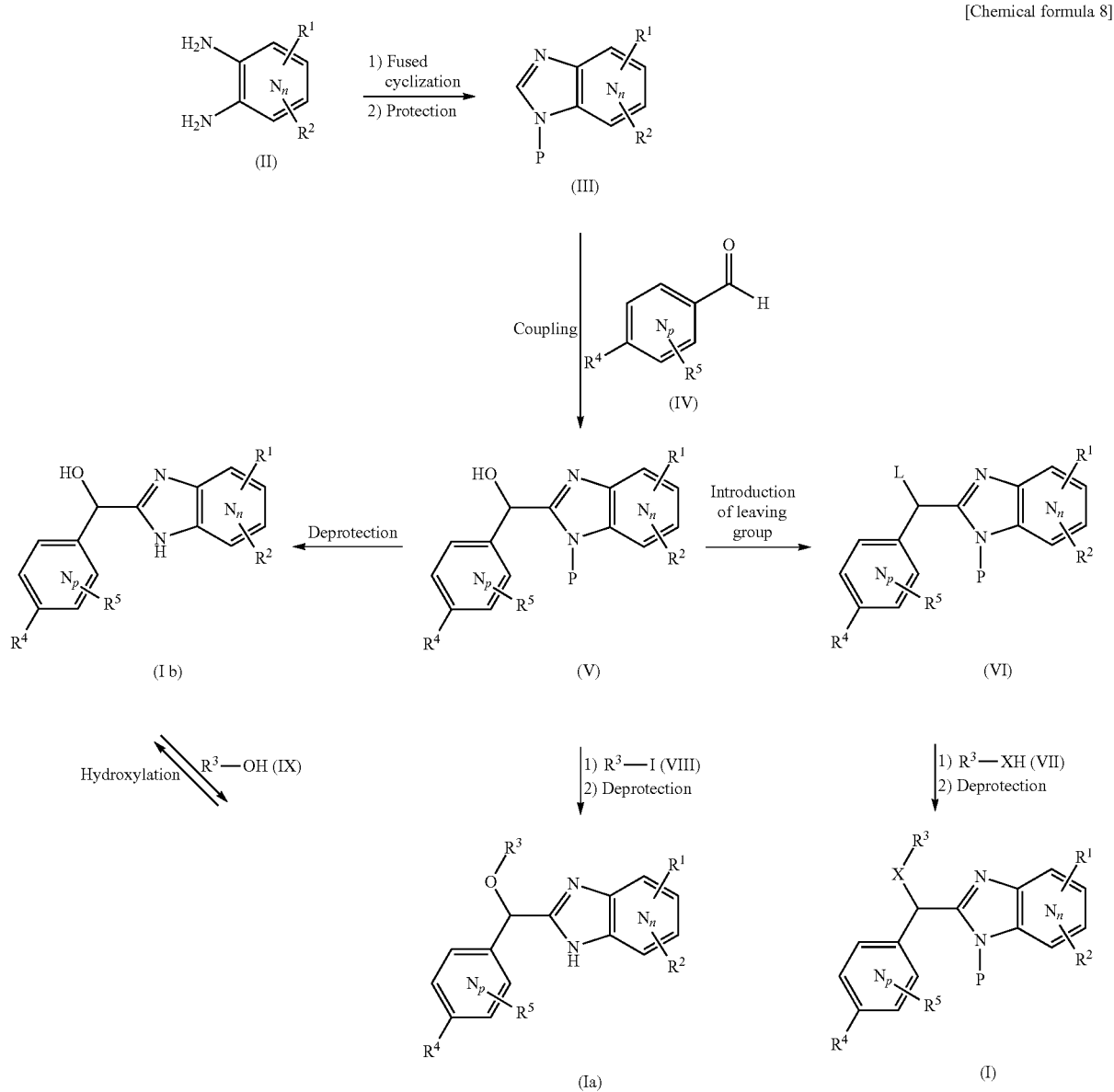

wherein $R^1$, $R^2$, $R^3$, $R^4$, $R^5$, $N_n$, $N_p$, and X have the same meanings as defined above; L represents a leaving group; and P represents a protective group.

A compound (III) can be produced by fused cyclization reaction of the compound (II), and subsequent introduction of a protective group. The fused cyclization reaction can be carried out by, for example, a method of heating under stirring a compound (II) and formic acid in an aqueous hydrochloric acid solution, or by a method of subjecting the compound (II) and ethyl orthoformate or methyl orthoformate to heating under stirring or microwave irradiation, in formic acid. The reaction temperature is usually 40° C. to 200° C., and preferably 40° C. to 150° C. The reaction time is usually 5 minutes to 48 hours, and preferably 5 minutes to 6 hours.

A compound (V) can be produced by allowing the compound (III) and a compound (IV) to react in an inert solvent in the presence of an organolithium reagent. As the organolithium reagent to be used, for example, n-butyllithium, sect-butyllithium, tert-butyllithium, lithium diisopropylamide (LDA), lithium tetramethylpiperizide, and lithium hexamethyldisilazide are used. The amount of use of the organolithium reagent is usually 1 equivalent to 5 equivalents, and preferably 1 equivalent to 3 equivalents, with respect to the compound (III). The inert solvent that is used in the reaction is not particularly limited as long as the reaction proceeds, but for example, diethyl ether, tetrahydrofuran (THF), dioxane, 1,2-dimethoxyethane, benzene, toluene, and hexane can be used. These may be used as mixtures of two or more kinds at appropriate proportions. The reaction temperature is usually –100° C. to 0° C., and preferably –78° C. to –30° C. The reaction time is usually 0.5 hours to 24 hours, and preferably 0.5 hours to 3 hours.

A compound (VI) can be produced by allowing a compound (V) and a leaving group-introducing agent to react in the presence or absence of a base, in the absence of a solvent or in an inert solvent. Examples of the leaving group-introducing agent that may be used include sulfonylating agents such as methanesulfonyl chloride, p-toluenesulfonyl chloride, and trifluoromethanesulfonyl chloride. The amount of use of the leaving group-introducing agent is usually 1 equivalent to 5 equivalents, and preferably 1 equivalent to 3 equivalents, with respect to the compound (V). The inert solvent that is used in the reaction is not particularly limited as long as the reaction proceeds, but for example, diethyl ether, THF, dioxane, 1,2-dimethoxyethane, benzene, toluene, hexane, dichloromethane, and chloroform can be used. These may also be used as mixtures of two or more kinds at appropriate proportions. The reaction temperature is usually –30° C. to room temperature, and preferably 0° C. to room temperature. The reaction time is usually 0.5 hours to 24 hours, and preferably 0.5 hours to 3 hours.

A compound (I) can be produced by allowing the compound (VI) and a compound (VII) to react in an inert solvent in the presence or absence of a base, and then deprotecting the product. Examples of the compound (VII) include alcohols such as methanol and ethanol; amines such as dimethylamine; and thiols such as ethanethiol. The inert solvent used in the reaction of the compound (VI) and the compound (VII) is not particularly limited as long as the reaction proceeds, but for example, chloroform, dichloromethane, diethyl ether, THF, benzene, toluene, xylene, N,N-dimethylformamide (DMF), and N,N-dimethylacetamide (DMA) can be used. These may also be used as mixtures of two or more kinds at appropriate proportions. As the base to be used in the reaction, for example, potassium carbonate, sodium carbonate, pyridine, triethylamine, 4-dimethylaminopyridine (DMAP), and diisopropylethylamine (DIPEA) can be used. The amount of use of the compound (VII) is usually 1 equivalent to 10 equivalents, and preferably 1 equivalent to 5 equivalents, with respect to the compound (VI). The reaction temperature is usually –20° C. to the reflux temperature, and preferably 0° C. to the reflux temperature. The reaction time is usually 0.5 hours to 100 hours, and preferably 1 hour to 48 hours.

A compound (Ib) can be produced by deprotection of the compound (V).

Furthermore, the compound (Ib) can also be produced by a hydroxylation reaction of a compound (Ia). The hydroxylation reaction is carried out by, for example, a method of heating under stirring or microwave irradiation in an aqueous solution of sulfuric acid or an aqueous hydrochloric acid solution, or in a solvent mixture with, for example, THF and dioxane. The reaction temperature is usually 40° C. to 200° C., and preferably 80° C. to 180° C. The reaction time is usually 5 minutes to 24 hours, and preferably 5 minutes to 3 hours.

The compound (Ia) can be produced in the same manner as described in the method described in WO 2004/048335, by allowing the compound (V) and an alkylating agent to react in an inert solvent in the presence of silver oxide, and then deprotecting the product. The inert solvent that is used in the reaction with an alkylating agent is not particularly limited as long as the reaction proceeds, but examples thereof include hydrocarbons such as benzene, toluene, cyclohexane, and hexane; and solvent mixtures thereof. Examples of the alkylating agent to be used include alkyl iodides such as methyl iodide and ethyl iodide. The reaction temperature is –20° C. to the reflux temperature, and preferably 0° C. to the reflux temperature. The reaction time is usually 30 minutes to 10 hours, and preferably 1 hour to 5 hours.

Furthermore, the compound (Ia) can be produced by using the compound (Ib), and reaction with a compound (IX) by a heating or microwave irradiation, in the presence of an acid catalyst. Examples of the acid catalyst to be used include sulfuric acid, and trifluoroacetic acid (TFA). Examples of the compound (IX) include alcohols and phenols such as ethanol, isopropanol, cyclohexanol, benzyl alcohol, 2-methoxyethyl alcohol, phenol, 4-chlorophenol, 2-hydroxypyridine, 3-hydroxypyridine, and 4-hydroxypyridine. The reaction temperature is usually 100° C. to 250° C., and preferably 150° C. to 200° C. The reaction time is usually 5 minutes to 3 hours, and preferably 10 hours to 1 hour.

Furthermore, the compound (Ia) can also be produced by an amide condensation reaction between a compound (II) and a compound (X), and a subsequent cyclization reaction.

Production Method 2

[Chemical formula 9]

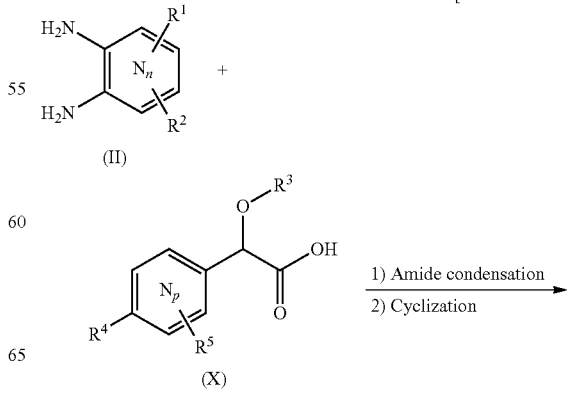

-continued

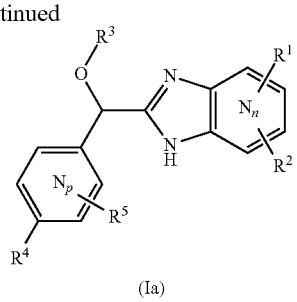

(Ia)

wherein $R^1$, $R^2$, $R^3$, $R^4$, $R^5$, $N_n$ and $N_p$ have the same meanings as defined above.

The amide condensation reaction is carried out by allowing the compound (II) and the compound (X) to react in an inert solvent in the presence of a condensing agent and in the presence or absence of 1 equivalent to 5 equivalents of, for example, a base. Meanwhile, the present reaction may also be carried out in the presence of a catalytic amount to 5 equivalents of 1-hydroxybenzotriazole (HOBt) and 1-hydroxy-7-azabenzotriazole (HOAt) according to necessity. As the condensing agent that is used in the reaction, for example, dicyclohexylcarbodiimide (DCC), 1-ethyl-3-(3-dimethylaminopropyl)carbodiimide hydrochloride (EDC.HCl), diisopropylcarbodiimide (DIPC), benzotriazol-1-yloxytris-dimethylaminophosphonium.hexafluorophosphate (BOP), diphenylphosphonylazide (DPPA), N,N-carbodiimidazole (CDI), and 2-(1H-7-azabenzotriazol-1-yl)-1,1,3,3-tetramethyluronium hexafluorophosphate (HATU) can be used. The amount of use of the condensing agent is usually 1 equivalent to 10 equivalents, and preferably 1 equivalent to 5 equivalents, with respect to the compound (X). The inert solvent used in the reaction is not particularly limited as long as the reaction proceeds, but for example, dichloromethane, chloroform, DMF, DMA, THF, dimethoxyethane, acetonitrile, benzonitrile, and ethyl acetate can be used. These may also be used as mixtures of two or more kinds at appropriate proportions. As the base to be used in the reaction, for example, pyridine, triethylamine, DMAP, and DIPEA can be used. The reaction temperature is 0° C. to the reflux temperature, and preferably 0° C. to room temperature. The reaction time is usually 0.5 hours to 100 hours, and preferably 1 hour to 48 hours.

The subsequent cyclization reaction is carried out by, for example, a method of heating under stirring or microwave irradiation in acetic acid, formic acid or trifluoroacetic acid, or in a solvent mixture of such an acid and an alcohol. The amount of use of the acid is 0.5 mL to 10 mL relative to 1 mmol of the reaction substrate. The reaction temperature is usually 40° C. to 200° C., and preferably 60° C. to 180° C. The reaction time is usually 5 minutes to 24 hours, and preferably 5 minutes to 3 hours.

Meanwhile, the compound (II) and compound (IV) that are used as the raw material compounds for the production methods 1 and 2 can be purchased as commercially available products, or can be produced according to methods that are known per se.

The compound (X) that is used as a raw material compound for the production method 2 can be produced by, for example, a method described in WO 2007/010516 or a method described in CHIRALITY, Wiley-Liss, (USA), 2003, Vol. 15, p. 609-614, from a benzaldehyde form as shown in the following scheme.

[Chemcial formula 10]

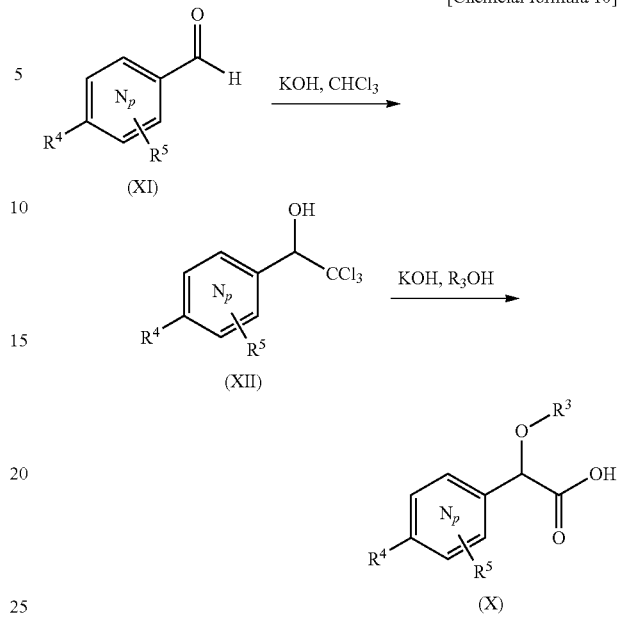

wherein $R^3$, $R^4$, $R^5$ and $N_p$ have the same meanings as defined above.

The compound (I) of the present invention thus obtainable has an excellent T-type calcium channel antagonistic action as will be disclosed in the Test Examples described below, and is also highly safe. Therefore, the compound (I) of the present invention is useful as a pharmaceutical agent for the prevention and treatment of diseases involving T-type calcium channels in animals including human beings, and particularly various diseases in which a T-type calcium channel antagonistic effect is effective. Examples of the relevant diseases include hypertension, atrial fibrillation, arrhythmia, cardiac hypertrophy, cardiac failure, renal dysfunction, and cancers.

A pharmaceutical composition containing the compound (I) of the present invention, a pharmaceutically acceptable salt thereof, or a solvate thereof as an active ingredient, can be prepared by using one or more kinds of the compound of the present invention and pharmaceutically acceptable carriers that are conventionally used in formulation, for example, an excipient and other additives, according to a method that is conventionally used. Administration may be achieved by any form of oral administration using, for example, tablets, pills, capsules, granules, powders, and liquids; and parenteral administration using injectable preparations such as, for example, intravenous injection and muscular injection, suppositories, transnasal agents, transmucosal agents, transdermal agents, inhalants. The amount of administration is appropriately determined according to individual cases in consideration of, for example, the disease or symptom to be treated, the age, body weight or gender of the subject of administration. Conventionally, in the case of oral administration, the amount of administration of an adult (weight: about 60 kg) per day is suitably about 1 mg to 1000 mg, preferably about 3 mg to 300 mg, and more preferably about 10 mg to 200 mg, in terms of the active ingredient (compound of the present invention), and this is administered once or in 2 to 4 divided doses. Furthermore, in the case of intravenous administration depending on the symptom, usually, the amount of administration of an adult per day is suitably about 0.01 mg to 100 mg, preferably about 0.01 mg to about 50 mg, and more preferably about 0.01 mg to about 20 mg, per kilogram of the weight, and this is administered once or in multiple divided doses a day. Furthermore, the pharmaceutical composition containing the compound of the present invention may appropriately contain other calcium antagonistic drugs or active ingredients of different types, as long as the purpose of the present invention is not contradicted.

Examples of solid compositions for oral administration according to the present invention include tablets, powders, and granules. Such a solid composition can be prepared by mixing one or more kinds of active ingredients with at least one inert excipient, for example, lactose, mannitol, glucose, hydroxypropyl cellulose, fine crystalline cellulose, starch, polyvinylpyrrolidone, or magnesium metasilicate aluminate. The solid composition may contain an additive other than the inert excipient, for example, a lubricating agent, a disintegrant, a stabilizing agent, a solubilizing agent or a dissolution aid, according to a conventional method. The tablets or pills may be coated with, for example, a sugar coating or a gastric or enteral film of sucrose, gelatin, hydroxypropyl cellulose, or hydroxypropylmethyl cellulose phthalate, as necessary.

The liquid composition for oral administration may contain, for example, an emulsion, a solution, a suspension, a syrup, or an elixir, which are pharmaceutically acceptable, and may contain an inert diluent that is generally used, for example, purified water or ethanol. The composition may also contain an additive other than an inert diluent, for example, an auxiliary agent such as a wetting agent or a suspending agent, a sweetening agent, a flavoring agent, an aromatic agent or an antiseptic.

The injectable preparation for parenteral administration may contain a sterile, aqueous or non-aqueous solution, suspension or emulsion. A water-soluble solution or suspension may contain, for example, as a diluent, distilled water for injection and physiological saline. A non-water-soluble solution or suspension may contain, for example, as a diluent, propylene glycol, polyethylene glycol, a plant oil such as olive oil, an alcohol such as ethanol, or Polysorbate 80. Such a composition may contain an auxiliary agent such as an antiseptic, a wetting agent, an emulsifier, a dispersant, a stabilizer, a solubilizing agent, or a dissolution aid. These can be sterilized by, for example, filtration through a bacteria-retaining filter, incorporation of a disinfectant, or irradiation. Furthermore, a sterile solid composition can be prepared and dissolved in sterile water or a sterile solvent for injection before use, and the resulting solution can be used.

EXAMPLES

Hereinafter, the present invention will be specifically described by way of Examples, but the present invention is not intended to be limited to these.

Reference Example 1

Regioisomer mixture of 1-dimethoxymethyl-5-fluoro-1H-benzimidazole

Under ice cooling, 4 mol/L hydrochloric acid (200 mL) and formic acid (38.3 g) were sequentially added to 4-fluoro-1,2-phenylenediamine (21.0 g), and the mixture was heated to reflux for 90 minutes while being stirred. Under ice cooling, the reaction mixture was basified with a 10% aqueous solution of sodium hydroxide and extracted with ethyl acetate. The organic layer was washed with saturated brine and then dried over anhydrous sodium sulfate. After distilling off the solvent under reduced pressure, the residue was washed with diisopropyl ether, and 5-fluorobenzimidazole (19.7 g) was obtained. 5-Fluorobenzimidazole (19.7 g) thus obtained was dissolved in toluene (500 mL), and methyl orthoformate (38.7 g) and benzenesulfonic acid monohydrate (1.0 g) were sequentially added thereto. The mixture was heated to reflux for 40 hours while being stirred. After distilling off the solvent and methyl orthoformate under reduced pressure, the residue was diluted with toluene. Diisopropylamine (1 mL) and a saturated aqueous solution of sodium hydrogen carbonate were sequentially added thereto under ice cooling, and the mixture was extracted with ethyl acetate. The organic layer was washed with saturated brine and then dried over anhydrous sodium sulfate. After distilling off the solvent under reduced pressure, the residue was purified by basic silica gel chromatography (20% to 100% ethyl acetate/hexane), and thus the title compound (25.2 g) was obtained.

Compounds 2 and 3 that were produced in the same manner as described in Reference Example 1 by using corresponding raw materials, are shown in Table 1.

TABLE 1

| Reference Example | Compound name (regioisomer mixture) |
|---|---|
| 2 | 1-Diethoxymethyl-5-ethoxy-1H-benzimidazole |
| 3 | 1-Diethoxymethyl-5-methoxy-1H-benzimidazole |

Reference Example 4

Regioisomer mixture of (4-benzyloxyphenyl)-(1-diethoxymethyl-5-methoxy-1H-benzimidazol-2-yl)methanol In an argon atmosphere, the compound of Reference Example 3 (2.4 g) and 4-benzyloxybenzaldehyde (2.4 g) were dissolved in THF (30 mL), and about 1.14 mol/L of LDA (hexane, THF solution) (10 mL) was added dropwise to the solution at a rate of 3 mL per minute under cooling at −78° C. The mixture was stirred for one hour at the same temperature. A saturated aqueous solution of ammonium chloride was added to the reaction mixture, and the mixture was extracted with ethyl acetate. The organic layer was washed with saturated brine and then dried over anhydrous sodium sulfate. After distilling off the solvent under reduced pressure, the residue was purified by basic silica gel column chromatography (20% to 100% ethyl acetate/hexane), and thus the title compound (3.3 g) was obtained.

Compound 5 that were produced in the same manner as described in Reference Example 4 by using corresponding raw materials is shown in Table 2.

TABLE 2

| Reference Example | Compound name (regioisomer mixture) |
|---|---|
| 5 | (1-Diethoxymethyl-5-ethoxy-1H-benzimidazol-2-yl)-[4-(2,5-difluorobenzyloxy)phenyl]methanol |

Reference Example 6

Regioisomer mixture of 1-methoxymethyl-1H-imidazo[4,5-b]pyridine

4-Azabenzimidazole (7.5 g) was dissolved in DMF (125 mL), and cesium carbonate (68 g) was added thereto. Subsequently, chloromethyl methyl ether (7.0 mL) was added dropwise thereto under ice cooling, and the mixture was stirred for one hour at room temperature. Chloromethyl methyl ether (1.9 mL) was added to the reaction mixture, and the mixture was stirred for 12 hours at room temperature. A saturated aqueous solution of sodium hydrogen carbonate was added to the reaction mixture, and the mixture was extracted with chloroform. The organic layer was washed with saturated brine and then dried over anhydrous sodium sulfate. After distilling off the solvent under reduced pressure, the residue was purified by silica gel column chromatography (0% to 15% methanol/chloroform), and the title compound (5.7 g) was obtained.

Compounds 7 and 8 that were produced in the same manner as described in Reference Example 6 by using corresponding raw materials, are shown in Table 3.

TABLE 3

| Reference Example | Compound name(regioisomer mixture) |
|---|---|
| 7 | 6-Chloro-1-methoxymethyl-1H-imidazo[4,5-b]pyridine |
| 8 | 6-Fluoro-1-methoxymethyl-1H-imidazo[4,5-b]pyridine |

Reference Example 9

Regioisomer mixture of (6-chloro-1-methoxymethyl-1H-imidazo[4,5-b]pyridin-2-yl)-(4-trifluoromethoxyphenyl) methanol In an argon atmosphere, the compound of Reference Example 7 (700 mg) and 4-trifluoromethoxybenzaldehyde (800 mg) were dissolved in THF (12 mL), and about 1.14 mol/L of LDA (hexane, THF solution) (3.7 mL) was added dropwise thereto under cooling at −78° C. The mixture was stirred for 2 hours at the same temperature. Water was added to the reaction mixture, and the mixture was extracted with ethyl acetate. The organic layer was washed with saturated brine and then dried over anhydrous sodium sulfate. After distilling off the solvent under reduced pressure, the residue was purified by silica gel column chromatography (25% to 75% ethyl acetate/hexane), and thus the title compound (682 mg) was obtained.

Compounds 10 to 20 that were produced in the same manner as described in Reference Example 9 by using corresponding raw materials, are shown in Table 4.

TABLE 4

| Reference Example | Compound name (regioisomer mixture) |
|---|---|
| 10 | (1-Methoxymethyl-5-nitro-1H-benzimidazol-2-yl)-(4-trifluoromethoxyphenyl)methanol |
| 11 | (5-Chloro-1-methoxymethyl-1H-imidazo[4,5-b]pyridin-2-yl)-(4-trifluoromethoxyphenyl)methanol |
| 12 | (1-Methoxymethyl-5-propylsulfanyl-1H-benzimidazol-2-yl)-(4-trifluoromethoxyphenyl)methanol |
| 13 | (6-Fluoro-1-methoxymethyl-1H-imidazo[4,5-b]pyridin-2-yl)-[4-(4-methylbenzyloxy)phenyl]methanol |
| 14 | [4-(4-Fluorobenzyloxy)phenyl]-(1-methoxymethyl-1H-imidazo[4,5-b]pyridin-2-yl)methanol |
| 15 | (1-Methoxymethyl-1H-imidazo[4,5-b]pyridin-2-yl)-[4-(4-methylbenzyloxy)phenyl]methanol |
| 16 | (6-Chloro-1-methoxymethyl-1H-imidazo[4,5-b]pyridin-2-yl)-[4-(4-methylbenzyloxy)phenyl]methanol |
| 17 | (6-Chloro-1-methoxymethyl-1H-imidazo[4,5-b]pyridin-2-yl)-[4-(4-fluorobenzyloxy)phenyl]methanol |

TABLE 4-continued

| Reference Example | Compound name (regioisomer mixture) |
|---|---|
| 18 | [4-(4-Fluorobenzyloxy)phenyl]-(6-fluoro-1-methoxymethyl-1H-imidazo[4,5-b]pyridin-2-yl)methanol |
| 19 | (1-Methoxymethyl-1H-imidazo[4,5-b]pyridin-2-yl)-(4-trifluoromethoxyphenyl)methanol |
| 20 | (2,2-difluorobenzo[1,3]dioxol-5-yl)-(1-methoxymethyl-1H-imidazo[4,5-b]pyridin-2-yl)methanol |

Reference Example 21

Ethoxy(4-hydroxyphenyl)acetic acid ethyl ester

DL-4-hydroxymandelic acid (25.5 g) was dissolved in ethanol (227 mL), and concentrated sulfuric acid (4.5 mL) was added thereto under ice cooling. The mixture was stirred for several minutes at room temperature, and then was heated to reflux for 21 hours while being stirred. After distilling off the solvent under reduced pressure, the residue was poured into ice water. The mixture was neutralized with a saturated aqueous solution of sodium hydrogen carbonate and extracted with ethyl acetate. The organic layer was washed with saturated brine and dried over anhydrous sodium sulfate After distilling off the solvent under reduced pressure, the residue was washed with diisopropyl ether and dried, and thus the title compound (26.3 g) was obtained.

$^1$H-NMR (CDCl$_3$) δ: 1.21 (3H, t, J=6.3 Hz), 1.26 (3H, t, J=6.1 Hz), 3.44-3.63 (2H, m), 4.10-4.25 (2H, m), 4.80 (1H, s), 6.81 (2H, d, J=9.2 Hz), 7.32 (2H, d, J=9.2 Hz).

ESI-MS Found: m/z 223 (M−H)$^-$

Reference Example 22

Ethoxy(4-hydroxyphenyl)acetic acid

The compound of Reference Example 21 (39.3 g) was dissolved in ethanol (315 mL), and a 10% aqueous solution of sodium hydroxide (156 mL) was added thereto under ice cooling. The mixture was stirred for 4 hours at room temperature. The reaction mixture was acidified with 2 mol/L hydrochloric acid, and then ethanol was distilled off under reduced pressure. The residue was diluted with water, and the dilution was extracted with ethyl acetate. The organic layer was washed with saturated brine and then dried over anhydrous sodium sulfate. After distilling off the solvent under reduced pressure, the residue was washed with diethyl ether, and recrystallization was carried out with ethyl acetate. Thus, the title compound (26.3 g) was obtained.

$^1$H-NMR (DMSO-d$_6$) δ: 1.11 (3H, t, J=7.0 Hz), 3.35 (1H, m), 3.48 (1H, m), 4.69 (1H, s), 6.72 (2H, d, J=9.1 Hz), 7.17 (2H, d, J=9.1 Hz), 9.46 (1H, br s), 12.58 (1H, br s).

ESI-MS Found: m/z 195 (M−H)$^-$

Reference Example 23

[4-(2,5-Difluorobenzyloxy)phenyl]ethoxyacetic acid

The compound of Reference Example 21 (13.6 g) was dissolved in DMF (200 mL), and potassium carbonate (10.5 g) and 2,5-difluorobenzylbromide (14.6 g) were added thereto under ice cooling. The mixture was stirred for 6.5 hours at room temperature. After distilling off the solvent under reduced pressure, the residue was diluted with a saturated aqueous solution of ammonium chloride, and the mixture was extracted with diethyl ether. The organic layer was washed with saturated brine and then dried over anhydrous sodium sulfate. After distilling off the solvent under reduced pressure, a crude product was obtained.

The crude product thus obtained was dissolved in ethanol (300 mL), and a 10% aqueous solution of sodium hydroxide (100 mL) was added thereto under ice cooling. The mixture was stirred for 11 hours at room temperature. After distilling off the solvent under reduced pressure, the residue was acidified with 2 mol/L hydrochloric acid and extracted with chloroform. The organic layer was washed with saturated brine and then dried over anhydrous sodium sulfate. After distilling off the solvent under reduced pressure, the residue was purified by silica gel column chromatography (4% to 10% methanol/chloroform), and thus the title compound (20.0 g) was obtained.

$^1$H-NMR (CDCl$_3$) δ: 1.27 (3H, t, J=7.0 Hz), 3.52-3.62 (2H m), 4.84 (1H, s), 5.11 (2H, s), 6.94-7.09 (4H, m), 7.19-7.25 (1H, m), 7.35-7.38 (2H, m).

ESI-MS Found: m/z 321 (M–H)$^-$

Compounds 24 to 30 that were produced in the same manner as described in Reference Example 23 by using corresponding raw materials, are shown in Table 5.

TABLE 5

| Reference Example | Compound name | MS |
|---|---|---|
| 24 | [4-(2,5-Difluorobenzyloxy)-3-methoxyphenyl]-ethoxyacetic acid | 351 (ESI–) |
| 25 | [4-(2,5-Difluorobenzyloxy)-2-methoxyphenyl]-ethoxyacetic acid | 351 (ESI–) |
| 26 | [3-Chloro-4-(2,5-difluorobenzyloxy)phenyl]-ethoxyacetic acid | 355 (ESI–) |
| 27 | [4-(2,5-Difluorobenzyloxy)phenyl]methoxy-acetic acid | 307 (ESI–) |
| 28 | [4-(2,5-Difluorobenzyloxy)phenyl]isopropoxy-acetic acid | 335 (ESI–) |
| 29 | [4-(2,5-Difluorobenzyloxy)phenyl]isobutoxy-acetic acid | 349 (ESI–) |
| 30 | [4-(2,5-Difluorobenzyloxy)phenyl]-(2-methoxyethoxy)acetic acid | 351 (ESI–) |

Reference Example 31

Ethoxy(4-trifluoromethoxyphenyl)acetic acid

4-Trifluoromethoxybenzaldehyde (5.0 g) and chloroform (7.2 g) were dissolved in DMF (16 mL), and a methanol solution (4.5 mL) of potassium hydroxide (1.2 g) was added dropwise thereto under ice cooling. The mixture was stirred for 2 hours at the same temperature. 1 mol/L hydrochloric acid (36 mL) and toluene (36 mL) were added thereto, and the mixture was stirred for 13 hours at room temperature. The organic layer and the aqueous layer were separated, and the aqueous layer was extracted with toluene. The organic layer was washed sequentially with water, a saturated aqueous solution of sodium hydrogen carbonate, and water, and then was dried over anhydrous sodium sulfate. The solvent was distilled off under reduced pressure, and thus a crude product was obtained.

The crude product thus obtained was dissolved in ethanol (26 mL), and an ethanol solution (52 mL) of potassium hydroxide (7.4 g) was added dropwise thereto. The mixture was heated to reflux for 3 hours while being stirred. Water was added to the reaction mixture, and the mixture was washed with diethyl ether. Subsequently, the mixture was acidified with 6 mol/L hydrochloric acid and extracted with ethyl acetate. The organic layer was washed with saturated brine and then dried over anhydrous sodium sulfate. After distilling off the solvent under reduced pressure, the residue was purified by silica gel column chromatography (0% to 20% methanol/chloroform), and thus the title compound (3.2 g) was obtained as a yellow oily material.

$^1$H-NMR (CDCl$_3$) δ: 1.30 (3H, t, J=7.0 Hz), 3.54-3.69 (2H, m), 4.90 (1H, s), 7.22-7.25 (2H, m), 7.47-7.50 (2H, m).

ESI-MS Found: m/z 263 (M–H)$^-$

Reference Example 32

Methoxy(4-trifluoromethoxyphenyl)acetic acid

4-Trifluoromethoxybenzaldehyde (25.0 g) was dissolved in a 1:1 mixed solution of methanol/1,4-dioxane (500 mL), and bromoform (30.3 g) was added thereto under ice cooling. Subsequently, a methanol solution (150 mL) of potassium hydroxide (3.3 g) was added dropwise thereto, and the mixture was stirred for 22 hours at room temperature. After distilling off the solvent under reduced pressure, the residue was diluted with water. The mixture was acidified with 3 mol/L hydrochloric acid and extracted with ethyl acetate. The organic layer was washed with saturated brine and then dried over anhydrous sodium sulfate. After distilling off the solvent under reduced pressure, the residue was purified by silica gel column chromatography (50% to 100% ethyl acetate/hexane), and the title compound (29.4 g) was obtained as a crude product.

Compounds 33 to 35 that were produced in the same manner as described in Reference Example 32 by using corresponding raw materials, are shown in Table 6.

TABLE 6

| Reference Example | Compound name |
|---|---|
| 33 | Ethoxy(4-trifluoromethylsulfanylphenyl)acetic acid |
| 34 | (6-Benzyloxy-pyridin-3-yl)ethoxyacetic acid |
| 35 | Ethoxy(4-phenylsulfamoylphenyl)acetic acid |

Reference Example 36

Ethoxy(4-trifluoromethanesulfonylphenyl)acetic acid

The compound of Reference Example 33 (3.4 g) was dissolved in TFA (50 mL), and a 30% aqueous hydrogen peroxide solution (11.0 g) was added thereto under ice cooling. The mixture was stirred for 20 hours at room temperature. The reaction mixture was poured into ice water and neutralized with a 10% aqueous solution of sodium hydroxide, and the mixture was extracted with ethyl acetate. The organic layer was washed with saturated brine and then dried over anhydrous sodium sulfate. After distilling off the solvent under reduced pressure, the residue was purified by silica gel column chromatography (10% to 100% ethyl acetate/hexane), and thus a crude product of the title compound (620 mg) was obtained.

Reference Example 37

4-[Ethoxy(5-ethoxy-1H-benzimidazol-2-yl)methyl] phenol

The title compound (57 mg) was obtained in the same manner as described in Example 65 by using the compound of Reference Example 22 (300 mg) and 4-ethoxy-1,2-phenylenediamine (134 mg).

¹H-NMR (DMSO-d₆) δ: 1.18 (3H, t, J=7.0 Hz), 1.30-1.33 (3H, m), 3.41-3.51 (2H, m), 3.96-4.01 (2H, m), 5.48-5.50 (1H, m), 6.70-7.38 (7H, m), 9.41 (1H, s), 12.13-12.16 (1H, m).
ESI-MS Found: m/z 313 (M+H)⁺

Reference Example 38

[4-(tert-Butyldimethylsilyloxy)phenyl]ethoxyacetic acid

The compound of Reference Example 22 (12.0 g) was dissolved in DMF (200 mL), and imidazole (18.3 g) and tert-butyldimethylsilyl chloride (TBDMSCl) (19.4 g) were added thereto under ice cooling. The mixture was stirred for 5 hours at room temperature. Water was added to the reaction mixture, and the mixture was extracted with chloroform. The extract was dried over anhydrous sodium sulfate, and the solvent was distilled off under reduced pressure. Thus, a crude product of the title compound (11.8 g) was obtained.

Reference Example 39

2-{[4-(tert-Butyldimethylsilyloxy)phenyl]ethoxymethyl}-5-ethoxy-1H-benzimidazole The title compound (9.4 g) was obtained in the same manner as described in Example 65 by using the compound of Reference Example 38 (9.0 g) and 4-ethoxy-1,2-phenylenediamine (4.9 g).
¹H-NMR (CDCl₃) δ: 0.17 (6H, s), 0.96 (9H, s), 1.27 (3H, t, J=7.0 Hz), 1.42 (3H, t, J=7.0 Hz), 3.52-3.67 (2H, m), 4.00-4.07 (2H, m), 5.61 (1H, s), 6.77-6.89 (4H, m), 7.20-7.60 (3H, m), 9.30-9.35 (1H, br m).
ESI-MS Found: m/z 427 (M+H)⁺

Reference Example 40

2-{[4-(tert-Butyldimethylsilyloxy)phenyl]ethoxymethyl}-5-ethoxybenzimidazole-1-carboxylic acid tert-butyl ester The compound of Reference Example 39 (9.4 g) was dissolved in dichloromethane (440 mL), and di-tert-butyl bicarbonate (5.3 g), triethylamine (8.5 g) and DMAP (215 mg) were sequentially added thereto under ice cooling. The mixture was stirred for 30 minutes at room temperature. A saturated aqueous solution of sodium carbonate was added to the reaction mixture, and the mixture was extracted with dichloromethane. The extract was dried over anhydrous sodium sulfate. After distilling off the solvent under reduced pressure, the residue was purified by silica gel column chromatography (15% to 25% ethyl acetate/hexane), and thus the title compound (11.5 g) was obtained as a regioisomer mixture.

Reference Example 41

5-Ethoxy-2-[ethoxy(4-hydroxyphenyl)methyl]benzimidazole-1-carboxylic acid tert-butyl ester The compound of Reference Example 40 (11.5 g) was dissolved in THF (315 mL), and a 1 mol/L THF solution (22.3 mL) of tetra-n-butylammonium fluoride (TBAF) was added thereto under ice cooling. The mixture was stirred for 30 minutes at room temperature. A saturated aqueous solution of ammonium chloride was added to the reaction mixture, and the mixture was extracted with ethyl acetate. The organic layer was washed with saturated brine and then dried over anhydrous sodium sulfate. After distilling off the solvent under reduced pressure, the residue was purified by silica gel column chromatography (25% to 50% ethyl acetate/hexane), and the title compound (8.4 g) was obtained as a regioisomer mixture.

Reference Example 42

(4-Cyanophenyl)ethoxyacetic acid

4-Cyanobenzaldehyde (3.0 g) was dissolved in a 1:1 mixed solution of ethanol/1,4-dioxane (80 mL), and bromoform (7.0 g) was added thereto under ice cooling. Subsequently, an ethanol solution (40 mL) of potassium hydroxide (7.6 g) was carefully added thereto, and the mixture was stirred for 6 hours at room temperature. After distilling off the solvent under reduced pressure, the residue thus obtained was diluted with water. The mixture was acidified with a 2 mol/L hydrochloric acid and extracted with ethyl acetate. The organic layer was washed with saturated brine and then dried over anhydrous sodium sulfate. After distilling off the solvent under reduced pressure, the residue was purified by silica gel column chromatography (50% to 100% ethyl acetate/hexane), and the title compound (2.6 g) was obtained as a crude product.

Reference Example 43

4-[Ethoxy(5-ethoxy-1H-benzimidazol-2-yl)methyl]benzonitrile

The title compound (870 mg) was obtained as a colorless solid in the same manner as described in Example 65 by using the compound of Reference Example 42 (1.1 g) and 4-ethoxy-1,2-phenylenediamine (912 mg).
¹H-NMR (CDCl₃) δ: 1.33 (3H, t, J=7.0 Hz), 1.43 (3H, t, J=7.0 Hz), 3.66 (2H, q, J=7.0 Hz), 4.05 (2H, q, J=7.0 Hz), 5.72 (1H, s), 6.87-7.31 (3H, m), 7.63 (4H, q, J=8.5 Hz), 9.19 (1H, s).
ESI-MS Found: m/z 322 (M+H)³⁰

Reference Example 44

4-[Ethoxy(5-ethoxy-1H-benzimidazol-2-yl)methyl]benzoic acid

The compound of Reference Example 43 (300 mg) was dissolved in 1,4-dioxane (20 mL), and a 30% aqueous solution of sodium hydroxide (10 mL) was added thereto. The mixture was heated to reflux for 16 hours while being stirred. The reaction mixture was washed with diethyl ether. Subsequently, the aqueous layer was acidified with a 6 mol/L hydrochloric acid and extracted with ethyl acetate. The organic layer was washed with saturated brine and then dried over anhydrous sodium sulfate. After distilling off the solvent under reduced pressure, the residue was purified by silica gel column chromatography (10% to 40% methanol/chloroform), and thus the title compound (130 mg) was obtained.
¹H-NMR (DMSO-d₅) δ: 1.21 (3H, t, J=7.0 Hz), 1.32 (3H, t, J=7.0 Hz), 3.54 (2H, q, J=7.0 Hz), 3.99 (2H, q, J=7.0 Hz), 5.72 (1H, s), 6.75 (1H, d, J=7.7 Hz), 6.87-7.10 (1H, m), 7.30-7.44 (1H, m), 7.54 (2H, d, J=8.1 Hz), 7.92 (2H, d, J=8.1 Hz), 12.24-13.11 (1H, br m).
ESI-MS Found: m/z 339 (M−H)⁻

Reference Example 45

Hydroxy(4-trifluoromethoxyphenyl) acetic acid ethyl ester

4-Trifluoromethoxybenzaldehyde (10.0 g) was dissolved in dichloromethane (105 mL), and trimethylsilyl cyanide (7.0 g) and triethylamine (530 mg) were added thereto. The mixture was stirred for 4 hours at room temperature. The reaction mixture was distilled off under reduced pressure, and (4-trifluoromethoxyphenyl)trimethylsilyloxyacetonitrile (15.0 g) was obtained.

(4-trifluoromethoxyphenyl)trimethylsilyloxyacetonitrile (15.0 g) thus obtained was dissolved in diethyl ether (100 mL), and a 2 mol/L ethanol solution of hydrogen chloride (100 mL) was added thereto. The mixture was stirred for 65 hours at room temperature. The reaction mixture was distilled off under reduced pressure, subsequently water was added the residue, and the mixture was extracted with chloroform. The organic layer was washed with saturated brine and then dried over anhydrous sodium sulfate, and the solvent was distilled off under reduced pressure. Thus, the title compound (13.0 g) was obtained.

$^1$H-NMR (CDCl$_3$) δ: 1.24 (3H, t, J=7.1 Hz), 3.51 (1H, brs), 4.14-4.32 (2H, m), 5.17 (1H, s), 7.21 (2H, d, J=8.6 Hz), 7.47 (2H, d, J=8.6 Hz).

Reference Example 46

Hydroxy(4-trifluoromethoxyphenyl)acetic acid

The compound of Reference Example 45 (10.0 g) was dissolved in ethanol (15 mL), and a 10% aqueous solution of sodium hydroxide (50 mL) was added thereto. The mixture was stirred for 2 hours at room temperature. Water was added to the reaction mixture, and the mixture was washed with diethyl ether. Subsequently, the aqueous layer was acidified with a 6 mol/L hydrochloric acid and extracted with diethyl ether. The organic layer was washed with saturated brine and then dried over anhydrous sodium sulfate, and the solvent was distilled off under reduced pressure. Thus, the title compound (8.7 g) was obtained as a colorless solid.

$^1$H-NMR (CDCl$_3$) δ: 5.27 (1H, s), 7.23 (2H, d, J=7.9 Hz), 7.47-7.52 (2H, m).

ESI-MS Found: m/z 235 (M−H)$^−$

Reference Example 47

1-(4-Fluorobenzyl)-1H-indole-5-carboaldehyde

Indole-5-carboaldehyde (1.0 g) was dissolved in DMF (14 mL), and potassium hydroxide (460 mg) and 4-fluorobenzyl bromide (1.4 g) were sequentially added thereto under ice cooling. The mixture was stirred for 65 hours at room temperature. Water was added to the reaction mixture, and the mixture was extracted with chloroform. The organic layer was washed with saturated brine and then dried over anhydrous sodium sulfate. After distilling off the solvent under reduced pressure, the residue was purified by silica gel column chromatography (20% to 50% ethyl acetate/hexane), and the title compound (1.2 g) was obtained as a pale yellow solid.

$^1$H-NMR (CDCl$_3$) δ: 5.34 (2H, s), 6.72 (1H, dd, J=3.3, 0.9 Hz), 6.98-7.11 (4H, m), 7.21 (1H, d, J=3.3 Hz), 7.36 (1H, d, J=8.6 Hz), 7.76 (1H, dd, J=8.6, 1.6 Hz), 8.18 (1H, d, J=0.9 Hz), 10.03 (1H, s).

ESI-MS Found: m/z 254 (M+H)$^+$

Example 1

(5-Fluoro-1H-benzimidazol-2-yl)-(4-trifluoromethoxyphenyl)methanol

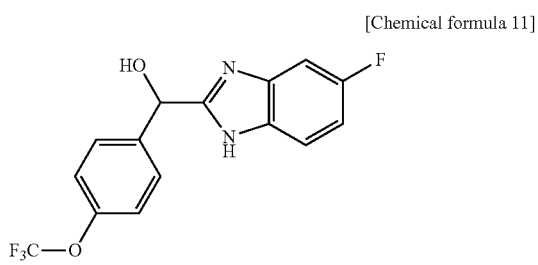 [SMILES: OC(c1ccc(OC(F)(F)F)cc1)c1nc2cc(F)ccc2[nH]1]

[Chemical formula 11]

In an argon atmosphere, the compound of Reference Example 1 (5.0 g) and 4-trifluoromethoxybenzaldehyde (5.0 g) were dissolved in THF (100 mL), and under cooling at −78° C., about 1.14 mol/L lithium diisopropylamide (LDA) (hexane, THF solution) (25 mL) was added dropwise thereto at a rate of 3 mL per minute. The mixture was stirred for one hour at the same temperature. A saturated aqueous solution of ammonium chloride was added to the reaction mixture, and the mixture was extracted with ethyl acetate. The organic layer was washed with saturated brine and then dried over anhydrous sodium sulfate. After distilling off the solvent under reduced pressure, and the residue was dissolved in THF (150 mL), and 1 mol/L hydrochloric acid (150 mL) was added thereto under ice cooling. The mixture was stirred for 4 hours at room temperature. After distilling off the solvent under reduced pressure, the residue was basified with a saturated aqueous solution of sodium hydrogen carbonate and extracted with ethyl acetate. The organic layer was washed with saturated brine and then dried over anhydrous sodium sulfate. After distilling off the solvent under reduced pressure, the residue was purified by silica gel column chromatography (20% to 100% ethyl acetate/hexane), and thus the title compound (3.7 g) was obtained as a colorless amorphous material.

$^1$H-NMR (CDCl$_3$) δ: 6.05 (1H, s), 6.94-7.03 (1H, m), 7.15-7.22 (3H, m), 7.44-7.50 (3H, m).

ESI-MS Found: m/z 327 (M+H)$^+$

Example 2

(5-Ethoxy-1H-benzimidazol-2-yl)-(4-trifluoromethoxyphenyl)methanol

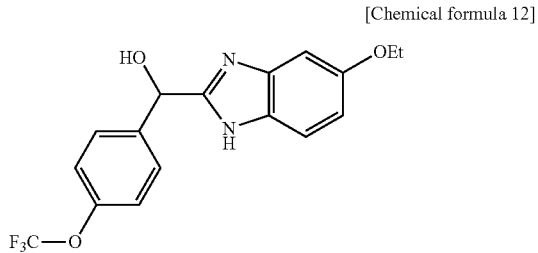

[Chemical formula 12]

The title compound (459 mg) was obtained as a pale yellow amorphous material, in the same manner as described in Example 1 by using the compound of Reference Example 2 (500 mg) and 4-trifluoromethoxybenzaldehyde (443 mg).

$^1$H-NMR (CDCl$_3$) δ: 1.38 (3H, t, J=7.0 Hz), 3.91 (2H, q, J=7.0 Hz), 5.98 (1H, s), 6.81-6.83 (2H, m), 7.04-7.07 (2H, m), 7.25-7.39 (3H, m).

ESI-MS Found: m/z 353 (M+H)$^+$

Examples 3 to 16

Compounds 3 to 16 that were produced in the same manner as described in Example 1 by using corresponding raw materials, are shown in Tables 7 and 8.

TABLE 7

| Example | Structural formula | $^1$H-NMR (CDCl$_3$) | MS |
|---|---|---|---|
| 3 | 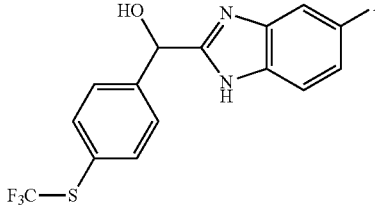 | δ: 6.06 (1H, s), 6.93-7.02 (1H, m), 7.14-7.17 (1H, m), 7.36-7.44 (1H, br m), 7.49 (2H, d, J = 8.2 Hz), 7.60 (2H, d, J = 8.2 Hz). | 343 (ESI+) |
| 4 | 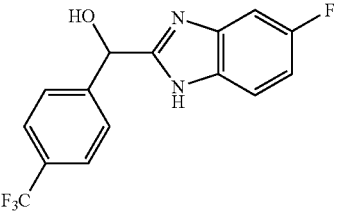 [SMILES: OC(c1ccc(C(F)(F)F)cc1)c1nc2cc(F)ccc2[nH]1] | δ: 6.12 (1H, br s), 6.96-7.03 (1H, m), 7.12-7.28 (1H, m), 7.36-7.63 (5H, m). | 311 (ESI+) |
| 5 | 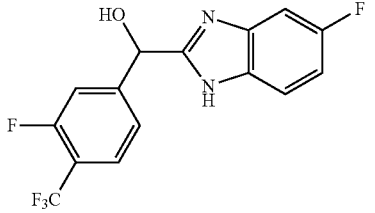 [SMILES: OC(c1ccc(C(F)(F)F)c(F)c1)c1nc2cc(F)ccc2[nH]1] | δ: 6.10 (1H, s), 6.97-7.04 (1H, m), 7.18-7.23 (1H, m), 7.35-7.45 (3H, m), 7.55-7.60 (1H, m). | 329 (ESI+) |
| 6 | 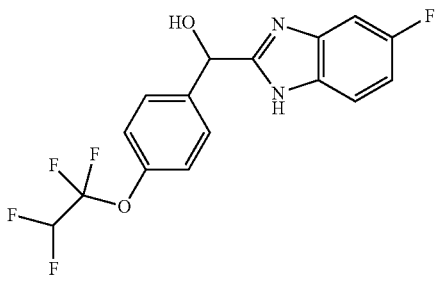 [SMILES: OC(c1ccc(OC(F)(F)C(F)F)cc1)c1nc2cc(F)ccc2[nH]1] | δ: 5.90 (1H, tt, J = 53.0, 2.9 Hz), 6.05 (1H, s), 6.95-7.02 (1H, m), 7.13-7.23 (3H, m), 7.37-7.48 (3H, m). | 359 (ESI+) |
| 7 | 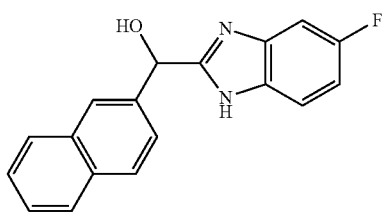 [SMILES: OC(c1ccc2ccccc2c1)c1nc2cc(F)ccc2[nH]1] | δ: 6.19 (1H, s), 6.93-7.00 (1H, m), 7.13-7.23 (1H, m), 7.38-7.51 (4H, m), 7.80-7.85 (3H, m), 7.94 (1H, s). | 293 (ESI+) |

TABLE 7-continued

| Example | Structural formula | ¹H-NMR (CDCl₃) | MS |
|---|---|---|---|
| 8 | | *DMSO-d₆ was used as a solvent.<br>δ: 6.00 (1H, s), 6.69 (1H, brs), 7.01-7.07 (1H, m), 7.28-7.31 (1H, m), 7.34-7.37 (1H, m), 7.42-7.57 (5H, m), 7.61-7.66 (4H, m). | 317 (ESI−) |
| 9 | | δ: 1.42 (3H, t, J = 7.0 Hz), 4.02 (2H, q, J = 7.0 Hz), 5.08 (2H, s), 5.98 (1H, s), 6.87 (1H, dd, J = 8.8, 2.4 Hz), 6.93-7.08 (5H, m), 7.17-7.40 (4H, m). | 411 (ESI+) |

TABLE 8

| Example | Structural formula | ¹H-NMR (CDCl₃) | MS |
|---|---|---|---|
| 10 | | δ: 5.02 (2H, s), 5.96 (1H, s), 6.93-7.00 (4H, m), 7.14-7.17 (1H, m), 7.28-7.45 (7H, m). | 349 (ESI+) |
| 11 | | δ: 6.02 (1H, s), 6.90-6.97 (1H, m), 7.02-7.06 (2H, m), 7.12-7.14 (1H, m), 7.28-7.49 (10H, m). | 345 (ESI+) |

TABLE 8-continued
| Example | Structural formula | ¹H-NMR (CDCl₃) | MS |
|---|---|---|---|
| 12 | 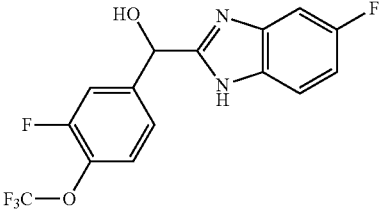 | δ: 6.01 (1H, s), 6.92-6.99 (1H, m), 7.08-7.21 (3H, m), 7.25-7.30 (1H, m), 7.32-7.37 (1H, m). | 345 (ESI+) |
| 13 | 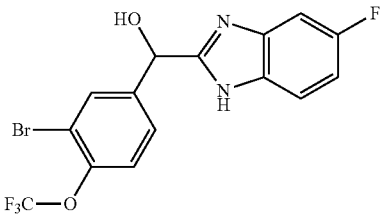 [SMILES: OC(c1ccc(OC(F)(F)F)c(Br)c1)c1nc2cc(F)ccc2[nH]1] | δ: 6.02 (1H, s), 6.94-7.01 (1H, m), 7.13-7.23 (2H, m), 7.36-7.41 (2H, m), 7.74 (1H, d, J = 2.0 Hz). | 405 (ESI+) |
| 14 | 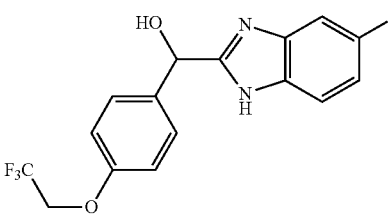 | δ: 4.18 (1H, d, J = 8.1 Hz), 4.23 (1H, d, J = 8.1 Hz), 5.94 (1H, s), 6.73 (2H, d, J = 8.8 Hz), 6.88-7.01 (2H, m), 7.23-7.25 (3H, m). | 341 (ESI+) |
| 15 | 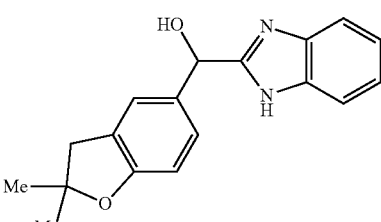 | δ: 1.40 (6H, s), 2.83 (2H, s), 5.91 (1H, s), 6.61 (1H, d, J = 8.9 Hz), 6.88-6.95 (1H, m), 7.05-7.09 (3H, m), 7.30-7.35 (1H, m). | 313 (ESI+) |
| 16 | 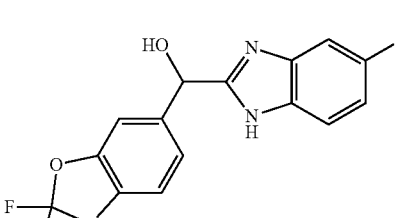 | δ: 5.99 (1H, s), 6.81 (1H, d, J = 8.5 Hz), 6.87-7.06 (4H, m), 7.24-7.29 (1H, m). | 323 (ESI+) |

Example 17

2-[Ethylsulfanyl(4-trifluoromethoxyphenyl)methyl]-5-fluoro-1H-benzimidazole

[Chemical formula 13]

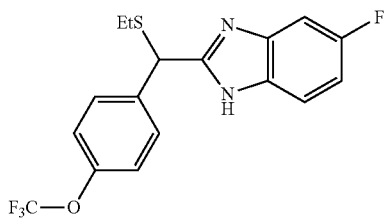

The compound of Example 1 (444 mg) was dissolved in THF (7 mL), and thionyl chloride (178 mg) and pyridine (247 mg) were added thereto. The mixture was stirred for 30 minutes at room temperature, and then ethanethiol (101 mg) and DIPEA (535 µL) were added thereto. The mixture was stirred for 1.5 hours at room temperature. After distilling off the solvent under reduced pressure, the residue was basified with a saturated aqueous solution of sodium hydrogen carbonate and extracted with chloroform. The organic layer was washed with saturated brine and then dried over anhydrous sodium sulfate. After distilling off the solvent under reduced pressure, the residue was purified by silica gel column chromatography (20% to 66% ethyl acetate/hexane), and thus the title compound (275 mg) was obtained as a colorless amorphous material.

$^1$H-NMR (CDCl$_3$) δ: 1.26 (3H, t, J=7.3 Hz), 2.46-2.64 (2H, m), 5.46 (1H, s), 6.98-7.72 (7H, m), 9.63 (1H, br s)

ESI-MS Found: m/z 371 (M+H)$^+$

Example 18

5-Fluoro-2-[pyridin-3-yloxy(4-trifluoromethoxyphenyl)methyl]-1H-benzimidazole

[Chemical formula 14]

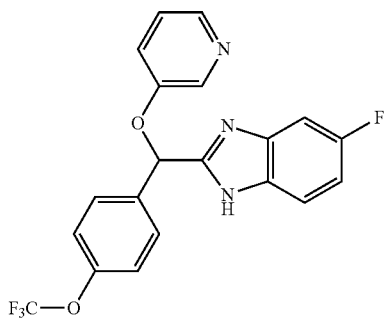 [SMILES: Fc1ccc2[nH]c(C(Oc3ccccc3)c3ccc(OC(F)(F)F)cc3)nc2c1]

The compound of Example 1 (150 mg) was dissolved in THF (5 mL), and thionyl chloride (60 mg) and pyridine (146 mg) were added thereto. The mixture was stirred for 30 minutes at room temperature, and then 3-hydroxypyridine (87 mg) and potassium hydroxide (65 mg) were added thereto. The mixture was heated to reflux for 30 minutes while being stirred. A 10% aqueous solution of sodium hydroxide was added to the reaction mixture, and the mixture was extracted with chloroform. The organic layer was washed with saturated brine and then dried over anhydrous sodium sulfate. After distilling off the solvent under reduced pressure, the residue was purified by silica gel column chromatography (60% to 100% ethyl acetate/hexane), and thus the title compound (19 mg) was obtained as a yellow amorphous material.

$^1$H-NMR (CDCl$_3$) δ: 6.61 (1H, s), 6.98-7.05 (1H, m), 7.22-7.27 (4H, m), 7.36-7.40 (1H, m), 7.47-7.55 (1H, m), 7.58 (2H, d, J=8.8 Hz), 8.17 (1H, d, J=2.6 Hz), 8.26 (1H, d, J=4.2 Hz).

ESI-MS Found: m/z 404 (M+H)$^+$

Example 19

2-[(2,2-Dimethyl-2,3-dihydrobenzofuran-5-yl)ethoxymethyl]-5-fluoro-1H-benzimidazole

[Chemical formula 15]

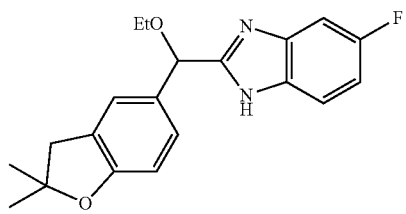

The compound of Example 15 (100 mg) was dissolved in THF (2 mL), and thionyl chloride (40 mg) and pyridine (28 mg) were added thereto. The mixture was stirred for 2 hours at room temperature. A 20% ethanol solution of sodium ethoxide (260 µL) was added to the reaction mixture, and the mixture was stirred at room temperature for one hour and at 50° C. for 2 hours. A saturated aqueous solution of sodium hydrogen carbonate was added to the reaction mixture, and the mixture was extracted with chloroform. The organic layer was washed with saturated brine and then dried over anhydrous sodium sulfate. After distilling off the solvent under reduced pressure, the residue was purified by silica gel column chromatography (25% to 75% ethyl acetate/hexane), and thus the title compound (31 mg) was obtained as a colorless amorphous material.

$^1$H-NMR (CDCl$_3$) δ: 1.27 (3H, t, J=7.0 Hz), 1.43 (6H, s), 2.92 (2H, s), 3.51-3.68 (2H, m), 5.58 (1H, s), 6.67 (1H, d, J=8.8 Hz), 6.93-7.16 (4H, m), 7.29-7.66 (1H, m), 9.81 (1H, br s).

ESI-MS Found: m/z 341 (M+H)$^+$

Example 20

2-[Ethanesulfonyl(4-trifluoromethoxyphenyl)methyl]-5-fluoro-1H-benzimidazole

[Chemical formula 16]

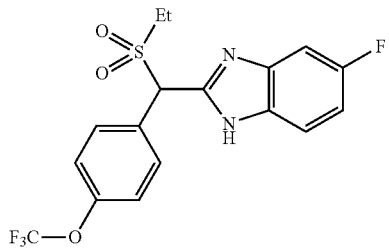

The compound of Example 17 (100 mg) was dissolved in dichloromethane (3 mL), and m-chloroperbenzoic acid (161 mg) was added thereto under ice cooling. The mixture was stirred for one hour at the same temperature. The reaction mixture was basified with a saturated aqueous solution of sodium hydrogen carbonate and extracted with chloroform. The organic layer was washed with saturated brine and then dried over anhydrous sodium sulfate. After distilling off the solvent under reduced pressure, the residue was purified by silica gel column chromatography (33% to 100% ethyl acetate/hexane), and thus the title compound (62 mg) was obtained as a colorless amorphous material.

$^1$H-NMR (CDCl$_3$) δ: 1.39 (3H, t, J=7.5 Hz), 3.01-3.26 (2H, m), 5.97 (1H, s), 7.03-7.10 (1H, m), 7.27 (2H, d, J=8.8 Hz), 7.41-7.59 (1.5H, m), 7.77 (2H, d, J=8.8 Hz), 8.00-8.12 (0.5H, m), 10.45 (1H, br s).

ESI-MS Found: m/z 404 (M+H)$^+$

Example 21

5-Fluoro-2-[isopropoxy(4-trifluoromethoxyphenyl)methyl]-1H-benzimidazole

[Chemical formula 17]

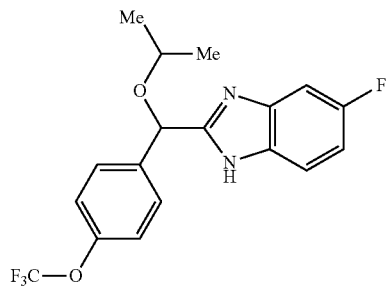

The compound of Example 1 (123 mg) was dissolved in isopropanol (2 mL), and concentrated sulfuric acid (41 mg) was added thereto. The mixture was heated at 140° C. for one hour and at 160° C. for 2 hours by means of a microwave reaction apparatus. The reaction mixture was basified with a 10% aqueous solution of sodium hydroxide and extracted with chloroform. The organic layer was washed with saturated brine and then dried over anhydrous sodium sulfate. After distilling off the solvent under reduced pressure, the residue was purified by silica gel column chromatography (10% to 100% ethyl acetate/hexane), and thus the title compound (66 mg) was obtained as a colorless solid.

$^1$H-NMR (CDCl$_3$) δ: 1.24-1.28 (6H, m), 3.76-3.84 (1H, m), 5.81 (1H, s), 6.95-7.04 (1H, m), 7.11 (0.5H, dd, J=8.6, 2.4 Hz), 7.20 (2H, d, J=8.4 Hz), 7.32-7.41 (1H, m), 7.50 (2H, d, J=8.4 Hz), 7.61-7.66 (0.5H, m), 9.44 (1H, br s).

ESI-MS Found: m/z 369 (M+H)$^+$

Example 22

2-[Benzyloxy(4-trifluoromethoxyphenyl)methyl]-5-fluoro-1H-benzimidazole

[Chemical formula 18]

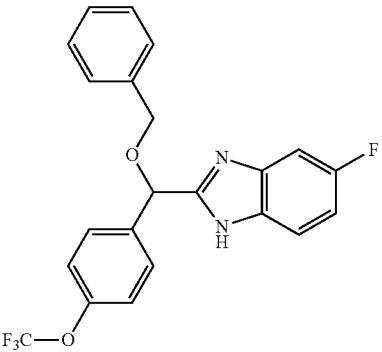

The title compound (66 mg) was obtained as a colorless solid, in the same manner as described in Example 21 by using the compound of Example 1 (116 mg) and benzyl alcohol (2 mL).

$^1$H-NMR (CDCl$_3$) δ: 4.57 (1H, d, J=11.5 Hz), 4.67 (1H, d, J=11.5 Hz), 5.79 (1H, s), 6.97-7.03 (1H, m), 7.08-7.11 (0.5H, m), 7.22 (2H, d, J=8.5 Hz), 7.32-7.41 (6H, m), 7.50 (2H, d, J=8.5 Hz), 7.60-7.68 (0.5H, m), 9.49 (1H, br s).

ESI-MS Found: m/z 417 (M+H)$^+$

Examples 23 to 36

Compounds 23 to 33 that were produced in the same manner as described in Example 21 by using corresponding raw materials, are shown in Tables 9 and 10.

TABLE 9

| Example | Structural formula | $^1$H-NMR (CDCl$_3$) | MS |
|---|---|---|---|
| 23 | (cyclohexyloxy-(4-trifluoromethoxyphenyl)methyl-5-fluoro-1H-benzimidazole structure) | δ: 1.26-1.56 (6 H, m), 1.73-1.75 (2H, m), 1.91-1.95 (2H, m), 3.44-3.53 (1H, m), 5.86 (1H, s), 6.95-7.04 (1H, m), 7.12 (0.5H, dd, J = 8.6, 2.2 Hz), 7.19 (2H, d, J = 8.6 Hz), 7.33-7.41 (1H, m), 7.50 (2H, d, J = 8.6 Hz), 7.62-7.66 (0.5H, m), 9.43 (1H, br s). | 409 (ESI+) |

TABLE 9-continued

| Example | Structural formula | ¹H-NMR (CDCl₃) | MS |
|---|---|---|---|
| 24 | (structure: 4-(F₃CO)-phenyl-CH(OCH₂CH₂OMe)-benzimidazole-5-F) | δ: 3.48 (3H, s), 3.55-3.66 (1H, m), 3.71-3.78 (2H, m), 3.84-3.92 (1H, m), 5.76 (1H, s), 6.96-7.03 (1H, m), 7.19-7.22 (3H, m), 7.49-7.52 (3H, m). | 385 (ESI+) |
| 25 | (structure: 4-(F₃CO)-phenyl-CH(OPh)-benzimidazole-5-F) | δ: 5.53 (1H, s), 6.85-7.24 (11H, m), 7.41-7.58 (1H, m). | 403 (ESI+) |
| 26 | (structure: 4-(F₃CO)-phenyl-CH(OCH₂CF₃)-benzimidazole-5-F) | δ: 3.86-4.05 (2H, m), 5.86 (1H, s), 6.99-7.06 (1H, m), 7.15-7.25 (3H, m), 7.45-7.62 (3H, m), 9.67 (1H, br s). | 409 (ESI+) |
| 27 | (structure: 4-(F₃C)-phenyl-CH(OEt)-benzimidazole-5-F) | δ: 1.33 (3H, t, J = 7.1 Hz), 3.61-3.70 (2H, m), 5.74 (1H, s), 6.97-7.65 (7H, m), 9.41 (1H, s). | 339 (ESI+) |

TABLE 10

| Example | Structural formula | ¹H-NMR (CDCl₃) | MS |
|---|---|---|---|
| 28 | (structure: 3-Br-4-(F₃CO)-phenyl-CH(OEt)-benzimidazole-5-F) | δ: 1.33 (3H, t, J = 7.0 Hz), 3.60-3.70 (2H, m), 5.66 (1H, s), 6.98-7.05 (1H, m), 7.11-7.15 (0.5H, m), 7.27-7.45 (3H, m), 7.62-7.67 (0.5H, m), 7.76 (1H, d, J = 2.0 Hz), 9.45 (1H, br s). | 433 (ESI+) |

TABLE 10-continued

| Example | Structural formula | ¹H-NMR (CDCl₃) | MS |
|---|---|---|---|
| 29 | (EtO, 3-F, 4-OCF₃-phenyl / 5-F-benzimidazole) | δ: 1.33 (3H, t, J = 7.0 Hz), 3.61-3.71 (2H, m), 5.67 (1H, s), 6.97-7.13 (1.5H, m), 7.28-7.41 (4H, m), 7.63-7.67 (0.5H, m), 9.44 (1H, br s). | 373 (ESI+) |
| 30 | (MeO, 4-OCH₂CF₃-phenyl / 5-F-benzimidazole) | δ: 3.45 (3H, s), 4.30 (1H, d, J = 8.1 Hz), 4.35 (1H, d, J = 8.1 Hz), 5.52 (1H, s), 6.90-7.68 (7H, m), 9.52 (1H, br s). | 355 (ESI+) |
| 31 | (EtO, 4-OCH₂CF₃-phenyl / 5-F-benzimidazole) | δ: 1.30 (3H, t, J = 7.0 Hz), 3.56-3.66 (2H, m), 4.29 (1H, d, J = 8.1 Hz), 4.35 (1H, d, J = 8.2 Hz), 5.64 (1H, s), 6.91-7.62 (7H, m), 9.49 (1H, br s). | 369 (ESI+) |
| 32 | (EtO, 2,2-difluoro-1,3-benzodioxol-5-yl / 5-F-benzimidazole) | δ: 1.32 (3H, t, J = 7.0 Hz), 3.56-3.68 (2H, m), 5.64 (1H, s), 6.96-7.66 (6H, m), 9.46 (1H, br s). | 351 (ESI+) |
| 33 | (MeO, 2,2-difluoro-1,3-benzodioxol-5-yl / 5-F-benzimidazole) | *DMSO-d₆ was used as a solvent. δ: 3.36 (3H, s), 5.64 (1H, s), 6.94-7.06 (1H, br m), 7.18-7.55 (5H, m), 12.64 (1H, br s). | 335 (ESI−) |

Example 34

(4-Benzyloxyphenyl)-(5-methoxy-1H-benzimidazol-2-yl)methanol

[Chemical formula 19]

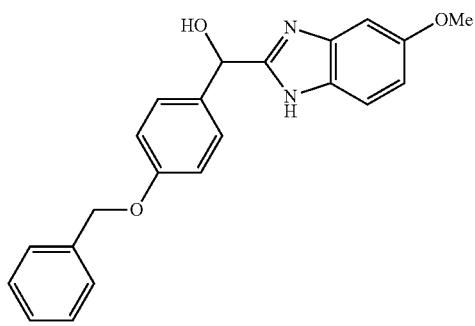

The compound of Reference Example 4 (200 mg) was dissolved in THF (1 mL), and 1 mol/L hydrochloric acid (1 mL) was added thereto under ice cooling. The mixture was stirred for 30 minutes at room temperature. After distilling off the solvent under reduced pressure, the residue was diluted with a saturated aqueous solution of sodium hydrogen carbonate and extracted with ethyl acetate. The organic layer was washed with saturated brine and then dried over anhydrous sodium sulfate. After distilling off the solvent solvent under reduced pressure, the residue was purified by silica gel column chromatography (20% to 100% ethyl acetate/hexane), and thus the title compound (65 mg) was obtained as a pale yellow amorphous material.

$^1$H-NMR (CDCl$_3$) δ: 3.83 (3H, s), 5.06 (2H, s), 5.98 (1H, s), 6.85-7.45 (12H, m).

ESI-MS Found: m/z 361 (M+H)$^+$

Example 35

2-[(4-Benzyloxyphenyl)morpholin-4-ylmethyl]-5-methoxy-1H-benzimidazole

[Chemical formula 20]

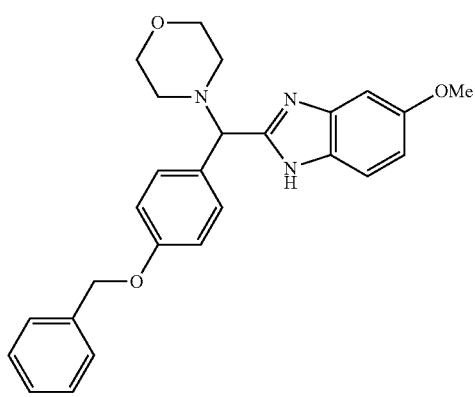

The compound of Reference Example 4 (150 mg) was dissolved in dichloromethane, and triethylamine (98 mg) and methanesulfonyl chloride (56 mg) were sequentially added thereto under ice cooling. The mixture was stirred for 30 minutes at the same temperature. Still at the same temperature, morpholine (85 mg) was added dropwise to the reaction mixture, and the mixture was stirred for 30 minutes. A saturated aqueous solution of ammonium chloride was added to the reaction mixture, and the mixture was extracted with ethyl acetate. The organic layer was washed with saturated brine and then dried over anhydrous sodium sulfate. After distilling off the solvent under reduced pressure, the residue was dissolved in THF (4 mL), and 1 mol/L hydrochloric acid (2 mL) was added thereto under ice cooling. The mixture was stirred for 30 minutes at the same temperature. The reaction mixture was basified with a 1 mol/L aqueous solution of sodium hydroxide and extracted with ethyl acetate. The organic layer was washed with saturated brine and then dried over anhydrous sodium sulfate. After distilling off the solvent under reduced pressure, the residue was purified by basic silica gel column chromatography (10% to 30% ethyl acetate/hexane), and thus the title compound (75 mg) was obtained as a colorless amorphous material.

$^1$H-NMR (CDCl$_3$) δ: 2.32-2.42 (2H, m), 2.51-2.58 (2H, m), 3.70-3.75 (4H, m), 3.82 (3H, s), 4.64 (1H, s), 5.02 (2H, s), 6.83-7.58 (12H, m), 9.37-9.41 (1H, br m).

ESI-MS Found: m/z 430 (M+H)$^+$

Example 36

2-[(4-Benzyloxyphenyl)pyrrolidin-1-ylmethyl]-5-methoxy-1H-benzimidazole

[Chemical formula 21]

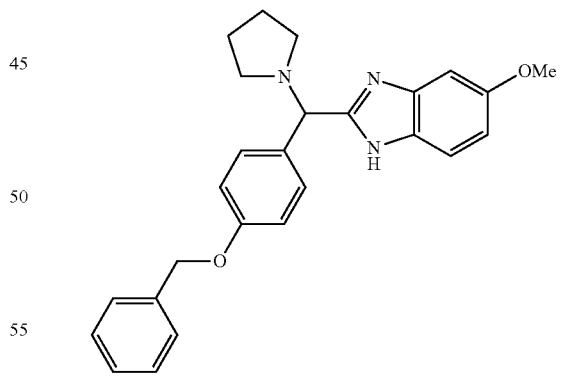

The title compound (12 mg) was obtained as a colorless solid, in the same manner as described in Example 35 by using the compound of Reference Example 4 (114 mg) and pyrrolidine (88 mg).

$^1$H-NMR (CDCl$_3$) δ: 1.62-1.68 (2H, m), 1.77-1.83 (2H, m), 2.45-2.52 (2H, m), 2.53-2.58 (2H, m), 3.82 (3H, s), 4.62 (1H, s), 5.02 (2H, s), 6.82-7.57 (12H, m), 9.42 (1H, br s).

ESI-MS Found: m/z 412 (M−H)$^−$

Example 37

2-[(4-Benzyloxyphenyl)ethylsulfanylmethyl]-5-methoxy-1H-benzimidazole

[Chemical formula 22]

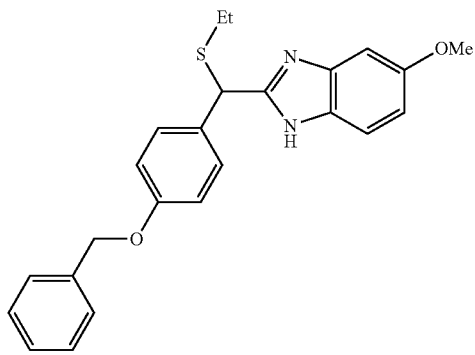

The title compound (115 mg) was obtained as a colorless solid, in the same manner as described in Example 35 by using the compound of Reference Example 4 (150 mg) and ethanethiol (60 mg).

$^1$H-NMR (CDCl$_3$) δ: 1.24 (3H, t, J=7.4 Hz), 2.53 (2H, q, J=7.4 Hz), 3.83 (3H, s), 5.02 (2H, s), 5.44 (1H, s), 6.86-7.40 (12H, m).

ESI-MS Found: m/z 405 (M+H)$^+$

Examples 38 to 41

Compounds 38 to 41 that were produced in the same manner as described in Example 35 by using corresponding raw materials, are shown in Table 11.

TABLE 11

| Example | Structural formula | $^1$H-NMR (CDCl$_3$) | MS |
|---|---|---|---|
| 38 | | δ: 1.03 (6H, t, J = 7.1 Hz), 2.49 (2H, q, J = 7.1, Hz), 2.64 (2H, q, J = 7.1, Hz), 3.82 (3H, s), 5.03 (2H, s), 5.08 (1H, br s), 6.82-7.58 (12H, m), 9.43 (1H, br s). | 416 (ESI+) |
| 39 | | δ: 1.37 (3H, t, J = 7.4 Hz), 2.43-2.51 (2H, m), 2.57-2.66 (2H, m), 2.95 (2H, q, J = 7.4, Hz), 3.30-3.35 (4H, m), 3.82 (3H, s), 4.70-4.74 (1H, m), 5.03 (2H, s), 6.84-7.60 (12H, m), 9.21-9.28(1H, br m). | 521 (ESI+) |

TABLE 11-continued

| Example | Structural formula | $^1$H-NMR (CDCl$_3$) | MS |
|---|---|---|---|
| 40 | | δ: 1.42 (3H, t, J = 7.0 Hz), 2.24 (6H, s), 4.04 (2H, q, J = 7.0 Hz), 4.57 (1H, s), 5.07 (2H, s), 6.82-7.57 (10H, m), 9.34-9.44 (1H, br m). | 436 (ESI−) |
| 41 | | δ: 0.37-0.45 (4H, m), 1.42 (3H, t, J = 7.0 Hz), 2.17-2.24 (1H, m), 4.04 (2H, q, J = 7.0 Hz), 5.06-5.07 (2H, m), 5.12 (1H, s), 6.78-7.56 (10H, m), 9.23-9.29 (1H, br m). | 450 (ESI+) |

Example 42

2-[(4-Benzyloxyphenyl)ethanesulfonylmethyl]-5-methoxy-1H-benzimidazole

[Chemical formula 23]

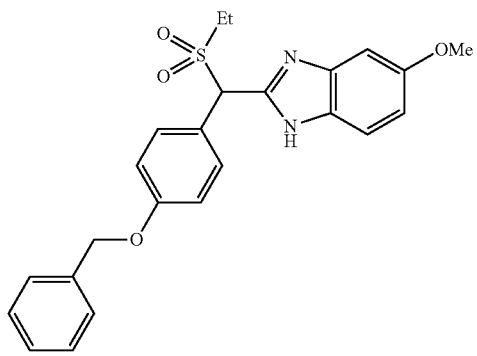

The compound of Example 37 (30 mg) was dissolved in methanol (2 mL), and water (1 mL) was added thereto. Subsequently, Oxone (registered trademark, DuPont Co., 55 mg) was added thereto, and the mixture was heated for 3 hours at 40° C. Methanol was distilled off under reduced pressure, water was added to the reaction mixture, and the mixture was extracted with ethyl acetate. The organic layer was washed with saturated brine and then dried over anhydrous sodium sulfate. After distilling off solvent under reduced pressure, the residue was purified by basic silica gel column chromatography (20% to 100% ethyl acetate/hexane), and thus the title compound (10 mg) was obtained as a colorless solid.

$^1$H-NMR (CDCl$_3$) δ: 1.37 (3H, t, J=7.4 Hz), 3.07 (2H, q, J=7.4 Hz), 3.84 (3H, s), 5.05 (2H, s), 5.73 (1H, s), 6.90-7.62 (12H, m), 10.08 (1H, br s).

ESI-MS Found: m/z 437 (M+H)$^+$

Example 43

(5-Fluoro-1H-benzimidazol-2-yl)-(4-phenethylphenyl)methanol

[Chemical formula 24]

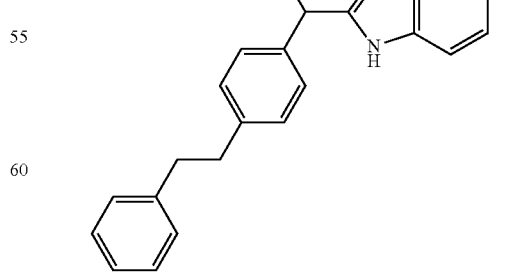

The compound of Example 11 (200 mg) was dissolved in methanol (6 mL), and 5% palladium-carbon (282 mg) was added thereto. The mixture was stirred for 67 hours at room temperature under a hydrogen gas stream (1 atm). The reaction mixture was diluted with chloroform, and the dilution was subjected to Celite filtration After distilling off the solvent under reduced pressure, the residue thus obtained was purified by silica gel column chromatography (47% to 61% ethyl acetate/hexane), and thus the title compound (98 mg) was obtained as a yellow amorphous material.

$^1$H-NMR (CDCl$_3$) δ: 2.88 (4H, s), 6.01 (1H, s), 6.92-6.99 (1H, m), 7.12-7.25 (7H, m), 7.26-7.43 (4H, m).

ESI-MS Found: m/z 347 (M+H)$^+$

Example 44

(6-Chloro-3H-imidazo[4,5-b]pyridin-2-yl)-(4-trifluoromethoxyphenyl)methanol

[Chemical formula 25]

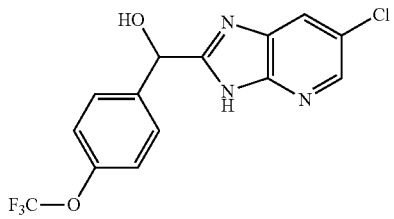

The compound of Reference Example 9 (682 mg) was dissolved in THF (10 mL), and 4.5 mL of a 2 mol/L aqueous hydrochloric acid solution was added thereto. The mixture was stirred at 75° C. for 10 minutes and at 100° C. for 10 minutes by means of a microwave reaction apparatus. The reaction mixture was basified with a 10% aqueous solution of sodium hydroxide and extracted with ethyl acetate. The organic layer was washed with saturated brine and then dried over anhydrous sodium sulfate. After distilling off the solvent under reduced pressure, the residue was purified by silica gel column chromatography (3% to 20% methanol/chloroform). The solid thus obtained was suspended in diethyl ether and then collected by filtration. Thus, the title compound (457 mg) was obtained as a colorless solid.

$^1$H-NMR (DMSO-d$_6$) δ: 5.99 (1H, s), 6.75 (1H, br s), 7.35 (2H, d, J=8.4 Hz), 7.62 (2H, d, J=8.4 Hz), 7.91-8.07 (1H, m), 8.29 (1H, s), 12.92-13.38 (1H, m).

ESI-MS Found: m/z 342 (M−H)$^−$

Examples 45 to 50

Compounds 45 to 50 that were produced in the same manner as described in Example 44 by using corresponding raw materials, are shown in Table 12.

TABLE 12

| Example | Structural formula | $^1$H-NMR(DMSO-d$_6$) | MS |
|---|---|---|---|
| 45 | ![structure with NO2] | δ: 6.06 (1H, d, J = 4.0 Hz), 6.86 (1H, br s), 7.36 (2H, d, J = 8.1 Hz), 7.60-7.73 (3H, m), 8.07-8.10 (1H, m), 8.31-8.43 (1H, m), 13.17 (1H, br s). | 342 (ESI−) |
| 46 | ![structure with Cl] | δ: 6.02 (1H, br s), 6.71-6.83 (1H, br m), 7.24 (1H, dd, J = 8.2, 1.4 Hz), 7.35 (2H, d, J = 8.2 Hz), 7.61 (2H, d, J = 8.2 Hz), 7.86-7.98 (1H, br m), 12.99-13.34 (1H, br m). | 344 (ESI+) |
| 47 | ![structure with S-n-Pr] | δ: 0.89-0.96 (3H, m), 1.44-1.58 (2H, m), 2.82-2.89 (2H, m), 5.95 (1H, d, J = 4.3 Hz), 6.65 (1H, d, J = 4.3 Hz), 7.10-7.19 (1H, m), 7.30-7.55 (4H, m), 7.59 (2H, d, J = 8.6 Hz), 12.39-12.48 (1H, m). | 381 (ESI−) |

TABLE 12-continued

| Example | Structural formula | ¹H-NMR(DMSO-d₆) | MS |
|---|---|---|---|
| 48 | | δ: 2.27 (3H, s), 5.01 (2H, s), 5.81-5.87 (1H, m), 6.41-6.51 (1H, m), 6.95 (2H, d, J = 8.4 Hz), 7.16 (2H, d, J = 7.8 Hz), 7.29 (2H, d, J = 7.8 Hz), 7.37-7.39 (2H, m), 7.62-7.90 (1H, m), 8.23-8.28 (1H, m), 12.76-13.19 (1H, m). | 362 (ESI-) |
| 49 | | δ: 5.92-6.05 (1H, m), 6.59-6.78 (1H, m), 7.13-7.20 (1H, m), 7.31-7.39 (2H, m), 7.62 (2H, d, J = 8.4 Hz), 7.77-7.95 (1H, m), 8.22-8.32 (1H, m), 12.66-13.12 (1H, m). | 308 (ESI-) |
| 50 | | δ: 5.96-5.99 (1H, m), 6.77-6.82 (1H, m), 7.32 (1H, dd, J = 8.2, 1.4 Hz), 7.38 (1H, d, J = 8.2 Hz), 7.51-7.54 (1H, m), 7.92-8.07 (1H, m), 8.28-8.31 (1H, m), 12.91-13.34 (1H, m). | 338 (ESI-) |

Example 51

[5-(Propane-1-sulfonyl)-1H-benzimidazol-2-yl]-(4-trifluoromethoxyphenyl)methanol

[Chemical formula 26]

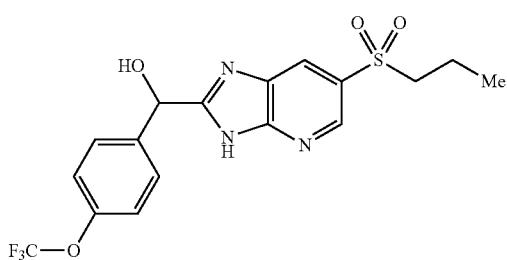

The compound of Reference Example 12 (300 mg) was dissolved in dichloromethane (6 mL), and m-chloroperbenzoic acid (440 mg) was added thereto under ice cooling. The mixture was stirred for one hour at the same temperature. The reaction mixture was basified with a saturated aqueous solution of sodium hydrogen carbonate and extracted with chloroform. The organic layer was washed with saturated brine and then dried over anhydrous sodium sulfate. After distilling off the solvent under reduced pressure, the residue was purified by silica gel column chromatography (12% to 90% ethyl acetate/hexane), and thus [1-methoxymethyl-5-(propanyl-1-sulfonyl)-1H-benzimidazol-2-yl]-(4-trifluoromethoxyphenyl)methanol (220 mg) was obtained as colorless amorphous material.

[1-Methoxymethyl-5-(propanyl-1-sulfonyl)-1H-benzimidazol-2-yl]-(4-trifluoromethoxyphenyl)methanol (220 mg) thus obtained was dissolved in ethanol (2 mL), and concentrated sulfuric acid (45 mg) was added thereto. The mixture was heated to reflux for 3 hours while being stirred. The reaction mixture was basified with a saturated aqueous solution of sodium hydrogen carbonate and extracted with chloroform. The organic layer was washed with saturated brine and then dried over anhydrous sodium sulfate. After distilling off the solvent under reduced pressure, the residue was purified by silica gel column chromatography (33% to 100% ethyl acetate/hexane), and thus the title compound (71 mg) was obtained as a colorless solid.

¹H-NMR (DMSO-d₆) δ: 0.86 (3H, t, J=7.2 Hz), 1.45-1.55 (2H, m), 3.15-3.29 (2H, m), 6.03-6.06 (1H, m), 6.78-6.85 (1H, m), 7.36 (2H, d, J=8.4 Hz), 7.60-7.77 (4H, m), 7.92-8.02 (1H, m), 13.02-13.04 (1H, br m).

ESI-MS Found: m/z 413 (M-H)⁻

Example 52

2-{Ethoxy[4-(4-fluorobenzyloxy)phenyl]methyl}-3H-imidazo[4,5-b]pyridine

[Chemical formula 27]

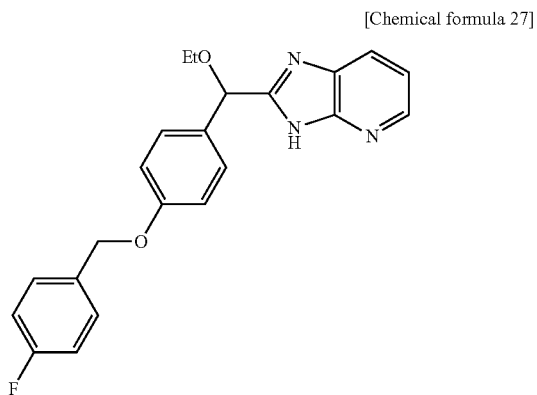 [SMILES: CCOC(c1ccc(OCc2ccc(F)cc2)cc1)c1nc2cccnc2[nH]1]

The compound of Reference Example 14 (5.6 g) was dissolved in toluene (45 mL), and silver (I) oxide (6.6 g) and iodoethane (5.6 mL) were added thereto. The mixture was heated for 1.5 hours at 70° C. The reaction mixture was diluted with chloroform, the dilution was subjected to Celite filtration. After distilling off the the solvent under reduced pressure, the residue was dissolved in ethanol (71 mL), and concentrated sulfuric acid (1.5 g) was added thereto. The mixture was heated to reflux for 2 hours while being stirred. The reaction mixture was basified with a 10% aqueous solution of sodium hydroxide and extracted with chloroform. The organic layer was washed with saturated brine and then dried over anhydrous sodium sulfate. After distilling off the solvent under reduced pressure, the residue was purified by silica gel column chromatography (50% to 100% ethyl acetate/hexane). The solid thus obtained was suspended in diethyl ether and was collected by filtration. Thus, the title compound (4.4 g) was obtained as a colorless solid.

$^1$H-NMR (DMSO-$d_6$) δ: 1.17-1.23 (3H, m), 3.47-3.56 (2H, m), 5.05 (2H, s), 5.60-5.69 (1H, m), 6.99 (2H, d, J=8.2 Hz), 7.16-7.22 (3H, m), 7.37-7.49 (4H, m), 7.80-7.94 (1H, m), 8.24-8.32 (1H, m), 12.66-13.13 (1H, m).

ESI-MS Found: m/z 378 (M+H)$^+$

Examples 53 to 59

Compounds 53 to 59 that were produced in the same manner as described in Example 52 by using corresponding raw materials, are shown in Tables 13 and 14.

TABLE 13

| Example | Structural formula | $^1$H-NMR (CDCl$_3$) | MS |
|---|---|---|---|
| 53 | (EtO, imidazo[4,5-b]pyridine with 6-Cl, phenyl-O-CF$_3$) | δ: 1.34 (3H, t, J = 7.1 Hz), 3.63-3.74 (2H, m), 5.71 (1H, s), 7.22 (2H, d, J = 8.8 Hz), 7.53 (2H, d, J = 9.8 Hz), 8.00 (1H, d, J = 2.2 Hz), 8.35 (1H, d, J = 2.2 Hz), 11.39 (1H, s). | 372 (ESI+) |
| 54 | (EtO, imidazo[4,5-b]pyridine with 5-Cl, phenyl-O-CF$_3$) | δ: 1.32 (3H, t, J = 7.0 Hz), 3.57-3.73 (2H, m), 5.67-5.82 (1H, m), 7.19-7.24 (3H, m), 7.46-7.54 (2H, m), 7.69-7.94 (1H, m), 9.81 (1H, br s). | 370 (ESI−) |
| 55 | (EtO, imidazo[4,5-b]pyridine, phenyl-O-CH$_2$-phenyl-Me) | *DMSO-$d_6$ was used as a solvent. δ: 1.20 (3H, t, J = 7.0 Hz), 2.27 (3H, s), 3.51 (2H, q, J = 7.0 Hz), 5.02 (2H, s), 5.63 (1H, br s), 6.96-7.19 (5H, m), 7.29 (2H, d, J = 7.9 Hz), 7.38 (2H, d, J = 8.4, Hz), 7.76-7.96 (1H, m), 8.23-8.33 (1H, m), 12.68-13.13 (1H, m). | 374 (ESI+) |

TABLE 13-continued

| Example | Structural formula | ¹H-NMR (CDCl₃) | MS |
|---|---|---|---|
| 56 | (structure) | δ: 1.31 (3H, t, J = 7.0 Hz), 2.34 (3H, s), 3.58-3.77 (2H, m), 4.98 (2H, s), 5.67 (1H, s), 6.95 (2H, d, J = 8.8 Hz), 7.16 (2H, d, J = 8.1 Hz), 7.28 (2H, d, J = 8.1 Hz), 7.40 (2H, d, J = 8.8 Hz), 8.00 (1H, d, J = 2.2 Hz), 8.37 (1H, d, J = 2.2 Hz), 12.28-12.47 (1H, br m). | 408 (ESI+) |
| 57 | (structure) | *DMSO-d₆ was used as a solvent. δ: 1.20 (3H, t, J = 6.8 Hz), 2.28 (3H, s), 3.51 (2H, q, J = 6.8 Hz), 5.02 (2H, s), 5.60-5.66 (1H, br m), 6.97 (2H, d, J = 8.0 Hz), 7.16 (2H, d, J = 8.0 Hz), 7.29 (2H, d, J = 8.0 Hz), 7.38 (2H, d, J = 8.0 Hz), 7.78-7.86 (1H, br m), 8.26-8.30 (1H, br m), 12.82-13.30 (1H, br m). | 390 (ESI+) |

TABLE 14

| Example | Structural formula | ¹H-NMR (CDCl₃) | MS |
|---|---|---|---|
| 58 | (structure) | δ: δ: 1.32 (3H, t, J = 7.1 Hz), 3.61-3.75 (2H, m), 4.99 (2H, s), 5.68 (1H, s), 6.93-7.09 (4H, m), 7.34-7.43 (4H, m), 7.99-8.02 (1H, m), 8.36-8.37 (1H, m), 12.30-12.38 (1H, br m). | 412 (ESI+) |
| 59 | (structure) | *DMSO-d₆ was used as a solvent. δ: 1.20 (3H, t, J = 7.0 Hz), 3.51 (2H, q, J = 7.0 Hz), 5.05 (2H, s), 5.60-5.67 (1H, m), 6.99 (2H, d, J = 8.7 Hz), 7.15-7.23 (2H, m), 7.39 (2H, d, J = 8.7 Hz), 7.43-7.49 (2H, m), 7.70-7.89 (1H, m), 8.27-8.30 (1H, m), 12.80-13.32 (1H, m). | 392 (ESI+) |

Example 60

2-{[4-(2,5-Difluorobenzyloxy)phenyl]ethoxymethyl}-5-ethoxy-1H-benzimidazole

[Chemical formula 28]

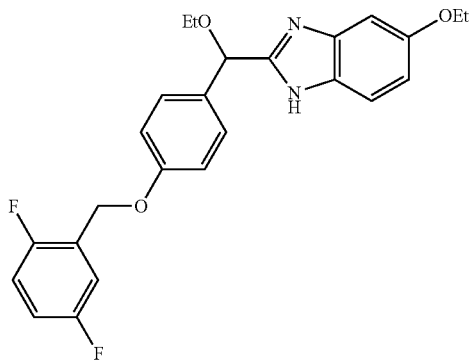

The compound of Reference Example 23 (2.0 g) was dissolved in dichloromethane (25 mL), and EDC (1.4 g), HOBt (1.1 g) and 4-ethoxy-1,2-phenylenediamine (1.0 g) were sequentially added thereto under ice cooling. The mixture was stirred for 12 hours at room temperature. A saturated aqueous solution of sodium hydrogen carbonate was added to the reaction mixture, and the mixture was extracted with chloroform. The organic layer was washed with saturated brine and then dried over anhydrous sodium sulfate. After distilling off the solvent under reduced pressure, the residue was purified by silica gel column chromatography (20% to 50% ethyl acetate/hexane), and thus an amide form (2.3 g) was obtained as a regioisomer mixture.

The amide form (2.3 g) thus obtained was dissolved in acetic acid (40 mL), and the mixture was heated for 30 minutes at 100° C. After distilling off the solvent under reduced pressure, the residue was diluted with water. The mixture was basified with a saturated aqueous solution of sodium hydrogen carbonate and extracted with ethyl acetate. The organic layer was washed with saturated brine and then dried over anhydrous sodium sulfate. After distilling off the solvent under reduced pressure, the residue was purified by basic silica gel column chromatography (10% to 35% ethyl acetate/hexane), and thus the title compound (1.5 g) was obtained as a colorless solid.

$^1$H-NMR (CDCl$_3$) δ: 1.28 (3H, t, J=7.1 Hz), 1.42 (3H, t, J=7.0 Hz), 3.53-3.69 (2H, m), 4.04 (2H, q, J=7.0 Hz), 5.07 (2H, s), 5.62 (1H, s), 6.87-7.51 (10H, m), 9.34 (1H, br).

ESI-MS Found: m/z 439 (M+H)$^+$

Examples 61 to 64

Compounds 61 to 64 that were produced in the same manner as described in Example 60 by using corresponding raw materials, are shown in Table 15.

TABLE 15

| Example | Structural formula | $^1$H-NMR (CDCl$_3$) | MS |
|---|---|---|---|
| 61 | | δ: 1.29 (3H, t, J = 7.1 Hz), 3.53-3.69 (2H, m), 5.08 (2H, s), 5.63 (1H, s), 6.96-7.04 (4H, m), 7.18-7.23 (2H, m), 7.30-7.40 (3H, m), 7.62-7.66 (1H, m), 9.49 (1H, br s). | 429 (ESI+) |
| 62 | | *CD$_3$OD was used as a solvent. δ: 1.29 (3H, t, J = 7.0 Hz), 3.54-3.63 (2H, m), 5.11 (2H, s), 5.62 (1H, s), 6.97-7.51 (11H, m). | 395 (ESI+) |

TABLE 15-continued

| Example | Structural formula | $^1$H-NMR (CDCl$_3$) | MS |
|---|---|---|---|
| 63 | | δ: 1.30 (3H, t, J = 7.0 Hz), 3.54-3.71 (2H, m), 5.08 (2H, s), 5.67 (1H, s), 6.93-7.90 (10H, m), 9.67-9.74 (1H, br m). | 463 (ESI+) |
| 64 | | δ: 1.27 (3H, t, J = 7.0 Hz), 3.51-3.64 (2H, m), 5.04 (2H, s), 5.62 (1H, s), 6.69-7.47 (10H, m), 9.27 (1H, br). | 411 (ESI+) |

Example 65

2-{[4-(2,5-Difluorobenzyloxy)phenyl]ethoxymethyl}-5-fluoro-1H-benzimidazole

[Chemical formula 29]

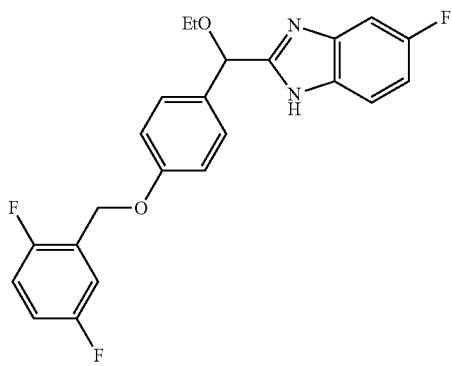

The compound of Reference Example 23 (300 mg) was dissolved in DMF (4 mL), and HATU (425 mg), 4-fluoro-1,2-phenylenediamine (129 mg), and DIPEA (289 mg) were sequentially added to this solution. The mixture was stirred for 4 hours at room temperature. After distilling off the solvent under reduced pressure, the residue was diluted with water, and the mixture was extracted with ethyl acetate. The organic layer was washed with saturated brine and then dried over anhydrous sodium sulfate. After distilling off the solvent under reduced pressure, the residue was purified by silica gel column chromatography (10% to 40% ethyl acetate/hexane), and thus an amide form was obtained as a regioisomer mixture.

The amide form (377 mg) thus obtained was dissolved in acetic acid (6 mL), and the mixture was heated for one hour at 80° C. After distilling off the solvent under reduced pressure, the residue was diluted with water. The dilution was adjusted from neutrality to basicity with a saturated aqueous solution of sodium hydrogen carbonate and extracted with ethyl acetate. The organic layer was washed with saturated brine and then dried over anhydrous sodium sulfate. After distilling off the solvent under reduced pressure, the residue was purified by silica gel column chromatography (10% to 40% ethyl acetate/hexane), and thus the title compound (300 mg) was obtained as a colorless solid.

$^1$H-NMR (CDCl$_3$) δ: 1.29 (3H, t, J=7.0 Hz), 3.53-3.69 (2H, m), 5.08 (2H, s), 5.63 (1H, s), 6.93-7.11 (5H, m), 7.18-7.23 (1H, m), 7.31-7.65 (4H, m), 9.49 (1H, br).

ESI-MS Found: m/z 413 (M+H)$^+$

Example 66

2-{[4-(2,5-Difluorobenzyloxy)phenyl]ethoxymethyl}-5-methoxy-1H-benzimidazole

[Chemical formula 30]

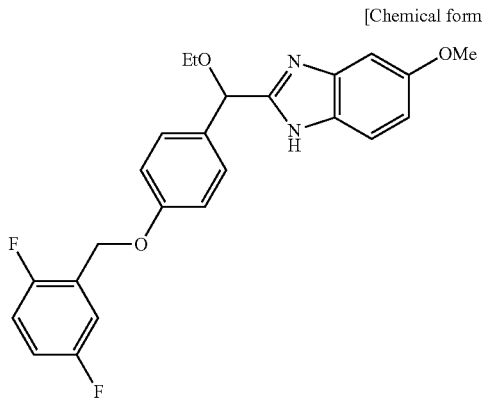

The title compound (179 mg) was obtained as a colorless solid, in the same manner as described in Example 65 by using the compound of Reference Example 23 (300 mg) and 4-methoxy-1,2-phenylenediamine (216 mg).

$^1$H-NMR (CDCl$_3$) δ: 1.29 (3H, t, J=7.1 Hz), 3.53-3.69 (2H, m), 3.83 (3H, s), 5.08 (2H, s), 5.63 (1H, s), 6.84-7.23 (7H, m), 7.28-7.61 (3H, m), 9.31-9.35 (1H, br).

ESI-MS Found: m/z 425 (M+H)$^+$

Example 67

8-{([4-(2,5-Difluorobenzyloxy)phenyl]ethoxymethyl}-7H-purine

[Chemical formula 31]

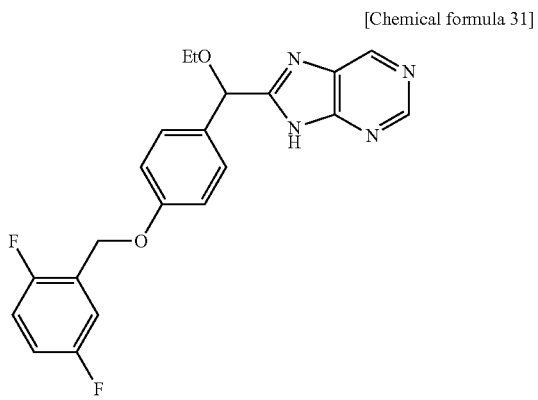 [SMILES: CCOC(c1ccc(OCc2cc(F)ccc2F)cc1)c1nc2ccncc2[nH]1]

The title compound (40 mg) was obtained as a colorless solid, in the same manner as described in Example 65 by using the compound of Reference Example 23 (300 mg) and 4,5-diaminopyrimidine (113 mg).

$^1$H-NMR (CDCl$_3$) δ: 1.33 (3H, t, J=7.1 Hz), 3.60-3.78 (2H, m), 5.08 (2H, s), 5.72 (1H, s), 6.96-7.07 (4H, m), 7.16-7.22 (1H, m), 7.42-7.45 (2H, m), 9.02 (1H, s), 9.09 (1H, s), 12.12 (1H, br).

ESI-MS Found: m/z 397 (M+H)$^+$

Example 68

2-{[4-(2,5-Difluorobenzyloxy)phenyl]ethoxymethyl}-3H-imidazo[4,5-c]pyridine

[Chemical formula 32]

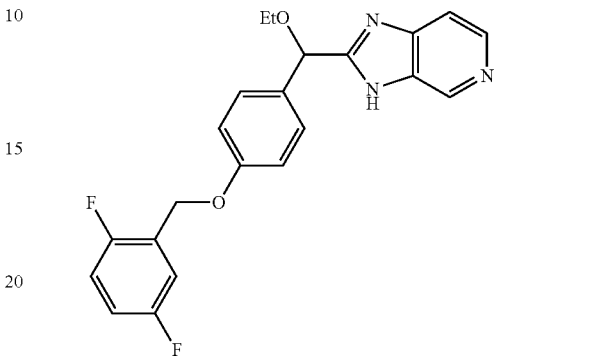

The title compound (194 mg) was obtained as a colorless oily material, in the same manner as described in Example 65 by using the compound of Reference Example 23 (200 mg) and 3,4-diaminopyridine (75 mg).

$^1$H-NMR (CDCl$_3$) δ: 1.30 (3H, t, J=7.0 Hz), 3.55-3.71 (2H, m), 5.08 (2H, s), 5.69 (1H, s), 6.91-7.07 (4H, m), 7.18-7.23 (1H, m), 7.30-7.61 (3H, m), 8.39-8.41 (1H, m), 9.02 (1H, br s), 10.01 (1H, br s).

ESI-MS Found: m/z 396 (M+H)$^+$

Example 69

5-Ethoxy-2-[ethoxy(4-trifluoromethoxyphenyl)methyl]-1H-benzimidazole

[Chemical formula 33]

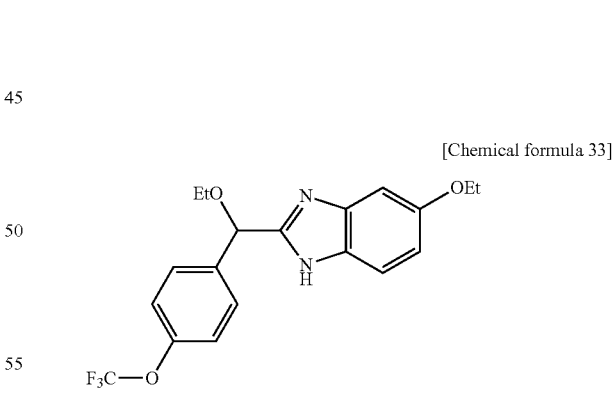

The title compound (63 mg) was obtained as a colorless amorphous material, in the same manner as described in Example 65 by using the compound of Reference Example 31 (300 mg) and 4-ethoxy-1,2-phenylenediamine (190 mg).

$^1$H-NMR (CDCl$_3$) δ: 1.31 (3H, t, J=7.0 Hz), 1.43 (3H, t, J=7.0 Hz), 3.58-3.68 (2H, m), 4.04 (2H, q, J=7.0 Hz), 5.68 (1H, s), 6.87-7.21 (4H, m), 7.28-7.61 (3H, m), 9.28-9.34 (1H, br m).

ESI-MS Found: m/z 381 (M+H)$^+$

Example 70

2-[Ethoxy(4-trifluoromethoxyphenyl)methyl]-5-fluoro-1H-benzimidazole

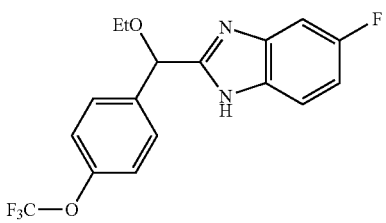

[Chemical formula 34]

The title compound (1.7 g) was obtained as a colorless solid, in the same manner as described in Example 65 by using the compound of Reference Example 31 (5.0 g) and 4-fluoro-1,2-phenylenediamine (2.6 g).

$^1$H-NMR (CDCl$_3$) δ: 1.31 (3H, t, J=7.0 Hz), 3.59-3.69 (2H, m), 5.68 (1H, s), 6.96-7.03 (1H, m), 7.08-7.13 (0.5H, m), 7.20 (2H, d, J=8.5 Hz), 7.32-7.40 (1H, m), 7.48 (2H, d, J=8.5 Hz), 7.60-7.67 (0.5H, m), 9.55 (1H, br s).

ESI-MS Found: m/z 355 (M+H)$^+$

Example 71

5-Ethoxy-2-[methoxy(4-trifluoromethoxyphenyl)methyl]-1H-benzimidazole

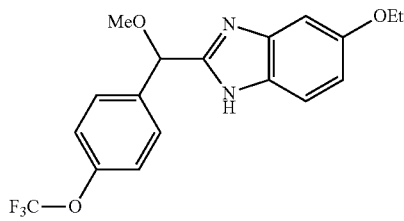 [SMILES: CCOc1ccc2[nH]c(C(OCC)c3ccc(SC(F)(F)F)cc3)nc2c1]

[Chemical formula 35]

The title compound (213 mg) was obtained as a pale yellow amorphous material, in the same manner as described in Example 65 by using the compound of Reference Example 32 (500 mg) and 4-ethoxy-1,2-phenylenediamine (335 mg).

$^1$H-NMR (CDCl$_3$) δ: 1.42 (3H, t, J=7.0 Hz), 3.47 (3H, s), 4.04 (2H, q, J=7.0 Hz), 5.56 (1H, s), 6.85-7.62 (7H, m), 9.36 (1H, br s).

ESI-MS Found: m/z 367 (M+H)$^+$

Examples 72 to 94

Compounds 72 to 94 that were produced in the same manner as described in Example 65 by using corresponding raw materials, are shown in Tables 16 to 20.

TABLE 16

| Example | Structural formula | $^1$H-NMR (CDCl$_3$) | MS |
|---|---|---|---|
| 72 | (structure) | δ: 1.29 (3H, t, J = 7.1 Hz), 1.46 (6H, t, J = 7.0 Hz), 3.56-3.66 (2H, m), 4.09 (4H, q, J = 7.0 Hz), 5.09 (2H, s), 5.61 (1H, s), 6.91-7.23 (7H, m), 7.35-7.38 (2H, m), 9.14 (1H, br s). | 483 (ESI+) |
| 73 | (structure) | δ: 1.29 (3H, t, J = 7.0 Hz), 2.45 (3H, s), 3.59-3.64 (2H, m), 5.07 (2H, s), 5.64 (1H, s), 6.91-7.23 (7H, m), 7.30-7.61 (3H, m), 9.29-9.32 (1H, br m). | 409 (ESI+) |

TABLE 16-continued

| Example | Structural formula | ¹H-NMR (CDCl₃) | MS |
|---|---|---|---|
| 74 | | δ: 1.29 (3H, t, J = 7.1 Hz), 3.55-3.66 (2H, m), 5.08 (2H, s), 5.61 (1H, s), 6.95-7.08 (4H, m), 7.18-7.26 (2H, m), 7.35 (2H, m), 7.47 (1H, m), 9.50 (1H, br s). | 431 (ESI+) |
| 75 | | δ: 1.29 (3H, t, J = 7.0 Hz), 1.46 (3H, t, J = 7.0 Hz), 3.55-3.66 (2H, m), 4.10 (2H, q, J = 7.0 Hz), 5.09 (2H, s), 5.61 (1H, s), 6.94-7.43 (9H, m), 9.29 (1H, br s). | 457 (ESI+) |
| 76 | | δ: 1.28-1.30 (3H, m), 1.49-1.52 (3H, m), 3.60-3.70 (2H, m), 4.19-4.21 (2H, m), 5.08 (2H, s), 5.67-5.74 (1H, m), 6.66-6.69 (1H, m), 6.93-7.39 (9H, m), 9.28-9.47 (1H, br m). | 439 (ESI+) |

TABLE 17

| Example | Structural formula | ¹H-NMR (CDCl₃) | MS |
|---|---|---|---|
| 77 | | δ: 1.32 (3H, t, J = 7.0 Hz), 3.55-3.72 (2H, m), 5.09 (2H, s), 5.67-5.68 (1H, m), 6.96-7.08 (4H, m), 7.17-7.23 (1H, m), 7.36-7.39 (2H, m), 7.50 (0.5H, d, J = 9.0 Hz), 7.75 (0.5H, d, J = 9.0 Hz), 8.15-8.22 (1H, m), 8.39 (0.5H, d, J = 2.0 Hz), 8.62 (0.5H, d, J = 2.0 Hz), 9.81-9.96 (H, br m). | 440 (ESI+) |

TABLE 17-continued

| Example | Structural formula | ¹H-NMR (CDCl₃) | MS |
|---|---|---|---|
| 78 | | δ: 1.29 (3H, t, J = 7.0 Hz), 1.42 (3H, t, J = 7.0 Hz), 3.57-3.67 (2H, m), 3.86 (3H, s), 4.04 (2H, q, J = 7.0 Hz), 5.15 (2H, s), 5.60 (1H, s), 6.84-7.61 (9H, m), 9.26 (1H, br s). | 469 (ESI+) |
| 79 | | δ: 1.26 (3H, t, J = 7.0 Hz), 1.42 (3H, t, J = 7.0 Hz), 3.61 (2H, q, J = 7.0 Hz), 3.81 (3H, s), 4.04 (2H, q, J = 7.0 Hz), 5.08 (2H, s), 5.97-5.98 (1H, m), 6.51-6.55 (2H, m), 6.83-7.60 (7H, m), 9.37-9.40 (1H, br m). | 469 (ESI+) |
| 80 | | δ: 1.30 (3H, t, J = 7.0 Hz), 1.43 (3H, t, J = 7.0 Hz), 3.56-3.67 (2H, m), 4.04 (2H, q, J = 7.0 Hz), 5.15 (2H, s), 5.59 (1H, s), 6.89-7.60 (9H, m), 9.29-9.34 (1H, br m). | 473 (ESI+) |
| 81 | | δ: 1.38-1.46 (3H, m), 3.45 (3H, s), 4.04 (2H, q, J = 7.0 Hz), 5.09 (2H, s), 5.51 (1H, s), 6.84-7.65 (10H, m), 9.21-9.27 (1H, br m). | 425 (ESI+) |

TABLE 18

| Example | Structural formula | ¹H-NMR (CDCl₃) | MS |
| --- | --- | --- | --- |
| 82 | | δ: 1.21-1.27 (6H, m), 1.38-1.46 (3H, m), 3.74-3.82 (1H, m), 4.04 (2H, q, J = 7.0 Hz), 5.08 (2H, s), 5.75 (1H, s), 6.84-7.60 (10H, m), 9.19-9.25 (1H, br m). | 453 (ESI+) |
| 83 | | δ: 0.92 (3H, d, J = 2.4 Hz), 0.94 (3H, d, J = 2.3 Hz), 1.40 (3H, t, J = 7.0 Hz), 1.90-1.99 (1H, m), 3.28 (1H, dd, J = 9.0, 6.4 Hz), 3.31 (1H, dd, J = 9.0, 6.4 Hz), 3.97-4.01 (2H, m), 5.03 (2H, s), 5.58 (1H, s), 6.83-7.58 (10H, m), 9.72-9.75 (1H, br m). | 467 (ESI+) |
| 84 | | δ: 1.41 (3H, t, J = 7.0 Hz), 3.43 (3H, s), 3.55-3.83 (4H, m), 4.03 (2H, q, J = 7.0 Hz), 5.06 (2H, s), 5.68 (1H, s), 6.84-7.57 (10H, m), 10.24-10.32 (1H, br m). | 469 (ESI+) |

TABLE 18-continued

| Example | Structural formula | ¹H-NMR (CDCl₃) | MS |
|---|---|---|---|
| 85 | (structure) | δ: 1.29 (3H, t, J = 7.0 Hz), 1.43 (3H, t, J = 7.0 Hz), 3.57-3.67 (2H, m), 4.04 (2H, q, J = 7.0 Hz), 5.36 (2H, s), 5.63 (1H, s), 6.76-7.63 (10H, m), 8.23-8.28 (1H, m), 9.38-9.44 (1H, br m). | 404 (ESI+) |

TABLE 19

| Example | Structural formula | ¹H-NMR (CDCl₃) | MS |
|---|---|---|---|
| 86 | (structure) | δ: 1.29 (3H, t, J = 7.0 Hz), 3.55-3.69 (2H, m), 3.82 (3H, s), 5.67 (1H, s), 6.86-7.22 (4H, m), 7.44-7.58 (3H, m), 9.55 (1H, br s). | 367 (ESI+) |
| 87 | (structure) | δ: 3.47 (3H, d, J = 1.2 Hz), 3.82 (3H, d, J = 1.2 Hz), 5.56 (1H, s), 6.86-7.49 (7H, m), 9.50 (1H, br s). | 351 (ESI+) |
| 88 | (structure) | δ: 3.48 (3H, s), 5.57 (1H, s), 7.20-7.70 (7H, m), 9.49 (1H, br s). | 357 (ESI+) |
| 89 | (structure) | δ: 3.48 (3H, s), 5.57 (1H, s), 6.96-7.05 (1H, m), 7.08-7.14 (0.5H, m), 7.22 (2H, d, J = 8.6 Hz), 7.31-7.43 (1H, m), 7.48 (2H, d, J = 8.6 Hz), 7.61-7.68 (0.5H, m), 9.45 (1H, s). | 339 (ESI+) |

TABLE 19-continued

| Example | Structural formula | ¹H-NMR (CDCl₃) | MS |
|---|---|---|---|
| 90 | (MeO, F₃C—O-phenyl, benzimidazole, SO₂NMe₂ structure) | δ: 2.68 (6H, s), 3.48 (3H, s), 4.82 (1H, s), 6.83 (1H, d, J = 8.4 Hz), 7.27 (2H, d, J = 8.6 Hz), 7.47 (1H, dd, J = 8.4, 2.0 Hz), 7.52 (2H, d, J = 8.6 Hz), 7.60 (1H, d, J = 2.0 Hz), 8.48 (1H, br s). | 430 (ESI+) |

TABLE 20

| Example | Structural formula | ¹H-NMR (CDCl₃) | MS |
|---|---|---|---|
| 91 | (EtO, F₃C—S-phenyl, benzimidazole, OEt structure) | δ: 1.31 (3H, t, J = 7.0 Hz), 1.42 (3H, t, J = 7.0 Hz), 3.60-3.71 (2H, m), 4.04 (2H, q, J = 7.0 Hz), 5.70 (1H, s), 6.86-7.66 (7H, m), 9.23-9.30 (1H, br m). | 395 (ESI+) |
| 92 | (EtO, PhNHSO₂-phenyl, benzimidazole, OEt structure) | δ: 1.29 (3H, t, J = 7.0 Hz), 1.42 (3H, t, J = 7.0 Hz), 3.61 (2H, q, J = 7.0 Hz), 4.04 (2H, q, J = 7.0 Hz), 5.69 (1H, s), 6.80-7.76 (12H, m), 9.32 (1H, br s). | 452 (ESI+) |
| 93 | (EtO, F₃C—SO₂-phenyl, benzimidazole, F structure) | δ: 1.36 (3H, t, J = 7.0 Hz), 3.70 (2H, q, J = 7.0 Hz), 5.82 (1H, d, J = 2.0 Hz), 6.98-7.07 (1H, m), 7.13 (0.5H, dd, J = 8.4, 2.4 Hz), 7.34-7.43 (1H, m), 7.66 (0.5H, dd, J = 8.9, 4.4 Hz), 7.82 (2H, d, J = 8.4 Hz), 8.04 (2H, d, J = 8.4 Hz), 9.40 (1H, br s). | 403 (ESI+) |
| 94 | (HO, F₃C—O-phenyl, benzimidazole, acetyl structure) | δ: 2.60 (3H, s), 6.14 (1H, s), 7.11 (2H, d, J = 8.2 Hz), 7.43-7.47 (3H, m), 7.83 (1H, d, J = 8.6 Hz), 8.13 (1H, s). | 351 (ESI+) |

Example 95

2-[(4-Benzyloxyphenyl)ethoxymethyl]-5-ethoxy-1H-benzimidazole

[Chemical formula 36]

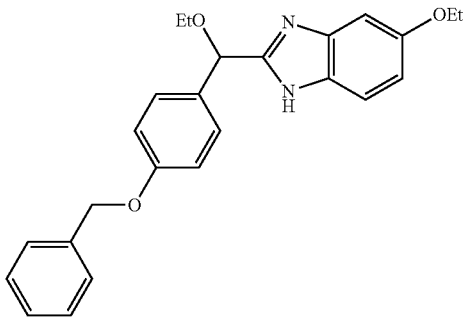 [SMILES: CCOc1ccc2[nH]c(C(OCC)c3ccc(OCc4ccccn4)cc3)nc2c1]

The compound of Reference Example 37 (100 mg) was dissolved in DMF (2 mL), and benzyl bromide (58 mg) and potassium carbonate (47 mg) were added thereto under ice cooling. The mixture was stirred for 21 hours at the same temperature. Water was added to the reaction mixture, and the mixture was extracted with ethyl acetate. The organic layer was washed with saturated brine and then dried over anhydrous sodium sulfate. After distilling off the solvent under reduced pressure, the residue thus obtained was purified by silica gel column chromatography (20% to 100% ethyl acetate/hexane), and thus the title compound (30 mg) was obtained as a colorless solid.

$^1$H-NMR (CDCl$_3$) δ: 1.28 (3H, t, J=7.0 Hz), 1.42 (3H, t, J=7.0 Hz), 3.59-3.63 (2H, m), 4.04 (2H, q, J=7.0 Hz), 5.04 (2H, s), 5.62 (1H, s), 6.85-7.22 (4H, m), 7.31-7.61 (8H, m), 9.21 (1H, br s).

ESI-MS Found: m/z 403 (M+H)$^+$

Examples 96 to 100

Compounds 96 to 100 that were produced in the same manner as described in Example 95 by using corresponding raw materials, are shown in Table 21.

TABLE 21

| Example | Structural formula | $^1$H-NMR (CDCl$_3$) | MS |
|---|---|---|---|
| 96 | (EtO-benzimidazole-OEt with 4-fluorobenzyloxyphenyl) | δ: 1.29 (3H, t, J = 7.0 Hz), 1.43 (3H, t, J = 7.0 Hz), 3.56-3.67 (2H, m), 4.04 (2H, q, J = 7.0 Hz), 5.00 (2H, s), 5.62 (1H, s), 6.93-7.55 (11H, m), 9.20-9.25 (1H, br m). | 421 (ESI+) |
| 97 | (EtO-benzimidazole-OEt with 4-methoxybenzyloxyphenyl) | δ: 1.28 (3H, t, J = 7.1 Hz), 1.42 (3H, t, J = 7.1 Hz), 3.58-3.63 (2H, m), 3.81 (3H, s), 4.04 (2H, q, J = 7.1 Hz), 4.96 (2H, s), 5.62 (1H, s), 6.85-7.20 (6H, m), 7.39-7.53 (5H, m), 9.21-9.26 (1H, br m). | 433 (ESI+) |
| 98 | (EtO-benzimidazole-OEt with 4-methoxycarbonylbenzyloxyphenyl) | δ: 1.28 (3H, t, J = 7.0 Hz), 1.42 (3H, t, J = 7.0 Hz), 3.55-3.63 (2H, m), 3.92 (3H, s), 4.03 (2H, q, J = 7.0 Hz), 5.09 (2H, s), 5.62 (1H, s), 6.84-7.19 (4H, m), 7.29-7.59 (5H, m), 8.04 (2H, d, J = 8.1 Hz), 9.29-9.34 (1H, br m). | 461 (ESI+) |

TABLE 21-continued

| Example | Structural formula | ¹H-NMR (CDCl₃) | MS |
|---|---|---|---|
| 99 | (structure) | δ: 1.29 (3H, t, J = 7.0 Hz), 1.42 (3H, t, J = 7.0 Hz), 3.53-3.69 (2H, m), 4.04 (2H, q, J = 7.0 Hz), 5.10 (2H, s), 5.62 (1H, s), 6.85-7.38 (7H, m), 7.52 (2H, d, J = 8.2 Hz), 7.63 (2H, d, J = 8.2 Hz), 9.20-9.23 (1H, br m). | 471 (ESI+) |
| 100 | (structure) | δ: 1.28 (3H, t, J = 7.0 Hz), 1.42 (3H, t, J = 7.0 Hz), 3.54-3.65 (2H, m), 4.04 (2H, q, J = 7.0 Hz), 5.16 (2H, s), 5.61 (1H, s), 6.99-7.61 (9H, m), 7.71 (1H, m), 8.59 (1H, d, J = 4.2 Hz), 9.28 (1H, br s). | 404 (ESI+) |

Example 101

5-Ethoxy-2-{ethoxy[4-(3-fluorobenzyloxy)phenyl]methyl}-1H-benzimidazole

[Chemical formula 37]

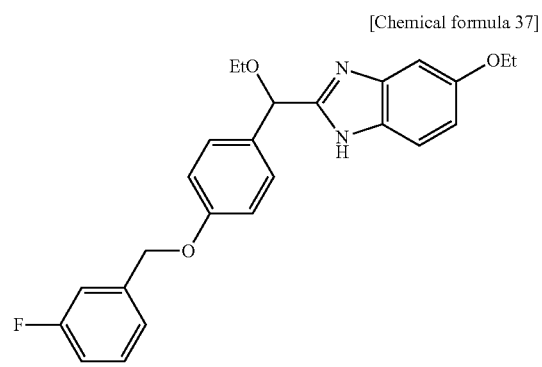 [SMILES: CCOc1ccc2[nH]c(C(OCC)c3ccc(OCc4cccc(F)c4)cc3)nc2c1]

The compound of Reference Example 41 (150 mg) was dissolved in DMF (2 mL), and potassium carbonate (63 mg) and 3-fluorobenzyl bromide (78 mg) were added thereto under ice cooling. The mixture was stirred for 21 hours at room temperature. After distilling off the solvent under reduced pressure, the residue was diluted with water and extracted with ethyl acetate. The organic layer was washed with saturated brine and then dried over anhydrous sodium sulfate. After distilling off the solvent under reduced pressure, the residue thus obtained was purified by silica gel column chromatography (10% to 100% ethyl acetate/hexane), and thus 5-ethoxy-2-{ethoxy[4-(3-fluorobenzyloxy)phenyl]methyl}benzimidazole-1-carboxylic acid tert-butyl ester (172 mg) was obtained.

5-Ethoxy-2-{ethoxy[4-(3-fluorobenzyloxy)phenyl]methyl}benzimidazole-1-carboxylic acid tert-butyl ester (172 mg) thus obtained was dissolved in dichloromethane (2 mL), and TFA (2 mL) was added thereto under ice cooling. The mixture was stirred for 1.5 hours at room temperature. After distilling off the solvent under reduced pressure, the residue was diluted with a saturated aqueous solution of sodium hydrogen carbonate and extracted with ethyl acetate. The organic layer was washed with saturated brine and then dried over anhydrous sodium sulfate. After distilling off the solvent under reduced pressure, the residue was purified by silica gel column chromatography (10% to 100% ethyl acetate/hexane), and thus the title compound (82 mg) was obtained as a colorless solid.

¹H-NMR (CDCl₃) δ: 1.29 (3H, t, J=7.0 Hz), 1.42 (3H, t, J=7.0 Hz), 3.55-3.66 (2H, m), 4.04 (2H, q, J=7.0 Hz), 5.03 (2H, s), 5.62 (1H, s), 6.85-7.60 (11H, m), 9.26-9.32 (1H, br m).

ESI-MS Found: m/z 421 (M+H)⁺

Compounds 102 to 108 that were produced in the same manner as described in Example 101 by using corresponding raw materials, are shown in Tables 22 and 23.

TABLE 22
| Example | Structural formula | $^1$H-NMR (CDCl$_3$) | MS |
|---|---|---|---|
| 102 | 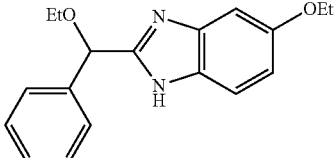 | δ: 1.29 (3H, t, J = 7.0 Hz), 1.42 (3H, t, J = 7.0 Hz), 3.55-3.66 (2H, m), 4.04 (2H, q, J = 7.0 Hz), 5.11 (2H, s), 5.62 (1H, s), 6.85-7.61 (11H, m), 9.25 (1H, br s). | 421 (ESI+) |
| 103 | 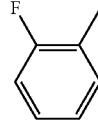 | δ: 1.28 (3H, t, J = 7.1 Hz), 1.42 (3H, t, J = 7.0 Hz), 3.52-3.68 (2H, m), 4.03 (2H, q, J = 7.0 Hz), 4.99 (2H, s), 5.61 (1H, s), 6.85-7.59 (11H, m), 9.34-9.38 (1H, br m). | 437 (ESI+) |
| 104 | 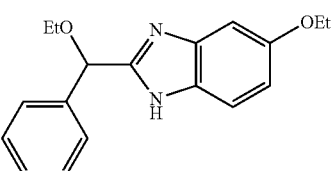 | δ: 1.28 (3H, t, J = 7.0 Hz), 1.42 (3H, t, J = 7.0 Hz), 3.55-3.66 (2H, m), 3.79 (6H, s), 4.04 (2H, q, J = 7.0 Hz), 4.97 (2H, s), 5.62 (1H, s), 6.40 (1H, t, J = 2.2 Hz), 6.56 (2H, d, J = 2.2 Hz), 6.85-7.60 (7H, m), 9.26 (1H, br s). | 463 (ESI+) |
| 105 | 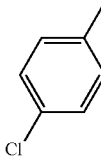 | δ: 1.28 (3H, t, J = 7.0 Hz), 1.42 (3H, t, J = 7.0 Hz), 3.53-3.68 (2H, m), 4.03 (2H, q, J = 7.0 Hz), 5.02 (2H, s), 5.62 (1H, s), 6.85-6.95 (4H, m), 7.22 (2H, d, J = 8.8 Hz), 7.33-7.59 (5H, m), 9.35 (1H, br s). | 487 (ESI+) |

TABLE 23

| Example | Structural formula | $^1$H-NMR (CDCl$_3$) | MS |
|---|---|---|---|
| 106 | | δ: 1.29 (3H, t, J = 7.0 Hz), 1.42 (3H, t, J = 7.0 Hz), 3.57-3.67 (2H, m), 4.04 (2H, q, J = 7.0 Hz), 5.06 (2H, s), 5.63 (1H, s), 6.86-7.61 (8H, m), 7.75 (1H, d, J = 7.9 Hz), 8.58 (1H, m), 8.66 (1H, br s), 9.26 (1H, br s). | 404 (ESI+) |
| 107 | | δ: 1.28 (3H, t, J = 7.1 Hz), 1.42 (3H, t, J = 7.0 Hz), 2.35 (3H, s), 3.55-3.66 (2H, m), 4.04 (2H, q, J = 7.0 Hz), 4.99 (2H, s), 5.61 (1H, s), 6.85-7.57 (11H, m), 9.24 (1H, br s). | 417 (ESI+) |
| 108 | | δ: 1.28 (3H, t, J = 7.0 Hz), 1.42 (3H, t, J = 7.0 Hz), 3.53-3.69 (2H, m), 4.04 (2H, q, J = 7.0 Hz), 5.04 (2H, s), 5.62 (1H, s), 6.80-7.59 (10H, m), 9.26-9.31 (1H, br m). | 439 (ESI+) |

Example 109

5-Ethoxy-2-[ethoxy(4-phenyloxyphenyl)methyl]-1H-benzimidazole

[Chemical formula 38]

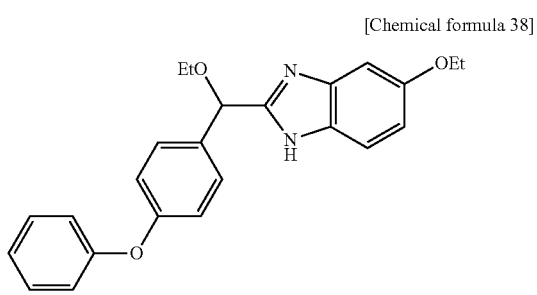 [SMILES: CCOc1ccc2[nH]c(C(OCC)c3ccc(Oc4ccccc4)cc3)nc2c1]

The compound of Reference Example 41 (200 mg) was dissolved in dichloromethane (5 mL), and phenylboronic acid (125 mg), copper(II) acetate (88 mg), and pyridine (192 mg) were sequentially added thereto under ice cooling. The mixture was stirred for 54 hours at room temperature. The reaction mixture was subjected to Celite filtration, and the filtrate was distilled off under reduced pressure. The residue thus obtained was purified by silica gel column chromatography (10% to 100% ethyl acetate/hexane), and thus 5-ethoxy-2-[ethoxy(4-phenyloxyphenyl)methyl]benzimidazole-1-carboxylic acid tert-butyl ester (237 mg) was obtained.

5-Ethoxy-2-[ethoxy(4-phenyloxyphenyl)methyl]benzimidazole-1-carboxylic acid tert-butyl ester (237 mg) thus obtained was dissolved in dichloromethane (2 mL), and TFA (2 mL) was added thereto under ice cooling. The mixture was stirred for 1.5 hours at room temperature. After distilling off the solvent under reduced pressure, the residue was diluted with a saturated aqueous solution of sodium hydrogen carbonate and extracted with ethyl acetate. The organic layer was washed with saturated brine and then dried over anhydrous sodium sulfate. After distilling off the solvent under reduced pressure, the residue was purified by silica gel column chromatography (10% to 100% ethyl acetate/hexane), and thus the title compound (38 mg) was obtained as a colorless solid.

$^1$H-NMR (CDCl$_3$) δ: 1.30 (3H, t, J=7.0 Hz), 1.43 (3H, t, J=7.0 Hz), 3.55-3.69 (2H, m), 4.05 (2H, q, J=7.0 Hz), 5.65 (1H, s), 6.86-7.61 (12H, m), 9.25-9.31 (1H, br m).

ESI-MS Found: m/z 389 (M+H)$^+$

Example 110

5-Ethoxy-2-[ethoxy(4-phenethyloxyphenyl)methyl]-1H-benzimidazole

[Chemical formula 39]

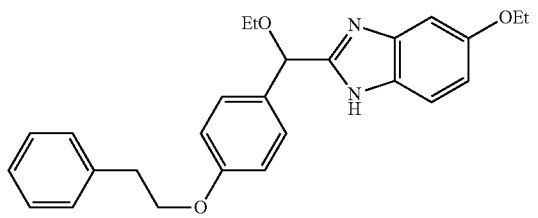

The compound of Reference Example 41 (250 mg) was dissolved in DMF (4 mL), and 2-phenethyl alcohol (78 mg), triphenylphosphine (167 mg), and 2.2 mol/L of diisopropyl azodicarboxylate (toluene solution) (133 mg) were sequentially added thereto under ice cooling. The mixture was stirred for 19 hours at room temperature, and was heated for 2.5 hours at 50° C. After distilling off the solvent was distilled off under reduced pressure, the residue was purified by silica gel column chromatography (10% to 100% ethyl acetate/hexane). Thus, 5-ethoxy-2-[ethoxy(4-phenethyloxyphenyl)methyl]benzimidazole-1-carboxylic acid tert-butyl ester (199 mg) was obtained.

The title compound (24 mg) was obtained as a colorless solid, in the same manner as described in Example 109 from 5-ethoxy-2-[ethoxy(4-phenethyloxyphenyl)methyl]benzimidazole-1-carboxylic acid tert-butyl ester (199 mg) thus obtained.

$^1$H-NMR (CDCl$_3$) δ: 1.28 (3H, t, J=7.0 Hz), 1.42 (3H, t, J=7.0 Hz), 3.08 (2H, t, J=7.1 Hz), 3.54-3.65 (2H, m), 4.04 (2H, q, J=7.0 Hz), 4.15 (2H, t, J=7.1 Hz), 5.61 (1H, s), 6.86-7.61 (12H, m), 9.20 (1H, br s).

ESI-MS Found: m/z 417 (M+H)$^+$

Example 111

1-{4-[Ethoxy(5-ethoxy-1H-benzimidazol-2-yl)methyl]phenyl}-2-phenylethanone

[Chemical formula 40]

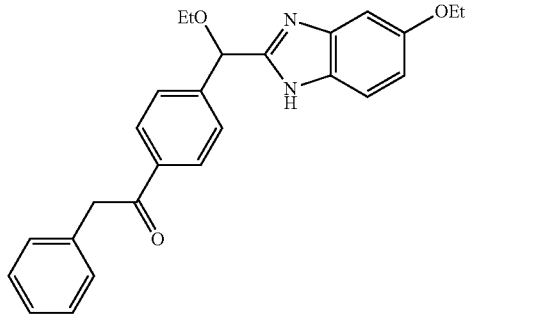

The compound of Reference Example 43 (100 mg) was dissolved in THF (2 mL), and 2 mol/L of benzylmagnesium chloride (THF solution) (1 mL) was added thereto under ice cooling. The mixture was stirred for one hour at room temperature. The reaction mixture was diluted with a saturated aqueous solution of ammonium chloride and extracted with ethyl acetate. The organic layer was dried over anhydrous sodium sulfate. After distilling off the solvent under reduced pressure, the residue was purified by silica gel column chromatography (10% to 100% ethyl acetate/hexane), and thus the title compound (110 mg) was obtained as a colorless amorphous material.

$^1$H-NMR (CDCl$_3$) δ: 1.30 (3H, t, J=7.0 Hz), 1.42 (3H, t, J=7.0 Hz), 3.64 (2H, m), 4.03 (2H, q, J=7.0 Hz), 4.24 (2H, s), 5.71 (1H, s), 6.80-7.40 (7H, m), 7.54-7.66 (3H, m), 7.99 (2H, d, J=8.4 Hz), 9.26-9.32 (1H, br m).

ESI-MS Found: m/z 415 (M+H)$^+$

Example 112

(5-Bromo-1H-benzimidazol-2-yl)-(4-trifluoromethoxyphenyl)methanol

[Chemical formula 41]

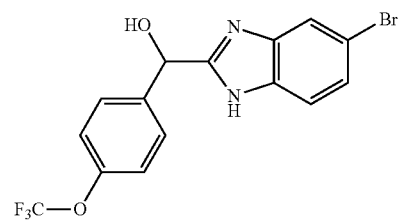

The compound of Reference Example 45 (1.1 g) and 4-bromo-1,2-diaminobenzene (770 mg) were dissolved in xylene (8 mL), and the mixture was heated to reflux for 30 minutes while being stirred. About 2.0 mol/L of trimethylaluminum (toluene solution) (2.1 mL) was added to the reaction mixture, and the mixture was heated for 15 hours at 120° C. A 10% aqueous solution of sodium hydroxide and methanol were added to the reaction mixture, and the mixture was extracted with chloroform. The organic layer was washed with saturated brine and then dried over anhydrous sodium sulfate. After distilling off the solvent under reduced pressure, the residue was purified by silica gel column chromatography (33% to 75% ethyl acetate/hexane), and thus the title compound (498 mg) was obtained as a pale yellow amorphous material.

$^1$H-NMR (CDCl$_3$) δ: 6.01 (1H, s), 7.13 (2H, d, J=8.4 Hz), 7.27-7.32 (2H, m), 7.39 (2H, d, J=8.4 Hz), 7.57 (1H, s)

ESI-MS Found: m/z 387 (M+H)$^+$

Example 113

5-bromo-2-[ethoxy(4-trifluoromethoxyphenyl)methyl]-1H-benzimidazole

[Chemical formula 42]

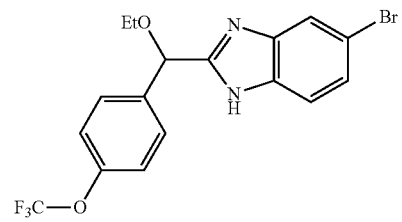

The title compound (176 mg) was obtained as a colorless solid, in the same manner as described in Example 21 by using the compound of Example 112 (246 mg) and ethanol (3 mL).

$^1$H-NMR (CDCl$_3$) δ: 1.31 (3H, t, J=7.1 Hz), 3.58-3.69 (2H, m), 5.69 (1H, s), 7.20 (2H, d, J=8.4 Hz), 7.24-7.36 (2H, m), 7.47 (2H, d, J=8.4 Hz), 7.57-7.86 (1H, m), 9.53 (1H, br s).

ESI-MS Found: m/z 415 (M+H)$^+$

Example 114

2-[Hydroxy(4-trifluoromethoxyphenyl)methyl]-1H-benzimidazole-5-carbonitrile

[Chemical formula 43]

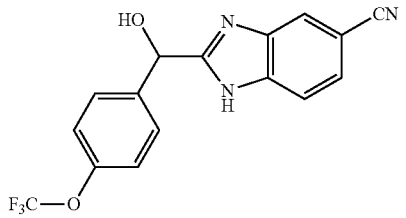

The compound of Example 112 (300 mg) and zinc cyanide (364 mg) were suspended in DMF (4 mL), and argon bubbling was carried out for 10 minutes. Tetrakistriphenylphosphine palladium (179 mg) was added to the reaction mixture, and the mixture was heated for one hour at 130° C. by means of a microwave reaction apparatus. A 28% aqueous ammonia solution (6 mL) was added to the reaction mixture, the mixture was filtered through a glass filter, and then the filtrate was extracted with diethyl ether. The organic layer was washed with saturated brine and then dried over anhydrous sodium sulfate. After distilling off the solvent under reduced pressure, the residue was purified by silica gel column chromatography (33% to 75% ethyl acetate/hexane), and subsequently the residue was suspended in ethyl acetate and hexane and then was collected by filtration. Thus, the title compound (16 mg) was obtained as a colorless solid.

$^1$H-NMR (DMSO-d$_6$) δ: 6.02 (1H, d, J=4.0 Hz), 6.79 (1H, d, J=4.0 Hz), 7.35 (2H, d, J=8.2 Hz), 7.51-7.72 (4H, m), 7.89-8.07 (1H, m), 13.01 (1H, br s).

ESI-MS Found: m/z 334 (M+H)$^+$

Example 115

2-[Ethoxy(4-trifluoromethoxyphenyl)methyl]-1H-benzimidazole-5-carbonitrile

[Chemical formula 44]

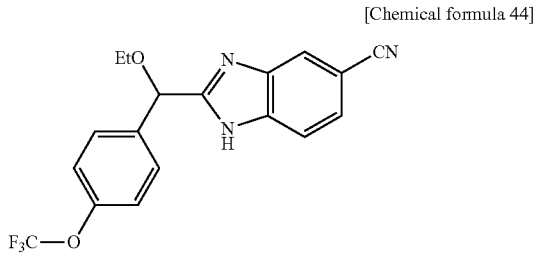 [SMILES: N#Cc1ccc2[nH]c(C(O)c3ccc(OC(F)(F)F)cc3)nc2c1]

The title compound (103 mg) was obtained as a colorless solid, in the same manner as described in Example 114 by using the compound of Example 113 (139 mg).

$^1$H-NMR (CDCl$_3$) δ: 1.33 (3H, t, J=7.1 Hz), 3.60-3.71 (2H, m), 5.72 (1H, s), 7.21-7.25 (2H, m), 7.46-8.04 (5H, m), 9.77-9.81 (1H, br m).

ESI-MS Found: m/z 362 (M+H)$^+$

Example 116

Benzyl 4-[ethoxy(5-ethoxy-1H-benzimidazol-2-yl)methyl]benzoate

[Chemical formula 45]

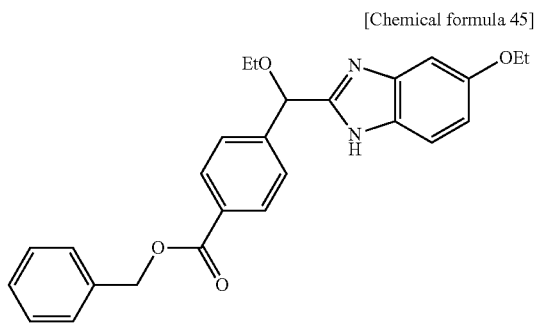 [SMILES: CCOc1ccc2[nH]c(C(OCC)c3ccc(C(=O)OCc4ccccc4)cc3)nc2c1]

The compound of Reference Example 44 (100 mg) was dissolved in THF (4 mL), and EDC (56 mg), DIPEA (190 mg), DMAP (4 mg), and benzyl alcohol (159 mg) were sequentially added thereto. The mixture was stirred for 16 hours at room temperature. Water was added to the reaction mixture, and the mixture was extracted with ethyl acetate. The organic layer was washed with saturated brine and then dried over anhydrous sodium sulfate. After distilling off the solvent under reduced pressure, the residue was purified by basic silica gel column chromatography (12% to 50% ethyl acetate/hexane), and thus the title compound (24 mg) was obtained as a colorless amorphous material.

$^1$H-NMR (CDCl$_3$) δ: 1.29 (3H, t, J=7.0 Hz), 1.41 (3H, t, J=7.0 Hz), 3.63 (2H, q, J=7.0 Hz), 4.02 (2H, q, J=7.0 Hz), 5.34 (2H, s), 5.71 (1H, s), 6.80-7.25 (2H, m), 7.26-7.59 (8H, m), 8.04 (2H, d, J=8.2 Hz), 9.41 (1H, br s).

ESI-MS Found: m/z 431 (M+H)$^+$

Example 117

N-benzyl-4-[ethoxy(5-ethoxy-1H-benzimidazol-2-yl)methyl]benzamide

[Chemical formula 46]

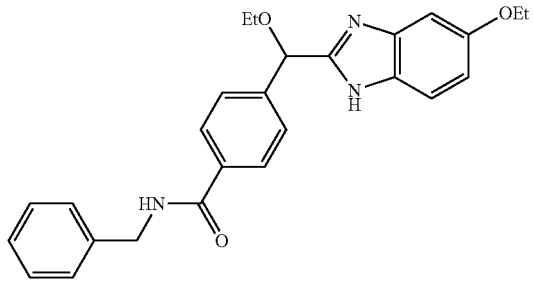

The compound of Reference Example 44 (40 mg) was dissolved in THF (4 mL), and HATU (67 mg), DIPEA (76 mg), and benzylamine (159 mg) were sequentially added thereto. The mixture was stirred for 12 hours at room temperature. Water was added to the reaction mixture, and the mixture was extracted with ethyl acetate. The organic layer was washed with saturated brine and then dried over anhydrous sodium sulfate. After distilling off the solvent under reduced pressure, the residue was purified by basic silica gel column chromatography (12% to 50% ethyl acetate/hexane), and thus the title compound (40 mg) was obtained as a colorless solid.

$^1$H-NMR (CDCl$_3$) δ: 1.25 (3H, t, J=7.0 Hz), 1.39 (3H, t, J=7.0 Hz), 3.57 (2H, q, J=7.0 Hz), 3.98 (2H, q, J=7.0 Hz), 4.59 (2H, d, J=5.9 Hz), 5.61 (1H, s), 6.82-6.86 (2H, m), 6.96 (1H, br s), 7.22-7.48 (8H, m), 7.66 (2H, d, J=8.4 Hz), 10.13 (1H, br s).

ESI-MS Found: m/z 430 (M+H)$^+$

Example 118

(5-Fluoro-1H-benzimidazol-2-yl)-[1-(4-fluorobenzyl)-1H-indol-5-yl]methanol

[Chemical formula 47]

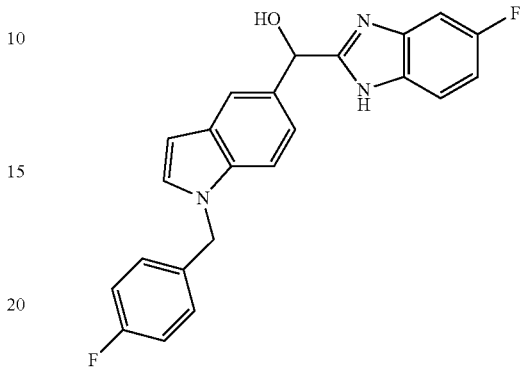

The title compound (660 mg) was obtained as a yellow amorphous material, in the same manner as described in Example 1 by using the compound of Reference Example 1 (400 mg) and the compound of Reference Example 47 (530 mg).

$^1$H-NMR (CDCl$_3$) δ: 5.26 (2H, s), 6.10 (1H, s), 6.53 (1H, d, J=3.2 Hz), 6.92-6.99 (3H, m), 7.03-7.08 (2H, m), 7.14 (1H, d, J=3.2 Hz), 7.18-7.25 (3H, m), 7.43 (1H, s), 7.71 (1H, s).

ESI-MS Found: m/z 390 (M+H)$^+$

Examples 119 to 133

Compounds 119 to 133 that were produced in the same manner as described in Example 65 by using corresponding raw materials, are shown in Tables 24 and 25.

TABLE 24

| Example | Structural formula | $^1$H-NMR (CDCl$_3$) | MS |
|---|---|---|---|
| 119 | ![structure] | δ: 1.29-1.35 (3H, m), 3.59-3.70 (2H, m), 5.69-5.71 (1H, m), 6.96-7.03 (1H, m), 7.19-7.25 (3H, m), 7.47-7.50 (2H, m), 9.50-9.65 (1H, m). | 389 (ESI+) |
| 120 | ![structure] | δ: 1.29 (3H, t, J = 7.0 Hz), 3.55-3.69 (2H, m), 4.36 (2H, br s), 5.65 (1H, s), 6.49 (1H, d, J = 1.6 Hz), 6.79 (1H, s), 7.19 (2H, d, J = 8.4 Hz), 7.45 (2H, d, J = 8.4 Hz), 9.29 (1H, br s). | 386 (ESI+) |

TABLE 24-continued
| Example | Structural formula | ¹H-NMR (CDCl₃) | MS |
|---|---|---|---|
| 121 | 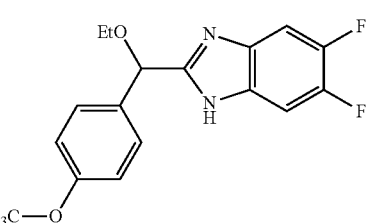 | δ: 1.31 (3H, t, J = 7.1 Hz), 3.55-3.70 (2H, m), 5.66 (1H, s), 7.18-7.25 (3H, m), 7.43-7.51 (3H, m), 9.57 (1H, br s). | 373 (ESI+) |
| 122 | 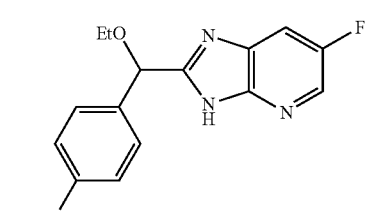 | δ: 1.35 (3H, t, J = 7.1 Hz), 3.63-3.84 (2H, m), 5.78 (1H, s), 7.20 (2H, d, J = 8.6 Hz), 7.57 (2H, d, J = 8.6 Hz), 7.80 (1H, dd, J = 8.6, 2.2 Hz), 8.34-8.38 (1H, m), 13.42 (1H, br s). | 356 (ESI+) |
| 123 | 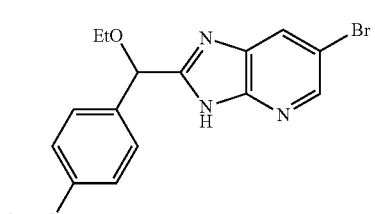 | δ: 1.34 (3H, , J = 7.0 Hz), 3.64-3.75 (2H, m), 5.72 (1H, s), 7.22 (2H, d, J = 8.4 Hz), 7.53 (2H, d, J = 8.4 Hz), 8.15-8.17 (1H, m), 8.45-8.47 (1H, m), 11.64 (1H, br s). | 416 (ESI+) |
| 124 | 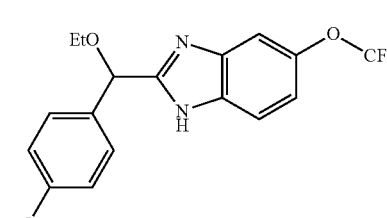 | δ: 1.32 (3H, t, J = 7.0 Hz), 3.56-3.73 (2H, m), 5.70 (1H, s), 7.11-7.16 (1H, m), 7.21 (2H, d, J = 8.2 Hz), 7.31-7.44 (1H, m), 7.49 (2H, d, J = 8.2 Hz), 7.58-7.72 (1H, m), 9.56 (1H, br s). | 421 (ESI+) |
| 125 | 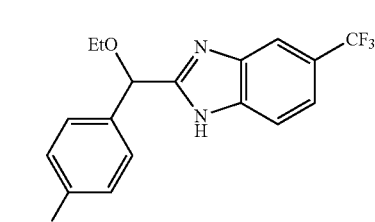 | δ: 1.25 (3H, t, J = 7.0 Hz), 3.53-3.69 (2H, m), 5.70 (1H, s), 7.11 (2H, d, J = 8.2 Hz), 7.42 (2H, d, J = 8.2 Hz), 7.46-8.12 (3H, m), 10.60-11.20 (1H, br m). | 405 (ESI+) |
| 126 | 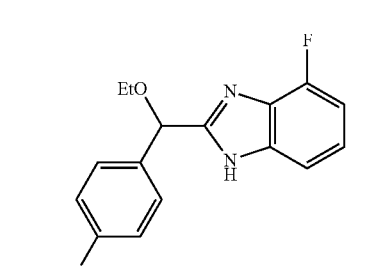 | δ: 1.29-1.36 (3H, m), 3.58-3.71 (2H, m), 5.72-5.75 (1H, m), 6.91-7.02 (1H, m), 7.11-7.24 (4H, m), 7.51 (2H, d, J = 8.6 Hz), 9.40-9.64 (1H, m). | 355 (ESI+) |

TABLE 25

| Example | Structural formula | ¹H-NMR (CDCl₃) | MS |
| --- | --- | --- | --- |
| 127 | (EtO, 4-F₃CO-phenyl, benzimidazole-OCHF₂) | δ: 1.31 (3H, t, J = 7.1 Hz), 3.56-3.72 (2H, m), 5.70 (1H, s), 6.49 (1H, t, J = 74.2 Hz), 7.02-7.10 (1H, m), 7.16-7.70 (6H, m), 9.59 (1H, br s). | 403 (ESI+) |
| 128 | (MeO, 3-Br-4-F₃CO-phenyl, benzimidazole-F) | δ: 3.49 (3H, s), 5.54 (1H, s), 6.97-7.12 (1.5H, m), 7.25-7.42 (3H, m), 7.61-7.66 (0.5H, m), 7.74 (1H, d, J = 2.0 Hz), 9.64 (1H, br s). | 419 (ESI+) |
| 129 | (MeO, 3-Br-4-F₃CO-phenyl, benzimidazole) | δ: 3.50 (3H, s), 5.58 (1H, s), 7.25-7.29 (3H, m), 7.40-7.44 (2H, m), 7.72-7.76 (2H, m), 9.59 (1H, br s). | 401 (ESI+) |
| 130 | (MeO, 3-Br-4-F₃CO-phenyl, benzimidazole-OMe) | δ: 3.49 (3H, s), 3.84 (3H, s), 5.54 (1H, s), 6.89-6.91 (1.5H, m), 7.22-7.33 (2H, m), 7.39-7.43 (1H, m), 7.60-7.63 (0.5H, m), 7.75 (1H, d, J = 2.0 Hz), 9.29 (1H, br s). | 431 (ESI+) |
| 131 | (MeO, 3-Br-4-F₃CO-phenyl, benzimidazole-OEt) | δ: 1.42 (3H, t, J = 7.0 Hz), 3.48 (3H, s), 4.04 (2H, q, J = 7.0 Hz), 5.53 (1H, s), 6.88-6.90 (1.5H, m), 7.19-7.27 (2H, m), 7.39 (1H, dd, J = 8.5, 2.0 Hz), 7.58 (0.5H, s), 7.74 (1H, d, J = 2.0 Hz), 9.49-9.61 (1H, m). | 445 (ESI+) |
| 132 | (EtO, 4-F₃C-phenyl, benzimidazole-OCHF₂) | δ: 1.33 (3H, t, J = 7.0 Hz), 3.58-3.73 (2H, m), 5.72-5.76 (1H, m), 6.23-6.75 (1H, m), 7.02-7.10 (1H, m), 7.21-7.69 (6H, m), 9.56 (1H, br s). | 387 (ESI+) |
| 133 | (MeO, 4-F₃C-phenyl, benzimidazole-OCHF₂) | δ: 3.48 (3H, s), 5.61 (1H, s), 6.48 (1H, t, J = 74.2 Hz), 7.05 (1H, t, J = 6.8 Hz), 7.16-7.68 (6H, m), 9.93-10.05 (1H, br m). | 373 (ESI+) |

Examples 134 to 140

Compounds 134 to 140 that were produced in the same manner as described in Example 1 by using corresponding raw materials, are shown in Table 26.

TABLE 26

| Example | Structural formula | $^1$H-NMR (CDCl$_3$) | MS |
| --- | --- | --- | --- |
| 134 | | *DMSO-d$_6$ was used as a solvent. δ: 5.96 (1H, d, J = 4.1 Hz), 6.62 (1H, d, J = 4.1 Hz), 7.07-7.16 (2H, m), 7.34 (2H, d, J = 8.3 Hz), 7.41 (1H, d, J = 6.9 Hz), 7.52 (1H, d, J = 6.9 Hz), 7.60 (2H, d, J = 8.3 Hz), 12.40 (1H, br s). | 309 (ESI+) |
| 135 | | δ: 6.05 (1H, s), 6.22-6.74 (2H, m), 7.01-7.13 (3H, m), 7.26-7.32 (1H, m), 7.40-7.53 (3H, m). | 357 (ESI+) |
| 136 | | *DMSO-d$_6$ was used as a solvent. δ: 3.31 (2H, s), 4.66-4.78 (2H, m), 5.29-6.50 (1H, m), 6.47-7.55 (7H, m), 12.47-12.49 (1H, br m). | 389 (ESI+) |
| 137 | | δ: 4.24 (1H, br s), 6.14 (1H, s), 6.48 (1H, t, J = 74.1 Hz), 7.06 (1H, dd, J = 8.8, 2.0 Hz), 7.22-7.69 (6H, m), 9.49 (1H, br s). | 359 (ESI+) |
| 138 | | δ: 6.02 (1H, s), 6.94-7.03 (1H, m), 7.12-7.26 (2H, m), 7.33-7.42 (2H, m), 7.57-7.60 (1H, br m). | 361 (ESI+) |
| 139 | | δ: 6.02 (1H, s), 7.18-7.25 (3H, m), 7.32 (1H, dd, J = 8.6, 2.1 Hz), 7.44-7.51 (2H, m), 7.58 (1H, d, J = 2.1 Hz). | 341 (ESI−) |

TABLE 26-continued

| Example | Structural formula | ¹H-NMR (CDCl₃) | MS |
|---|---|---|---|
| 140 | [Structure: benzimidazole with OMe substituent, connected via CH(OH) to a phenyl bearing Cl and OCF₃] | δ: 3.79 (3H, s), 6.00 (1H, s), 6.84-7.07 (2H, m), 7.20-7.48 (3H, m), 7.58-7.62 (1H, br s). | 373 (ESI+) |

Examples 141 to 148

Compounds 141 to 148 that were produced in the same manner as described in Example 21 by using corresponding raw materials, are shown in Table 27.

TABLE 27

| Example | Structural formula | ¹H-NMR (CDCl₃) | MS |
|---|---|---|---|
| 141 | [Structure: benzimidazole connected via CH(OMe) to 4-(OCF₃)phenyl] | *DMSO-d₆ was used as a solvent.<br>δ: 3.38 (3H, s), 5.67 (1H, s), 7.09-7.19 (2H, m), 7.37 (2H, d, J = 8.6 Hz), 7.43 (1H, d, J = 6.8 Hz), 7.53-7.60 (3H, m), 12.54 (1H, br s). | 323 (ESI+) |
| 142 | [Structure: benzimidazole connected via CH(OEt) to 4-(OCF₃)phenyl] | δ: 1.32 (3H, t, J = 7.1 Hz), 3.60-3.70 (2H, m), 5.72 (1H, s), 7.17-7.30 (4H, m), 7.42-7.46 (1H, m), 7.50 (2H, d, J = 8.8 Hz), 7.72-7.76 (1H, m), 9.38 (1H, br s). | 337 (ESI+) |
| 143 | [Structure: benzimidazole connected via CH(O-n-Pr) to 4-(OCF₃)phenyl] | δ: 0.98 (3H, t, J = 7.4 Hz), 1.64-1.80 (2H, m), 3.48-3.61 (2H, m), 5.71 (1H, s), 7.17-7.29 (4H, m), 7.41-7.47 (1H, m), 7.50 (2H, d, J = 8.6 Hz), 7.71-7.77 (1H, m), 9.41 (1H, br s). | 351 (ESI+) |
| 144 | [Structure: benzimidazole connected via CH(O-iPr) to 4-(OCF₃)phenyl] | δ: 1.25 (3H, d, J = 6.4 Hz), 1.27 (3H, d, J = 6.4 Hz), 3.74-3.87 (1H, m), 5.84 (1H, s), 7.16-7.29 (4H, m), 7.40-7.45 (1H, m), 7.50 (2H, d, J = 8.6 Hz), 7.71-7.76 (1H, m), 9.45 (1H, br s). | 351 (ESI+) |

TABLE 27-continued

| Example | Structural formula | ¹H-NMR (CDCl₃) | MS |
|---|---|---|---|
| 145 | (structure: EtO-CH(3-Cl-4-OCF₃-phenyl)-benzimidazole with F) | δ: 1.30 (3H, t, J = 7.1 Hz), 3.56-3.72 (2H, m), 5.65 (1H, s), 6.91-7.67 (6H, m), 9.90 (1H, br s). | 389 (ESI+) |
| 146 | (structure: EtO-CH(3-Cl-4-OCF₃-phenyl)-benzimidazole) | δ: 1.33 (3H, t, J = 7.1 Hz), 3.61-3.71 (2H, m), 5.69 (1H, s), 7.26-7.31 (3H, m), 7.38-7.46 (2H, m), 7.62 (1H, d, J = 2.0 Hz), 7.70-7.78 (1H, m), 9.40 (1H, br s). | 371 (ESI+) |
| 147 | (structure: EtO-CH(3-Cl-4-OCF₃-phenyl)-benzimidazole with OMe) | δ: 1.29-1.34 (3H, m), 3.60-3.69 (2H, m), 3.83 (3H, s), 5.65 (1H, s), 6.80-7.65 (6H, m), 9.41 (1H, br s). | 401 (ESI+) |
| 148 | (structure: iPrO-CH(4-OCF₃-phenyl)-imidazo[4,5-b]pyridine) | δ: 1.25 (3H, d, J = 6.0 Hz), 1.32 (3H, d, J = 6.0 Hz), 3.80-3.90 (1H, m), 5.88 (1H, s), 7.18 (2H, d, J = 8.2 Hz), 7.23-7.30 (1H, m), 7.57-7.62 (2H, m), 8.03-8.08 (1H, m), 8.44-8.47 (1H, m), 12.79 (1H, s). | 352 (ESI+) |

Example 149

(5-Methoxy-1H-benzimidazol-2-yl)-(4-trifluoromethoxyphenyl)methanol

[Chemical formula 48]

(structure: HO-CH(4-OCF₃-phenyl)-5-OMe-benzimidazole)

The compound of Example 87 (1.4 g) was dissolved in a 1,4-dioxane/water (1:1) mixed solution (18 mL), and concentrated sulfuric acid (414 mg) was added thereto. The mixture was heated for 0.5 hours at 170° C. by means of a microwave reaction apparatus. The reaction mixture was basified with a 10% aqueous solution of sodium hydroxide and extracted with ethyl acetate. The organic layer was washed with saturated brine and then dried over anhydrous sodium sulfate. After distilling off the solvent under reduced pressure, the residue was purified by silica gel column chromatography (33% to 100% ethyl acetate/hexane), and thus the title compound (1.2 g) was obtained as a colorless solid.

¹H-NMR (CDCl₃) δ: 3.75 (3H, s), 6.00 (1H, s), 6.80-6.88 (2H, m), 7.09 (2H, d, J=8.2 Hz), 7.31 (1H, d, J=8.8 Hz), 7.39 (2H, d, J=8.2 Hz).

ESI-MS Found: m/z 339 (M+H)⁺

Examples 150 to 163

Compounds 150 to 163 that were produced in the same manner as described in Example 149 by using corresponding raw materials, are shown in Tables 28 and 29.

TABLE 28

| Example | Structural formula | ¹H-NMR (CDCl₃) | MS |
|---|---|---|---|
| 150 | (benzimidazole with 5-Cl, 2-[CH(OH)-(4-OCF₃-phenyl)]) | δ: 5.99 (1H, s), 7.03 (2H, d, J = 8.2 Hz), 7.12 (1H, dd, J = 8.7, 2.0 Hz), 7.24 (1H, d, J = 8.7 Hz), 7.28-7.34 (3H, m). | 343 (ESI+) |
| 151 | (benzimidazole with 5-OCHF₂, 2-[CH(OH)-(4-OCF₃-phenyl)]) | δ: 6.03 (1H, s), 6.42 (1H, t, J = 74.0 Hz), 6.97 (1H, dd, J = 8.6, 2.0 Hz), 7.06 (2H, d, J = 8.2 Hz), 7.16-7.19 (1H, m), 7.29-7.43 (3H, m). | 375 (ESI+) |
| 152 | (benzimidazole with 5-OH, 2-[CH(OH)-(4-OCF₃-phenyl)]) | *CD₃OD was used as a solvent.<br>δ: 5.96 (1H, s), 6.73 (1H, dd, J = 8.7, 2.4 Hz), 6.90 (1H, d, J = 2.4 Hz), 7.24 (2H, d, J = 8.4 Hz), 7.33 (1H, d, J = 8.7 Hz), 7.58 (2H, d, J = 8.4 Hz). | 325 (ESI+) |
| 153 | (benzimidazole with 4-F, 6-Cl, 2-[CH(OH)-(4-OCF₃-phenyl)]) | δ: 6.08 (1H, s), 6.95 (1H, dd, J = 10.1, 1.6 Hz), 7.12 (2H, d, J = 8.4 Hz), 7.21 (1H, d, J = 1.6 Hz), 7.42 (2H, d, J = 8.4 Hz). | 361 (ESI+) |
| 154 | (benzimidazole with 5-OCF₃, 2-[CH(OH)-(4-OCF₃-phenyl)]) | δ: 6.03 (1H, s), 7.02-7.08 (3H, m), 7.26-7.36 (4H, m), 10.13 (1H, br s). | 393 (ESI+) |
| 155 | (benzimidazole with 5-CF₃, 2-[CH(OH)-(4-OCF₃-phenyl)]) | δ: 4.02 (1H, br s), 6.13 (1H, s), 7.22 (2H, d, J = 7.9 Hz), 7.49-7.89 (5H, m), 9.68 (1H, br s). | 377 (ESI+) |

TABLE 28-continued

| Example | Structural formula | ¹H-NMR (CDCl₃) | MS |
|---|---|---|---|
| 156 | (benzimidazole with 4-F; CH(OH) linked to 4-(OCF₃)phenyl) | δ: 6.10 (1H, s), 6.82-6.95 (1H, m), 6.96-7.22 (4H, m), 7.30-7.44 (2H, m), 10.31 (1H, br s). | 327 (ESI+) |

TABLE 29

| Example | Structural formula | ¹H-NMR (CDCl₃) | MS |
|---|---|---|---|
| 157 | (benzimidazole; CH(OH) linked to 3-Br-4-(OCF₃)phenyl) | δ: 6.04 (1H, s), 7.20-7.26 (3H, m), 7.39 (1H, dd, J = 8.5, 2.1 Hz), 7.49-7.53 (2H, m), 7.78 (1H, d, J = 2.1 Hz). | 387 (ESI+) |
| 158 | (5-OMe-benzimidazole; CH(OH) linked to 3-Br-4-(OCF₃)phenyl) | δ: 3.78 (3H, s), 5.99 (1H, s), 6.86 (1H, dd, J = 8.8, 2.2 Hz), 6.92 (1H, s), 7.20 (1H, dd, J = 8.4, 1.3 Hz), 7.35-7.38 (2H, m), 7.75 (1H, d, J = 2.2 Hz). | 417 (ESI+) |
| 159 | (5-OEt-benzimidazole; CH(OH) linked to 3-Br-4-(OCF₃)phenyl) | δ: 1.41 (3H, t, J = 6.9 Hz), 3.90-4.00 (2H, m), 5.95-5.97 (1H, m), 6.80-6.89 (2H, m), 7.08-7.20 (1H, m), 7.28-7.36 (2H, m), 7.69-7.75 (1H, m). | 431 (ESI+) |
| 160 | (5,6-difluoro-benzimidazole; CH(OH) linked to 4-(OCF₃)phenyl) | δ: 6.02 (1H, s), 7.13-7.25 (4H, m), 7.40-7.44 (2H, m). | 345 (ESI+) |
| 161 | (5-F-benzimidazole; CH(OH) linked to 3-isopropyl-4-(OCF₃)phenyl) | δ: 1.18 (6H, d, J = 6.8 Hz), 3.22-3.35 (1H, m), 6.05 (1H, s), 6.95-7.01 (1H, m), 7.16-7.27 (3H, m), 7.40-7.47 (2H, m). | 369 (ESI+) |

TABLE 29-continued

| Example | Structural formula | ¹H-NMR (CDCl₃) | MS |
|---|---|---|---|
| 162 | | *DMSO-d₆ was used as a solvent.<br>δ: 5.98 (1H, d, J = 3.3 Hz), 6.71 (1H, s), 7.35 (2H, d, J = 8.6 Hz), 7.62 (2H, d, J = 8.6 Hz), 7.79 (1H, br s), 8.26-8.30 (1H, br m), 13.16 (1H, br s). | 328 (ESI+) |
| 163 | | *DMSO-d₆ was used as a solvent.<br>δ: 5.94-6.06 (1H, m), 6.64-6.87 (1H, m), 7.35 (2H, d, J = 8.3 Hz), 7.62 (2H, d, J = 8.3 Hz), 8.00-8.21 (1H, br m), 8.32-8.41 (1H, m), 12.84-13.46 (1H, m). | 386 (ESI−) |

Example 164

5-Fluoro-2-[(2-fluoroethoxy)-(4-trifluoromethoxyphenyl)methyl]-1H-benzimidazole

[Chemical formula 49]

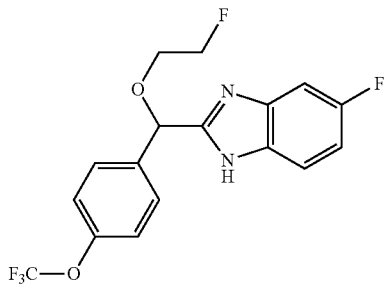 [SMILES: CCCOC(c1ccc(OC(F)(F)F)cc1)c1nc2cc(F)ccc2[nH]1]

The compound of Example 70 (120 mg) was dissolved in 1,4-dioxane (2 mL), and 2-fluoroethanol (22 mg) and concentrated sulfuric acid (99 mg) were sequentially added thereto. The mixture was heated for 5 minutes at 180° C. by means of a microwave reaction apparatus. The mixture was basified with a saturated aqueous solution of sodium hydrogen carbonate and extracted with chloroform. The organic layer was washed with saturated brine and then dried over sodium anhydrous sulfate. After distilling off the solvent under reduced pressure, the residue was purified by silica gel column chromatography (20% to 50% ethyl acetate/hexane), and thus the title compound (63 mg) was obtained as a colorless solid.

¹H-NMR (CDCl₃) δ: 3.74-3.94 (2H, m), 4.52-4.79 (2H, m), 5.77 (1H, s), 6.96-7.04 (1H, m), 7.17-7.26 (3H, m), 7.46-7.54 (3H, m), 9.72 (1H, br s).

ESI-MS Found: m/z 373 (M+H)⁺

Examples 165 to 170

Compounds 165 to 170 that were produced in the same manner as described in Example 164 by using corresponding raw materials, are shown in Table 30.

TABLE 30

| Example | Structural formula | ¹H-NMR (CDCl₃) | MS |
|---|---|---|---|
| 165 | | δ: 3.64-3.79 (2H, m), 3.85-4.01 (2H, m), 5.70 (1H, s), 6.91-7.01 (1H, m), 7.06-7.24 (3H, m), 7.32-7.52 (3H, m), 10.90 (1H, br s). | 371 (ESI+) |

TABLE 30-continued
| Example | Structural formula | ¹H-NMR (CDCl₃) | MS |
|---|---|---|---|
| 166 | 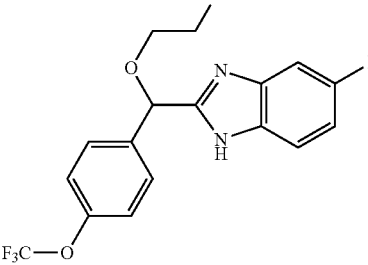 | δ: 0.98 (3H, t, J = 7.4 Hz), 1.67-1.77 (2H, m), 3.47-3.59 (2H, m), 5.67 (1H, s), 6.95-7.04 (1H, m), 7.08-7.67 (6H, m), 9.47-9.56 (1H, m). | 369 (ESI+) |
| 167 | 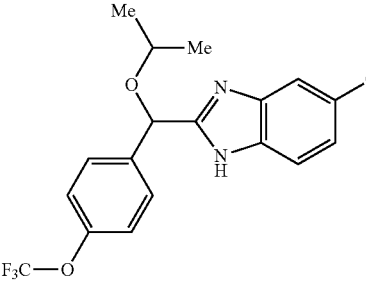 | δ: 1.23-1.28 (6H, m), 3.75-3.83 (4H, m), 5.80 (1H, s), 6.86-6.91 (1.5H, m), 7.17-7.32 (3H, m), 7.48-7.62 (2.5H, m), 9.27-9.33 (1H, m). | 381 (ESI+) |
| 168 | 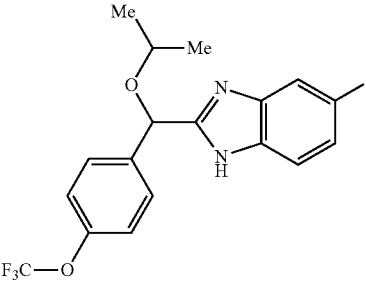 | δ: 1.23-1.29 (6H, m), 1.43 (3H, t, J = 7.0 Hz), 3.75-3.83 (1H, m), 4.04 (2H, q, J = 7.0 Hz), 5.80 (1H, s), 6.85-7.20 (4H, m), 7.28-7.62 (3H, m), 9.21-9.28 (1H, br m). | 395 (ESI+) |
| 169 | 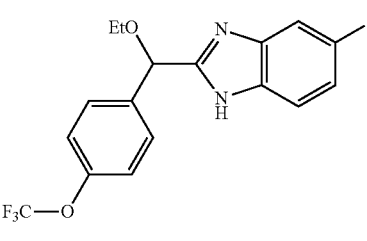 | δ: 1.28 (3H, t, J = 7.0 Hz), 3.54-3.69 (2H, m), 5.67 (1H, s), 7.12-7.24 (3H, m), 7.27-7.73 (4H, m), 10.01 (1H, br s). | 371 (ESI+) |
| 170 | 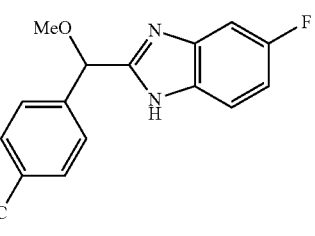 | δ: 3.50 (3H, s), 5.62-5.63 (1H, m), 6.95-7.68 (7H, m), 9.42 (1H, br s). | 325 (ESI+) |

Example 171

5-[(5-Fluoro-1H-benzimidazol-2-yl)methoxymethyl]-2-trifluoromethoxybenzonitrile

[Chemical formula 50]

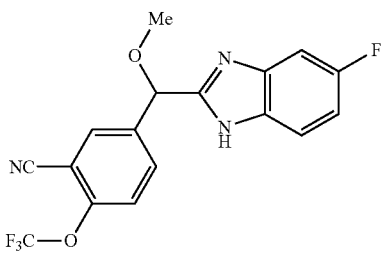

The compound of Example 128 (366 mg) and zinc cyanide (410 mg) were suspended in DMF (4 mL), and argon bubbling was carried out for 10 minutes. Tetrakis(triphenylphosphine)palladium (100 mg) was added to the reaction mixture, and the mixture was heated for 60 minutes at 130° C. by means of a microwave reaction apparatus. Concentrated aqueous ammonia was added to the reaction mixture, and the mixture was extracted with diethyl ether. The organic layer was washed with saturated brine and then dried over anhydrous sodium sulfate. After distilling off the solvent under reduced pressure, the residue was purified by silica gel column chromatography (12% to 100% ethyl acetate/hexane), and the title compound (223 mg) was obtained as a colorless solid.

$^1$H-NMR (CDCl$_3$) δ: 3.53 (3H, s), 5.60-5.61 (1H, m), 6.98-7.08 (1H, m), 7.11-7.15 (0.5H, m), 7.34-7.40 (2H, m), 7.62-7.67 (0.5H, m), 7.72-7.77 (1H, m), 7.85 (1H, d, J=2.2 Hz), 9.52 (1H, br s).

ESI-MS Found: m/z 366 (M+H)$^+$

Example 172

2-[(3-Cyclopropyl-4-trifluoromethoxyphenyl)methoxymethyl]-5-fluoro-1H-benzimidazole

[Chemical formula 51]

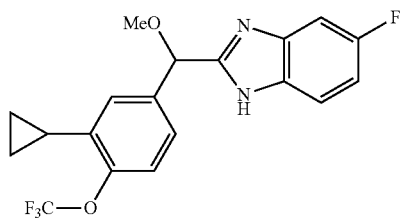

In an argon atmosphere, the compound of Example 128 (96 mg) was dissolved in a toluene/water (2:1) mixed solution (3.3 mL), and cesium carbonate (373 mg), cyclopropylboronic acid (48 mg), and tetrakis(triphenylphosphine)palladium (27 mg) were sequentially added thereto. The mixture was heated for 60 minutes at 130° C. by means of a microwave reaction apparatus. Water was added to the reaction mixture, and the mixture was extracted with ethyl acetate. The organic layer was washed with saturated brine and then dried over anhydrous sodium sulfate. After distilling off the solvent under reduced pressure, the residue was purified by silica gel column chromatography (12% to 100% ethyl acetate/hexane), and thus the title compound (61 mg) was obtained as a colorless solid.

$^1$H-NMR (CDCl$_3$) δ: 0.63-0.69 (2H, m), 0.95-1.01 (2H, m), 2.05-2.15 (1H, m), 3.45 (3H, s), 5.50 (1H, s), 6.95-7.10 (2.5H, m), 7.16-7.24 (2H, m), 7.29-7.40 (1H, m), 7.61-7.65 (0.5H, m), 9.58 (1H, br s).

ESI-MS Found: m/z 381 (M+H)$^+$

Example 173

2-[Ethoxy(4-trifluoromethoxyphenyl)methyl]-5-fluoro-1H-benzimidazolemaleate

[Chemical formula 52]

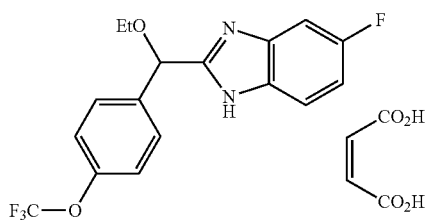

The compound of Example 70 (1.0 g) was dissolved in isopropanol (6 mL), and maleic acid (344 mg) was added thereto. The mixture was stirred for 5 minutes at room temperature. After a solid precipitated out, diisopropyl ether (6 mL) was added to the reaction mixture, and the mixture was subjected to filtration through a glass filter. Thus, the title compound (0.9 g) was obtained as a colorless solid.

$^1$H-NMR (DMSO-d$_6$) δ: 1.22 (3H, t, J=7.0 Hz), 3.55 (2H, q, J=7.0 Hz), 5.77 (1H, s), 6.24 (2H, s), 6.99-7.06 (1H, m), 7.27-7.31 (1H, m), 7.37 (2H, d, J=8.7 Hz), 7.48-7.53 (1H, m), 7.58 (2H, d, J=8.7 Hz).

Example 174

2-[Ethoxy(4-trifluoromethoxyphenyl)methyl]-5-fluoro-1H-benzimidazoleoxalate

[Chemical formula 53]

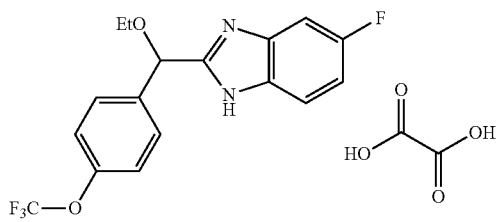

The compound of Example 70 (176 mg) was dissolved in isopropanol (1.5 mL), and oxalic acid (49 mg) was added thereto. The mixture was stirred for 18 hours at room temperature. After a solid precipitated out, diisopropyl ether was added to the reaction liquid, and the solid was collected by filtration through a glass filter. Thus, the title compound (142 mg) was obtained as a colorless solid.

$^1$H-NMR (DMSO-$d_6$) δ: 1.22 (3H, t, J=7.0 Hz), 3.55 (2H, q, J=7.0 Hz), 5.76 (1H, s), 6.97-7.04 (1H, m), 7.26-7.30 (1H, m), 7.37 (2H, d, J=8.7 Hz), 7.47-7.51 (1H, m), 7.57 (2H, d, J=8.7 Hz).

Example 175

2-[Ethoxy(4-trifluoromethoxyphenyl)methyl]-5-fluoro-1H-benzimidazole 4-methylbenzenesulfonate

[Chemical formula 54]

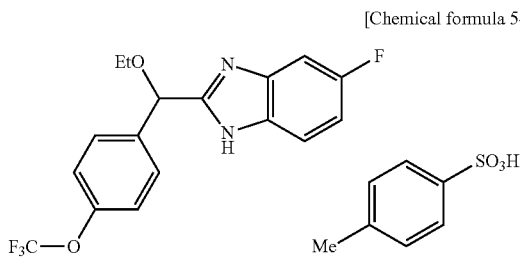

The compound of Example 70 (177 mg) was dissolved in isopropanol (1.2 mL), and 4-methylbenzenesulfonic acid (344 mg) was added thereto. The mixture was stirred for 52 hours at room temperature. After a solid precipitated out, diethyl ether was added to the reaction mixture, and the solid was collected by filtration through a glass filter. Thus, the title compound (246 mg) was obtained as a colorless solid.

$^1$H-NMR (DMSO-$d_6$) δ: 1.24 (3H, t, J=7.0 Hz), 2.27 (3H, s), 3.54-3.70 (2H, m), 6.02 (1H, s), 7.10 (2H, d, J=8.4 Hz), 7.27-7.34 (1H, m), 7.42-7.48 (4H, m), 7.51-7.55 (1H, m), 7.63 (2H, d, J=8.4 Hz), 7.69-7.74 (1H, m).

Example 176

2-[Ethoxy(4-trifluoromethoxyphenyl)methyl]-5-fluoro-1H-benzimidazole benzenesulfonate

[Chemical formula 55]

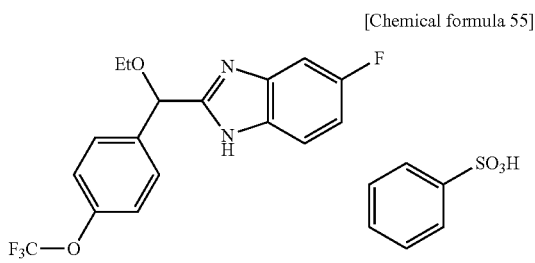 [SMILES: CCOC(c1ccc(OC(F)(F)F)cc1)c1nc2cc(F)ccc2[nH]1 ; O=S(=O)(O)c1ccccc1]

The compound of Example 70 (173 mg) was dissolved in isopropanol (1.5 mL), and benzenesulfonic acid (344 mg) was added thereto. The mixture was stirred for 18 hours at room temperature. After a solid precipitated out, diisopropyl ether was added to the reaction mixture, and the solid was collected by filtration through a glass filter. Thus, the title compound (153 mg) was obtained as a colorless solid.

$^1$H-NMR (DMSO-$d_6$) δ: 1.24 (3H, t, J=7.0 Hz), 3.57-3.68 (2H, m), 6.02 (1H, s), 7.28-7.33 (4H, m), 7.44 (2H, d, J=8.6 Hz), 7.50-7.54 (1H, m), 7.58-7.64 (4H, m), 7.68-7.73 (1H, m).

Example 177

2-[Ethoxy(4-trifluoromethoxyphenyl)methyl]-5-fluoro-1H-benzimidazole phosphate

[Chemical formula 56]

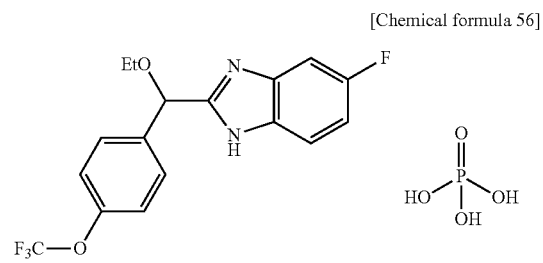 [SMILES: CCOC(c1ccc(OC(F)(F)F)cc1)c1nc2cc(F)ccc2[nH]1 ; O=P(O)(O)O]

The compound of Example 70 (1.0 g) was dissolved in THF (6 mL), and phosphoric acid (325 mg) was added thereto. The mixture was stirred for 2.5 hours at room temperature. After a solid precipitated out, diethyl ether was added to the reaction mixture, and the solid was collected by filtration through a glass filter. Thus, the title compound (1.2 g) was obtained as a colorless solid.

$^1$H-NMR (DMSO-$d_6$) δ: 1.21 (3H, t, J=7.0 Hz), 3.55 (2H, q, J=7.0 Hz), 5.75 (1H, s), 6.97-7.04 (1H, m), 7.26-7.29 (1H, m), 7.36 (2H, d, J=8.7 Hz), 7.48 (1H, brs), 7.57 (2H, d, J=8.7 Hz), 12.56 (1H, brs).

Test Example 1

Representative compounds of the present invention were tested on the selective antagonistic effect against T-type calcium channels (Cav3.2) by way of the following Test Example. For each test, human embryonic kidney cells (HEK293 cells) in which human T-type calcium channels (human Cav3.2) were stably expressed were used.

HEK293 cells in which human Cav3.2 were stably expressed were cultured at 37° C. in Alpha-MEM containing 10% (v/v) fetal bovine serum (FBS), penicillin (100 U/mL), streptomycin (100 µg/mL) and G418 (250 µg/mL). The cells were suspended in the culture medium and seeded onto a 96-well plate, and then the cells were cultured for 24 hours. The culture medium was removed, and the culture medium was replaced with S-MEM containing 5% (v/v) FBS, calcium chloride (0.5 mmol/L), L-glutamine (2 mmol/L), L-alanine (8.9 ng/mL), L-asparagine (13.2 ng/mL), L-aspartic acid (1.33 ng/mL), L-glutamic acid (1.47 ng/mL), glycine (7.5 ng/mL), L-proline (11.5 ng/mL), L-serine (10.5 ng/mL), penicillin (100 U/mL), and streptomycin (100 µg/mL). The cells were cultured for another 24 hours. The culture medium was removed again, and the cells were washed with an assay buffer (140 mmol/L sodium chloride, 5 mmol/L potassium chloride, 0.5 mmol/L magnesium chloride, 0.5 mmol/L calcium chloride, 10 mmol/L glucose, 0.4 mmol/L magnesium sulfate, 10 mmol/L HEPES, and 250 µmol/L sulfinpyrazone, pH 7.4) that had been kept warm at 37° C. Subsequently, the assay buffer in which Fura2-AM, which is a fluorescent $Ca^{2+}$ indicator, was dissolved at 5 µM was added to the cells, and the cells were cultured at 37° C. for 30 minutes. The assay buffer containing dissolved Fura2 was removed, and the cells were washed with the assay buffer. Subsequently, the assay buffer to which a test compound had been added was added to the cells, and the cells were cultured for 15 minutes. The plate was placed in a fluorescence analyzer (Flex Station II, Molecular Devices, LLC), the baseline was measured, and then the change in the intracellular calcium concentration that was caused when an assay buffer containing 100 mmol/L calcium chloride was added, was measured (excited at 340 nm and 380 nm, and detected at 510 nm). Thus, the fluorescence intensity ratios obtainable at the respective wavelengths were calculated.

Meanwhile, the test compound solution was prepared by dissolving each of the test compounds in DMSO to a concentration of 10 mmol/L, and then adding the assay buffer to a predetermined concentration. As a control solution, DMSO was used instead of the test compounds.

The inhibitory effect value (%) of each test compound was calculated by subtracting the average value of the fluorescence intensity ratio for the period of 0 to 20 seconds after the initiation of measurement, from the average value of the fluorescence intensity ratio for the period of 45 to 50 seconds after the initiation of measurement, and comparing the activity in the presence of the test compound with the value in the control solution as the maximum activity of Cav3.2.

Calculation of $IC_{50}$ value: The inhibitory effect of each test compound at concentrations of 0.3, 0.5, 1, 3, 5, 10 and 30 mol/L, respectively, was measured, and the $IC_{50}$ value was calculated by using the curve fitting formula of AssayExplorer (Symyx Technologies, Inc.) (Model 08: sigmoidal inhibition curve).

Curve fitting formula (Model 08: Sigmoidal Inhibition Curve, Vmax+Y2 to Y2)

$$Y = V\max \times (1 - (X^n/(K^n + X^n))) + Y2$$

X=Concentration
Y=% inhibition value
% inhibition value=(RFU (compound)—RFU(LC))/(RFU (HC)−(RFU(LC))
HC: Average of RFU value for the period of 25 to 30 seconds after the addition of $Ca^{2+}$-containing assay buffer after the control solution treatment (for the period of 45 to 50 seconds after the initiation of measurement)
LC: Average of RFU value for the period of 25 to 30 seconds after the addition of non-$Ca^{2+}$-containing assay buffer after the control solution treatment (for the period of 45 to 50 seconds after the initiation of measurement)

The RFU in the formula represents the relative fluorescence unit.

The test results are shown in Table 30.

TABLE 30

| Example | $IC_{50}$ (µmol/L) |
|---|---|
| 1 | 0.32 |
| 3 | 0.47 |
| 4 | 0.65 |
| 5 | 0.21 |
| 6 | 0.59 |
| 12 | 0.10 |
| 13 | 0.27 |
| 16 | 0.49 |
| 27 | 0.92 |
| 29 | 0.37 |
| 32 | 0.63 |
| 44 | 0.01 |
| 45 | 0.25 |
| 46 | 0.22 |
| 47 | 0.59 |
| 48 | 0.14 |

TABLE 30-continued

| Example | $IC_{50}$ (µmol/L) |
|---|---|
| 49 | 0.16 |
| 50 | 0.05 |
| 53 | 0.17 |
| 58 | 0.70 |
| 70 | 0.58 |
| 89 | 0.78 |
| 91 | 0.96 |
| 112 | 0.37 |
| 114 | 0.19 |
| 115 | 0.99 |

Test Example 2

Electrophysiological Test (Patch Clamp Method)

Representative compounds of the present invention were tested on the selective antagonistic effect against T-type calcium channels (Cav3.2) by way of the following Test Example. For each test, human embryonic kidney cells (HEK293 cells) in which human T-type calcium channels (human Cav3.2) were stably expressed were used.

HEK293 cells in which human Cav3.2 were stably expressed were cultured at 37° C. in Alpha-MEM containing 10% (v/v) fetal bovine serum (FBS), penicillin (100 U/mL), streptomycin (100 µg/mL) and G418 (250 µg/mL). The cells were dissociated by Accutase (Sigma-Aldrich Co.) treatment and were used as a suspension in the culture medium. The calcium current was measured with an auto-patch clamp system (Port-a-Patch, Nanion Technologies, GmbH), by using an internal solution (50 mmol/L CsCl, 10 mmol/L NaCl, 60 mmol/L CsF, 2 mmol/L $MgCl_2$, 20 mmol/L EGTA, 10 mmol/L HEPES/CsOH, pH 7.2) and an external solution (80 mmol/L NaCl, 1 mmol/L TEAC1, 3 mmol/L KCl, 35 mmol/L $CaCl_2$, 10 mmol/L $MgCl_2$, 10 mmol/L HEPES, pH 7.2).

The inhibitory effect of the compound against the peak current was measured by fixing the holding potential at −80 mV, and applying a pulse of −20 mV to the cells at an interval of 5 seconds. The compound evaluation was carried out by sequentially replacing the external solution containing the compound (1 µmol/L, 3 µmol/L, 10 µmol/L, and 50 µmol/L), and measuring the current. The inhibition ratio was calculated from the peak current value, and the $IC_{50}$ value was determined by converting the inhibition ratio according to a probit analysis, and then calculating the $IC_{50}$ value from an approximation formula deduced by linear regression.

The results are shown in Table 31.

TABLE 31

| Example | $IC_{50}$ (µmol/L) |
|---|---|
| 1 | 1.92 |
| 44 | 1.01 |
| 53 | 1.77 |
| 70 | 1.76 |
| Mibefradil | 2.99 |

The invention claimed is:
1. A compound represented by formula (I), a pharmaceutically acceptable salt thereof, or a solvate thereof:

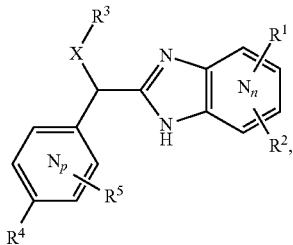

wherein:
ring $N_p$ represents a benzene ring;
the fused heterocyclic ring containing $R^1$ and $N_n$ is represented by following formula:

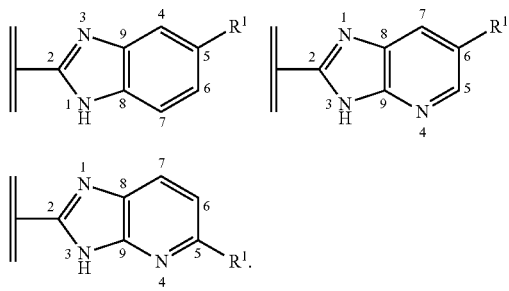

$R^2$ is (1) a hydrogen atom;
$R^1$ is one of (2)-(12) as follows:
  (2) a halogen atom,
  (3) a hydroxyl group,
  (4) a cyano group,
  (5) a nitro group,
  (6) an optionally substituted $C_{1-6}$ alkyl group,
  (7) an optionally substituted $C_{1-6}$ alkoxy group,
  (8) —$SR^6$,
  (9) —$SO_2R^6$,
  (10) —$SO_2NR^6R^7$,
  (11) —(C=O)—$R^6$, or
  (12) an amino group;
$R^6$ and $R^7$, which may be identical or different, each represent an optionally substituted $C_{1-6}$ alkyl group;
$R^3$ represents:
  (1) a hydrogen atom,
  (2) an optionally substituted $C_{1-6}$ alkyl group,
  (3) —(C=O)—$R^8$, or
  (4) an optionally substituted aryl group or heteroaryl group;
$R^8$ represents an optionally substituted $C_{1-6}$ alkyl group;
X represents an oxygen atom, a sulfur atom, —$SO_2$—, or —$N(R^9)$—;
$R^9$ represents an optionally substituted $C_{1-6}$ alkyl group, or may be combined together with $R^3$ and an adjacent nitrogen atom to form an optionally substituted non-aromatic heterocyclic ring;
$R^4$ represents:
  (1) a halo-$C_{1-6}$ alkyl group,
  (2) a halo-$C_{1-6}$ alkoxy group,
  (3) an optionally substituted aralkyloxy group, or
  (4) —$SR^{10}$;
$R^{10}$ represents a halo-$C_{1-6}$ alkyl group;
$R^5$ represents:
  (1) a hydrogen atom, or
  (2) a halogen atom, or
$R^4$ and $R^5$ are combined to form an optionally substituted benzene ring or dioxole ring,
with the proviso that when $R^4$ is an unsubstituted aralkyloxy group and n is 0, $XR^3$ is not OH.

2. The compound according to claim 1, a pharmaceutically acceptable salt thereof, or a solvate thereof, wherein X is an oxygen atom.

3. A compound selected from the group consisting of:
(5-fluoro-1H-benzimidazol-2-yl)-(4-trifluoromethoxyphenyl)methanol;
(5-fluoro-1H-benzimidazol-2-yl)-(4-trifluoromethylsulfanylphenyl)methanol;
(5-fluoro-1H-benzimidazol-2-yl)-(4-trifluoromethylphenyl)methanol;
(5-fluoro-1H-benzimidazol-2-yl)-[3-fluoro-4-(trifluoromethyl)phenyl]methanol;
2-[ethoxy(4-trifluoromethylphenyl)methyl]-5-fluoro-1H-benzimidazole;
(5-fluoro-1H-benzimidazol-2-yl)-[4-(1,1,2,2-tetrafluoroethoxy)phenyl]methanol;
(5-fluoro-1H-benzimidazol-2-yl)-(naphthalen-2-yl)methanol;
(2,2-difluorobenzo[1,3]dioxol-5-yl)-(5-fluoro-1H-benzimidazol-2-yl)methanol;
5-fluoro-2-[isopropoxy(4-trifluoromethoxyphenyl)methyl]-1H-benzimidazole;
5-fluoro-2-[(2-methoxyethoxy)-(4-trifluoromethoxyphenyl)methyl]-1H-benzimidazole;
(6-chloro-3H-imidazo[4,5-b]pyridin-2-yl)-(4-trifluoromethoxyphenyl)methanol;
(6-fluoro-3H-imidazo[4,5-b]pyridin-2-yl)-[4-(4-methylbenzyloxy)phenyl]methanol;
6-chloro-2-[ethoxy(4-trifluoromethoxyphenyl)methyl]-3H-imidazo[4,5-b]pyridine;
6-chloro-2-{ethoxy[4-(4-methylbenzyloxy)phenyl]methyl}-3H-imidazo[4,5-b]pyridine;
2-{ethoxy[4-(4-methylbenzyloxy)phenyl]methyl}-6-fluoro-3H-imidazo[4,5-b]pyridine;
6-chloro-2-{ethoxy[4-(4-fluorobenzyloxy)phenyl]methyl}-3H-imidazo[4,5-b]pyridine;
2-{ethoxy[4-(4-fluorobenzyloxy)phenyl]methyl}-6-fluoro-3H-imidazo[4,5-b]pyridine;
2-{[4-(2,5-difluorobenzyloxy)phenyl]ethoxymethyl}-5-ethoxy-1H-benzimidazole;
5-chloro-2-{[4-(2,5-difluorobenzyloxy)phenyl]ethoxymethyl}-1H-benzimidazole;
2-{[4-(2,5-difluorobenzyloxy)phenyl]ethoxymethyl}-5-trifluoromethyl-1H-benzimidazole;
2-{[4-(2,5-difluorobenzyloxy)phenyl]ethoxymethyl}-5-methoxy-1H-benzimidazole;
5-ethoxy-2-[ethoxy(4-trifluoromethoxyphenyl)methyl]-1H-benzimidazole;
2-[ethoxy(4-trifluoromethoxyphenyl)methyl]-5-fluoro-1H-benzimidazole;
5-ethoxy-2-[methoxy(4-trifluoromethoxyphenyl)methyl]-1H-benzimidazole;
2-{[4-(2,5-difluorobenzyloxy)phenyl]ethoxymethyl}-5-methyl-1H-benzimidazole;
2-[ethoxy(4-trifluoromethoxyphenyl)methyl]-5-methoxy-1H-benzimidazole;

5-chloro-2-[methoxy(4-trifluoromethoxyphenyl)methyl]-1H-benzimidazole;
5-fluoro-2-[methoxy(4-trifluoromethoxyphenyl)methyl]-1H-benzimidazole;
5-ethoxy-2-[ethoxy(4-trifluoromethylsulfanylphenyl)methyl]-1H-benzimidazole;
5-ethoxy-2-{ethoxy[4-(4-methylbenzyloxyl)phenyl]methyl}-1H-benzimidazole;
2-{[4-(2,4-difluorobenzyloxyl)phenyl]ethoxymethyl}-5-ethoxy-1H-benzimidazole;
(5-fluoro-1H-benzimidazol-2-yl)-[3-fluoro-4-(trifluoromethoxy)phenyl]methanol;
[3-bromo-4-(trifluoromethoxy)phenyl]-(5-fluoro-1H-benzimidazol-2-yl)methanol;
2-[ethoxy(3-fluoro-4-trifluoromethoxyphenyl)methyl]-5-fluoro-1H-benzimidazole;
(5-fluoro-1H-benzimidazol-2-yl)-[4-(2,2,2-trifluoroethoxyl)phenyl]methanol;
5-fluoro-2-{methoxy[4-(2,2,2-trifluoroethoxyl)phenyl]methyl}-1H-benzimidazole;
2-{ethoxy[4-(2,2,2-trifluoroethoxyl)phenyl]methyl}-5-fluoro-1H-benzimidazole;
2-[(2,2-difluorobenzo[1,3]dioxol-5-yl)ethoxymethyl]-5-fluoro-1H-benzimidazole;
2-[(2,2-difluorobenzo[1,3]dioxol-5-yl)methoxymethyl]-5-fluoro-1H-benzimidazole;
(5-nitro-1H-benzimidazol-2-yl)-(4-trifluoromethoxyphenyl)methanol;
5-chloro-3H-imidazo[4,5-b]pyridin-2-yl)-(4-trifluoromethoxyphenyl)methanol;
(5-propylsulfanyl-1H-benzimidazol-2-yl)-(4-trifluoromethoxyphenyl)methanol;
(6-chloro-3H-imidazo[4,5-b]pyridin-2-yl)-(2,2-difluorobenzo[1,3]dioxol-5-yl)methanol;
2-{[4-(2,5-difluorobenzyloxyl)phenyl]ethoxymethyl}-5-fluoro-1H-benzimidazole;
2-{[4-(2,5-difluorobenzyloxyl)phenyl]ethoxymethyl}-5-nitro-1H-benzimidazole;
5-ethoxy-2-{ethoxy[4-(4-fluorobenzyloxyl)phenyl]methyl}-1H-benzimidazole;
5-ethoxy-2-{ethoxy[4-(3-fluorobenzyloxyl)phenyl]methyl}-1H-benzimidazole;
5-ethoxy-2-{ethoxy[4-(2-fluorobenzyloxyl)phenyl]methyl}-1H-benzimidazole;
2-{[4-(3,5-dimethoxybenzyloxyl)phenyl]ethoxymethyl)}-5-ethoxy-1H-benzimidazole;
5-ethoxy-2-{ethoxy[4-(4-trifluoromethoxybenzyloxyl)phenyl]methyl}-1H-benzimidazole;
(5-bromo-1H-benzimidazol-2-yl)-(4-trifluoromethoxyphenyl)methanol;
5-bromo-2-[ethoxy(4-trifluoromethoxyphenyl)methyl]-1H-benzimidazole;
2-[hydroxy(4-trifluoromethoxyphenyl)methyl]-1H-benzimidazole-5-carbonitrile;
2-[ethoxy(4-trifluoromethoxyphenyl)methyl]-1H-benzimidazole-5-carbonitrile;
2-[ethoxy(4-trifluoromethoxyphenyl)methyl]-6-fluoro-3H-imidazo[4,5-b]pyridine;
6-bromo-2-[ethoxy(4-trifluoromethoxyphenyl)methyl]-3H-imidazo[4,5-b]pyridine;
2-[ethoxy(4-trifluoromethoxyphenyl)methyl]-5-trifluoromethoxy-1H-benzimidazole;
2-[ethoxy(4-trifluoromethoxyphenyl)methyl]-5-trifluoromethyl-1H-benzimidazole;
5-difluoromethoxy-2-[ethoxy(4-trifluoromethoxyphenyl)methyl]-1H-benzimidazole;
2-[(3-bromo-4-trifluoromethoxyphenyl)methoxymethyl]-5-fluoro-1H-benzimidazole;
2-[(3-bromo-4-trifluoromethoxyphenyl)methoxymethyl]-5-methoxy-1H-benzimidazole;
2-[(3-bromo-4-trifluoromethoxyphenyl)methoxymethyl]-5-ethoxy-1H-benzimidazole;
5-difluoromethoxy-2-[ethoxy(4-trifluoromethylphenyl)methyl]-1H-benzimidazole;
5-difluoromethoxy-2-[methoxy(4-trifluoromethylphenyl)methyl]-1H-benzimidazole;
(5-difluoromethoxy-1H-benzimidazol-2-yl)-(4-difluoromethoxyphenyl)methanol;
(5-difluoromethoxy-1H-benzimidazol-2-yl)-[4-(2,2,2-trifluoroethoxyl)phenyl]methanol;
(5-difluoromethoxy-1H-benzimidazol-2-yl)-(4-trifluoromethylphenyl)methanol;
(3-chloro-4-trifluoromethoxyphenyl)-(5-fluoro-1H-benzimidazol-2-yl)methanol;
(3-chloro-4-trifluoromethoxyphenyl)-(5-methoxy-1H-benzimidazol-2-yl)methanol;
2-[(3-chloro-4-trifluoromethoxyphenyl)ethoxymethyl]-5-fluoro-1H-benzimidazole;
2-[(3-chloro-4-trifluoromethoxyphenyl)ethoxymethyl]-5-methoxy-1H-benzimidazole;
(5-methoxy-1H-benzimidazol-2-yl)-(4-trifluoromethoxyphenyl)methanol;
(5-chloro-1H-benzimidazol-2-yl)-(4-trifluoromethoxyphenyl)methanol;
(5-difluoromethoxy-1H-benzimidazol-2-yl)-(4-trifluoromethoxyphenyl)methanol;
2-[hydroxy(4-trifluoromethoxyphenyl)methyl]-1H-benzimidazol-5-ol;
(5-trifluoromethoxy-1H-benzimidazol-2-yl)-(4-trifluoromethoxyphenyl)methanol;
(4-trifluoromethoxyphenyl)-(5-trifluoromethyl-1H-benzimidazol-2-yl)methanol;
(3-bromo-4-trifluoromethoxyphenyl)-(5-methoxy-1H-benzimidazol-2-yl)methanol;
(3-bromo-4-trifluoromethoxyphenyl)-(5-ethoxy-1H-benzimidazol-2-yl)methanol;
(6-fluoro-3H-imidazo[4,5-b]pyridin-2-yl)-(4-trifluoromethoxyphenyl)methanol;
(6-bromo-3H-imidazo[4,5-b]pyridin-2-yl)-(4-trifluoromethoxyphenyl)methanol;
5-fluoro-2-[(2-fluoroethoxy)-(4-trifluoromethoxyphenyl)methyl]-1H-benzimidazole;
2-[(5-fluoro-1H-benzimidazol-2-yl)-(4-trifluoromethoxyphenyl)methoxy]ethanol;
5-fluoro-2-[propoxy(4-trifluoromethoxyphenyl)methyl]-1H-benzimidazole;
2-[isopropoxy(4-trifluoromethoxyphenyl)methyl]-5-methoxy-1H-benzimidazole;
5-ethoxy-2-[isopropoxy(4-trifluoromethoxyphenyl)methyl]-1H-benzimidazole;
5-chloro-2-[ethoxy(4-trifluoromethoxyphenyl)methyl]-1H-benzimidazole;
5-fluoro-2-[methoxy(4-trifluoromethylphenyl)methyl]-1H-benzimidazole;
a pharmaceutically acceptable salt thereof; and
a solvate thereof.

4. A pharmaceutical composition, comprising the compound according to claim 1, a pharmaceutically acceptable salt thereof, or a solvate thereof.

5. The pharmaceutical composition according to claim 4, further comprising a pharmaceutically acceptable carrier.

6. A method for treating at least one selected from the group consisting of hypertension, atrial fibrillation, arrhythmia, cardiac hypertrophy, cardiac failure, and renal dysfunction, the method comprising administering the compound according to claim 1 to a patient in need thereof.

7. A method for treating hypertension, atrial fibrillation, arrhythmia, cardiac hypertrophy, cardiac failure, or renal dysfunction, the method comprising administering an effective amount of the compound according to claim 1, a pharmaceutically acceptable salt thereof, or a solvate thereof.

8. The compound according to claim 1, a pharmaceutically acceptable salt thereof, or a solvate thereof, wherein the $N_n$ ring is a benzene ring.

9. The compound according to claim 8, selected from the group consisting of:

(5-fluoro-1H-benzimidazol-2-yl)-(4-trifluoromethoxyphenyl)methanol;
(5-fluoro-1H-benzimidazol-2-yl)-(4-trifluoromethylsulfanylphenyl)methanol;
(5-fluoro-1H-benzimidazol-2-yl)-(4-trifluoromethylphenyl)methanol;
(5-fluoro-1H-benzimidazol-2-yl)-[3-fluoro-4-(trifluoromethyl)phenyl]methanol;
2-[ethoxy(4-trifluoromethylphenyl)methyl]-5-fluoro-1H-benzimidazole;
(5-fluoro-1H-benzimidazol-2-yl)-[4-(1,1,2,2-tetrafluoroethoxyl)phenyl]methanol;
(5-fluoro-1H-benzimidazol-2-yl)-(naphthalen-2-yl)methanol;
(2,2-difluorobenzo[1,3]dioxol-5-yl)-(5-fluoro-1H-benzimidazol-2-yl)methanol;
5-fluoro-2-[isopropoxy(4-trifluoromethoxyphenyl)methyl]-1H-benzimidazole;
5-fluoro-2-[(2-methoxyethoxy)-(4-trifluoromethoxyphenyl)methyl]-1H-benzimidazole;
2-{[4-(2,5-difluorobenzyloxy)phenyl]ethoxymethyl}-5-ethoxy-1H-benzimidazole;
5-chloro-2-{[4-(2,5-difluorobenzyloxyl)phenyl]ethoxymethyl}-1H-benzimidazole;
2-{[4-(2,5-difluorobenzyloxyl)phenyl]ethoxymethyl}-5-trifluoromethyl-1H-benzimidazole;
2-{[4-(2,5-difluorobenzyloxyl)phenyl]ethoxymethyl}-5-methoxy-1H-benzimidazole;
5-ethoxy-2-[ethoxy(4-trifluoromethoxyphenyl)methyl]-1H-benzimidazole;
2-[ethoxy(4-trifluoromethoxyphenyl)methyl]-5-fluoro-1H-benzimidazole;
5-ethoxy-2-[methoxy(4-trifluoromethoxyphenyl)methyl]-1H-benzimidazole;
2-{[4-(2,5-difluorobenzyloxyl)phenyl]ethoxymethyl}-5-methyl-1H-benzimidazole;
2-[ethoxy(4-trifluoromethoxyphenyl)methyl]-5-methoxy-1H-benzimidazole;
5-chloro-2-[methoxy(4-trifluoromethoxyphenyl)methyl]-1H-benzimidazole;
5-fluoro-2-[methoxy(4-trifluoromethoxyphenyl)methyl]-1H-benzimidazole;
5-ethoxy-2-[ethoxy(4-trifluoromethylsulfanylphenyl)methyl]-1H-benzimidazole;
5-ethoxy-2-{ethoxy[4-(4-methylbenzyloxyl)phenyl]methyl}-1H-benzimidazole;
2-{[4-(2,4-difluorobenzyloxyl)phenyl]ethoxymethyl}-5-ethoxy-1H-benzimidazole;
(5-fluoro-1H-benzimidazol-2-yl)-[3-fluoro-4-(trifluoromethoxy)phenyl]methanol;
[3-bromo-4-(trifluoromethoxy)phenyl]-(5-fluoro-1H-benzimidazol-2-yl)methanol;
2-[ethoxy(3-fluoro-4-trifluoromethoxyphenyl)methyl]-5-fluoro-1H-benzimidazole;
(5-fluoro-1H-benzimidazol-2-yl)-[4-(2,2,2-trifluoroethoxyl)phenyl]methanol;
5-fluoro-2-{methoxy[4-(2,2,2-trifluoroethoxyl)phenyl]methyl}-1H-benzimidazole;
2-{ethoxy[4-(2,2,2-trifluoroethoxyl)phenyl]methyl}-5-fluoro-1H-benzimidazole;
2-[(2,2-difluorobenzo[1,3]dioxol-5-yl)ethoxymethyl]-5-fluoro-1H-benzimidazole;
2-[(2,2-difluorobenzo[1,3]dioxol-5-yl)methoxymethyl]-5-fluoro-1H-benzimidazole;
(5-nitro-1H-benzimidazol-2-yl)-(4-trifluoromethoxyphenyl)methanol;
(5-propylsulfanyl-1H-benzimidazol-2-yl)-(4-trifluoromethoxyphenyl)methanol;
2-{[4-(2,5-difluorobenzyloxyl)phenyl]ethoxymethyl}-5-fluoro-1H-benzimidazole;
2-{[4-(2,5-difluorobenzyloxyl)phenyl]ethoxymethyl}-5-nitro-1H-benzimidazole;
5-ethoxy-2-{ethoxy[4-(4-fluorobenzyloxyl)phenyl]methyl}-1H-benzimidazole;
5-ethoxy-2-{ethoxy[4-(3-fluorobenzyloxyl)phenyl]methyl}-1H-benzimidazole;
5-ethoxy-2-{ethoxy[4-(2-fluorobenzyloxyl)phenyl]methyl}-1H-benzimidazole;
2-{[4-(3,5-dimethoxybenzyloxyl)phenyl]ethoxymethyl}-5-ethoxy-1H-benzimidazole;
5-ethoxy-2-{ethoxy[4-(4-trifluoromethoxybenzyloxyl)phenyl]methyl}-1H-benzimidazole;
(5-bromo-1H-benzimidazol-2-yl)-(4-trifluoromethoxyphenyl)methanol;
5-bromo-2-[ethoxy(4-trifluoromethoxyphenyl)methyl]-1H-benzimidazole;
2-[hydroxy(4-trifluoromethoxyphenyl)methyl]-1H-benzimidazole-5-carbonitrile;
2-[ethoxy(4-trifluoromethoxyphenyl)methyl]-1H-benzimidazole-5-carbonitrile;
2-[ethoxy(4-trifluoromethoxyphenyl)methyl]-5-trifluoromethoxy-1H-benzimidazole;
2-[ethoxy(4-trifluoromethoxyphenyl)methyl]-5-trifluoromethyl-1H-benzimidazole;
5-difluoromethoxy-2-[ethoxy(4-trifluoromethoxyphenyl)methyl]-1H-benzimidazole;
2-[(3-bromo-4-trifluoromethoxyphenyl)methoxymethyl]-5-fluoro-1H-benzimidazole;
2-[(3-bromo-4-trifluoromethoxyphenyl)methoxymethyl]-5-methoxy-1H-benzimidazole;
2-[(3-bromo-4-trifluoromethoxyphenyl)methoxymethyl]-5-ethoxy-1H-benzimidazole;
5-difluoromethoxy-2-[ethoxy(4-trifluoromethylphenyl)methyl]-1H-benzimidazole;
5-difluoromethoxy-2-[methoxy(4-trifluoromethylphenyl)methyl]-1H-benzimidazole;
(5-difluoromethoxy-1H-benzimidazol-2-yl)-(4-difluoromethoxyphenyl)methanol;
(5-difluoromethoxy-1H-benzimidazol-2-yl)-[4-(2,2,2-trifluoroethoxyl)phenyl]methanol;
(5-difluoromethoxy-1H-benzimidazol-2-yl)-(4-trifluoromethylphenyl)methanol;
(3-chloro-4-trifluoromethoxyphenyl)-(5-fluoro-1H-benzimidazol-2-yl)methanol;
(3-chloro-4-trifluoromethoxyphenyl)-(5-methoxy-1H-benzimidazol-2-yl)methanol;
2-[(3-chloro-4-trifluoromethoxyphenyl)ethoxymethyl]-5-fluoro-1H-benzimidazole;
2-[(3-chloro-4-trifluoromethoxyphenyl)ethoxymethyl]-5-methoxy-1H-benzimidazole;

(5-methoxy-1H-benzimidazol-2-yl)-(4-trifluoromethoxyphenyl)methanol;
(5-chloro-1H-benzimidazol-2-yl)-(4-trifluoromethoxyphenyl)methanol;
(5-difluoromethoxy-1H-benzimidazol-2-yl)-(4-trifluoromethoxyphenyl)methanol;
2-[hydroxy(4-trifluoromethoxyphenyl)methyl]-1H-benzimidazol-5-ol;
(5-trifluoromethoxy-1H-benzimidazol-2-yl)-(4-trifluoromethoxyphenyl)methanol;
(4-trifluoromethoxyphenyl)-(5-trifluoromethyl-1H-benzimidazol-2-yl)methanol;
(3-bromo-4-trifluoromethoxyphenyl)-(5-methoxy-1H-benzimidazol-2-yl)methanol;
(3-bromo-4-trifluoromethoxyphenyl)-(5-ethoxy-1H-benzimidazol-2-yl)methanol;
5-fluoro-2-[(2-fluoroethoxy)-(4-trifluoromethoxyphenyl)methyl]-1H-benzimidazole;
2-[(5-fluoro-1H-benzimidazol-2-yl)-(4-trifluoromethoxyphenyl)methoxy]ethanol;
5-fluoro-2-[propoxy(4-trifluoromethoxyphenyl)methyl]-1H-benzimidazole;
2-[isopropoxy(4-trifluoromethoxyphenyl)methyl]-5-methoxy-1H-benzimidazole;
5-ethoxy-2-[isopropoxy(4-trifluoromethoxyphenyl)methyl]-1H-benzimidazole;
5-chloro-2-[ethoxy(4-trifluoromethoxyphenyl)methyl]-1H-benzimidazole;
5-fluoro-2-[methoxy(4-trifluoromethylphenyl)methyl]-1H-benzimidazole;
a pharmaceutically acceptable salt thereof; and
a solvate thereof.

* * * * *